(12) United States Patent
Moretta et al.

(10) Patent No.: US 8,465,931 B2
(45) Date of Patent: Jun. 18, 2013

(54) THERAPEUTIC AND DIAGNOSTIC METHODS AND COMPOSITIONS TARGETING 4IG-B7-H3 AND ITS COUNTERPART NK CELL RECEPTOR

(75) Inventors: Alessandro Moretta, Genoa (IT); Roberta Castriconi, Genoa (IT); Christina Bottino, Genoa (IT); Lorenzo Moretta, Genoa (IT)

(73) Assignees: Innate Pharma S.A., Marseille (FR); University of Genova, Genoa (IT)

( * ) Notice: Subject to any disclaimer, the term of this patent is extended or adjusted under 35 U.S.C. 154(b) by 253 days.

(21) Appl. No.: 12/775,531

(22) Filed: May 7, 2010

(65) Prior Publication Data
US 2010/0285531 A1 Nov. 11, 2010

Related U.S. Application Data

(62) Division of application No. 11/659,175, filed as application No. PCT/IB2005/002688 on Aug. 2, 2005, now Pat. No. 7,732,131.

(60) Provisional application No. 60/598,727, filed on Aug. 3, 2004.

(51) Int. Cl.
*G01N 33/53* (2006.01)

(52) U.S. Cl.
USPC .......................... 435/7.1; 424/130.1

(58) Field of Classification Search
None
See application file for complete search history.

(56) References Cited

U.S. PATENT DOCUMENTS
2005/0169932 A1 8/2005 Cheung

FOREIGN PATENT DOCUMENTS

| | | | |
|---|---|---|---|
| EP | 1514933 | | 1/2001 |
| WO | WO 99/46281 | | 9/1999 |
| WO | WO 00/68266 | | 11/2000 |
| WO | WO/01/18204 | * | 3/2001 |
| WO | WO 01/18204 A1 | | 3/2001 |
| WO | WO/01/94413 | * | 12/2001 |
| WO | WO 01/94413 A2 | | 12/2001 |
| WO | WO 02/08279 | | 1/2002 |
| WO | WO 02/10187 | | 2/2002 |
| WO | WO 02/32375 | | 4/2002 |
| WO | WO 2004/001381 | | 12/2003 |

OTHER PUBLICATIONS

Shields et al. (JBC, vol. 277, No. 30, Jul. 2002, pp. 26733-26740).*
Castriconi, R. et al. "Identification of 4Ig-B7-H3 as a Neuroblastoma-Associated Molecule That Exerts a Protective Role From an NK Cell-Mediated Lysis", *PNAS*, Aug. 24, 2004, pp. 12640-12645, vol. 101, No. 34.
Cleary, M. L. et al. "Cloning and Structural Analysis of cDNAs for *bcl-2* and a Hybrid *bcl-2*/Immunoglobulin Transcript Resulting from the t(14;18) Translocation", *Cell*, Oct. 10, 1986, pp. 19-28, vol. 47.
Seto, M. et al. "Alternative Promoters and Exons, Somatic Mutation and Deregulation of the *Bcl-2-Ig* Fusion Gene in Lymphoma", *The EMBO Journal*, 1988, pp. 123-131, vol. 7, No. 1.
Sun, M. et al. "Characterization of Mouse and Human B7-H3 Genes", *The Journal of Immunology*, 2002, pp. 6294-6297, vol. 168.
Chapoval, A. I. et al. "B7-H3: A Costimulatory Molecule for T Cell Activation and IFN-γ Production", *Nature Immunology*, Mar. 2001, pp. 269-274, vol. 2, No. 3.
NCBI database, Genbank Accession No. M14745, Apr. 27, 1993, pp. 1-3.
Steinberger, P. et al. "Molecular Characterization of Human 4Ig-B7-H3, a Member of the B7 Family with Four Ig-Like Domains", *The Journal of Immunology*, 2004, pp. 2352-2359, vol. 172.
NCBI datatbase, Genbank Accession No. X06487, Mar. 26, 1993, pp. 1-2.
Xu, H. et al. "4Ig-B7H3: A Target for Monoclonal Antibody (mAb) Therapy of Human Neuroblastoma (NB)", *ANR*, 2008, Poster TR84.
Suh, W. et al. "The B7 family member B7-H3 preferentially down-regulates T helper type 1-mediated immune responses", *Nature Immunology*, Sep. 2003, pp. 899-906, vol. 4, No. 9.
Hashiguchi, M. et al. "Triggering receptor expressed on myeloid cell-like transcript 2 (TLT-2) is a counter-receptor for B7-H3 and enhances T cell responses", *PNAS*, Jul. 29, 2008, pp. 10495-10500, vol. 105, No. 30.
Xu, J. et al. "Soluble Mouse B7-H3 Down-Regulates Dendritic Cell Stimulatory Capacity to Allogenic T Cell Proliferation and Production of IL-2 and IFN-γ", *Cellular & Molecular Immunology*, Jun. 2006, pp. 235-240, vol. 3, No. 3.
Zang, X et al. "The B7 Family and Cancer Therapy: Costimulation and Coinhibition", *Clin. Cancer. Res.*, Sep. 15, 2007, pp. 5271-5279, vol. 13, No. 18.
Crispen, P.L. et al. "Tumor Cell and Tumor Vasculature Expression of B7-H3 Predict Survival in Clear Cell Renal Cell Carcinoma", *Clin. Cancer Res.*, Aug. 15, 2008, pp. 5150-5157, vol. 14, No. 16.
Zang, X. et al. "B7-H3 and B7x are highly expressed in human prostate cancer and associated with disease spread and poor outcome", *PNAS*, Dec. 4, 2007, pp. 19458-19463, vol. 104, No. 49.
Dong, H. et al. "B7-H1, a third member of the B7 family, co-stimulates T-cell proliferation and interleukin-10 secretion", *Nature Medicine*, Dec. 1999, pp. 1365-1369, vol. 5, No. 12.

(Continued)

*Primary Examiner* — Laura B Goddard
*Assistant Examiner* — Meera Natarajan
(74) *Attorney, Agent, or Firm* — Saliwanchik, Lloyd & Eisenschenk

(57) ABSTRACT

The present invention relates to the identification of 4Ig-B7-H3 protein as a tumor associated molecule that imparts protection from NK cell-mediated lysis via a 4Ig-B7-H3 receptor on NK cells. The invention provides compounds that interfere with interactions between the 4Ig-B7-H3 protein and its receptor that can be used to potentiate NK cell cytotoxicity. Also provided are compounds that bind 4Ig-B7-H3-expressing cells so as to inhibit or eliminate them. The compounds are particularly useful in the treatment of tumors, inflammatory conditions, infections and transplantation. Also provided are methods for diagnosing disease by detecting a 4Ig-B7-H3 protein.

15 Claims, 8 Drawing Sheets

OTHER PUBLICATIONS

Henry, J. et al. "Structure and evolution of the extended B7 family", *Immunology Today*, Jun. 1999, pp. 285-288, vol. 20, No. 6.

Prasad, D.V. et al. "Murine B7-H3 is a negative Regulator of T Cells", *The Journal of Immunology*, 2004, pp. 2500-2506, vol. 173.

Mahnke, K. et al. "Induction of immunosuppressive functions of dendritic cells in vivo by CD4+CD25+ regulatory T cells: Role of B7-H3 expression and antigen presentation", *Eur. J. Immunology*, 2007, pp. 2117-2126, vol. 37.

Hunter et al., "The Role of the CD28/B7 Interaction in the Regulation of NK Cell Responses During Infection with *Toxoplasma gondii*," *The Journal of Immunology*, 1997, pp. 2285-2293, vol. 158.

\* cited by examiner

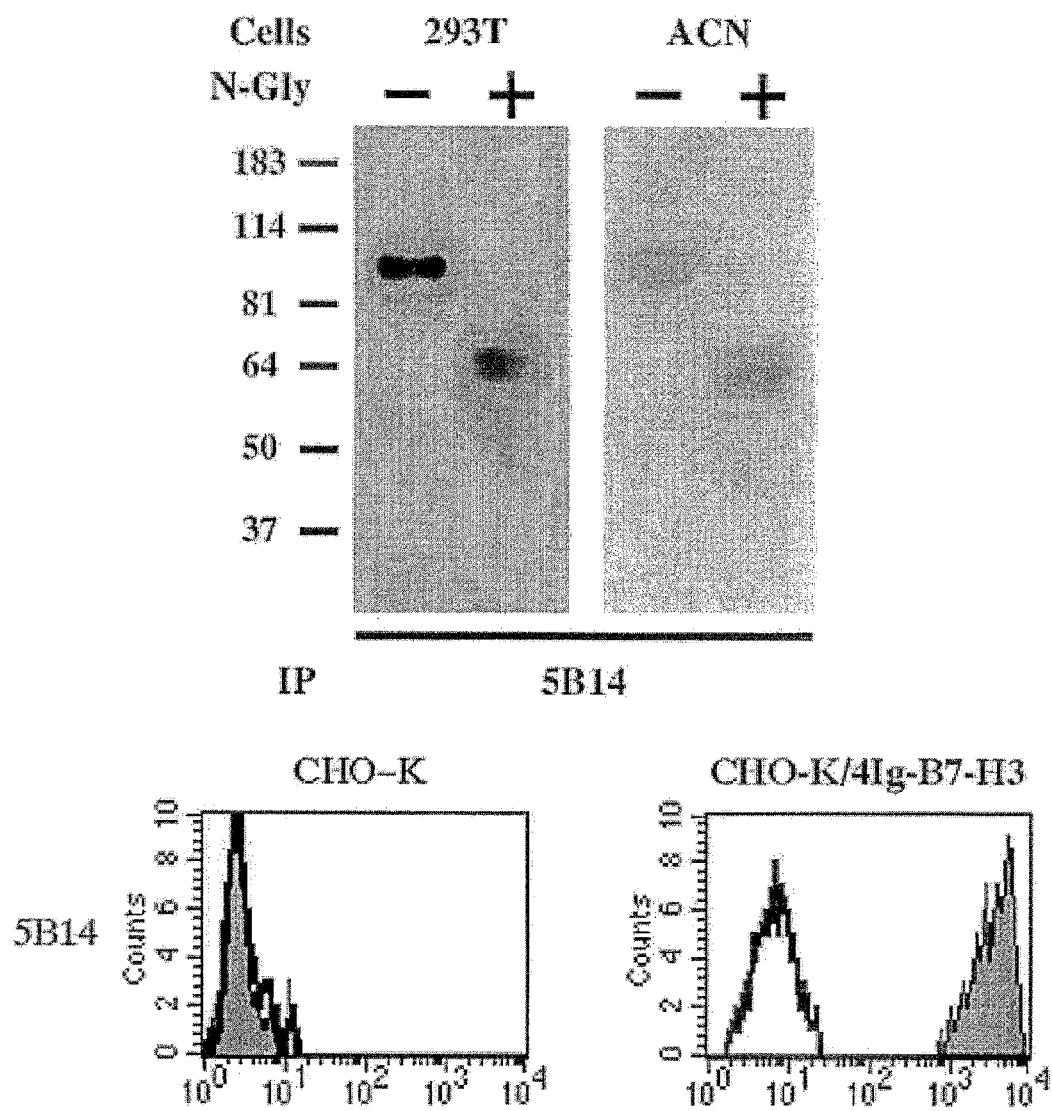

| Cells | Histotype | 5B14 mAb | GD2 mAb |
|---|---|---|---|
| Resting NK cells | | − | − |
| Activated NK cells | | − | − |
| Resting T cells | | − | − |
| PHA blasts | | − | − |
| Resting B cells | | − | − |
| Granulocytes | | − | − |
| Monocytes | | +/− | − |
| IDC | | ++ | − |
| mDC | | ++ | − |
| YT | NK cell line | − | ++ |
| NK92 | NK cell line | − | − |
| CEMB | T leukemia | − | − |
| Jurkat | T leukemia | − | +/− |
| H9 | T leukemia | − | +/− |
| HSB2 | T leukemia | | |
| Raji | Burkitt lymphoma | − | − |
| LCL 721.221 | EBV cell line | − | − |
| EA | Endothelial cells | ++ | − |
| K562 | Erythroleukemia | + | − |
| MM6 | Promyelocytic leukemia | + | − |
| U937 | Myeloid leukemia | + | − |
| 293T | Embryonic fibroblasts | ++ | − |
| M14 | Melanoma | ++ | − |
| FO-1 | Melanoma | ++ | ++ |
| Me 1074 | Melanoma | ++ | ++ |
| H460 | Lung carcinoma | ++ | − |
| SMMC | Hepatoma | ++ | − |
| HELA | Cervical carcinoma | ++ | − |
| IGROV-1 | Ovarian carcinoma | ++ | − |
| SKNEP | Kidney carcinoma | + | − |
| A172 | Glioblastoma | ++ | − |
| HT29 | Colon carcinoma | ++ | − |
| CX2 | Colon carcinoma | ++ | − |
| SKBr3 | Breast carcinoma | + | − |
| MDAM B453 | Breast carcinoma | +/− | − |

FIG. 7

| L | IgV$_1$ | IgC$_1$ | IgV$_2$ | IgC$_2$ | TM | CT |
|---|---------|---------|---------|---------|-----|-----|
| 1-26 | 27-140 | 141-244 | 245-358 | 359-461 | 462-492 | 493-534 |

FIG. 8

SEQUENCE LISTING

<160> NUMBER OF SEQ ID NOS: 5

<210> SEQ ID NO 1
<211> LENGTH: 3419
<212> TYPE: DNA
<213> ORGANISM: Homo sapiens

<400> SEQUENCE: 1

```
ccggcctcag ggacgcaccg gagccgcctt tccgggcctc aggcggattc tccggcgcgg      60
cccgccccgc ccctcggact ccccgggccg cccccggccc ccattcgggc cgggcctcgc     120
tgcggcggcg actgagccag gctgggccgc gtccctgagt cccagagtcg gcgcggcgcg     180
gcaggggcag ccttccacca cggggagccc agctgtcagc cgcctcacag gaagatgctg     240
cgtcggcggg gcagccctgg catgggtgtg catgtgggtg cagccctggg agcactgtgg     300
ttctgcctca caggagccct ggaggtccag gtccctgaag acccagtggt ggcactggtg     360
ggcaccgatg ccaccctgtg ctgctccttc tccctgagc ctggcttcag cctggcacag     420
ctcaacctca tctggcagct gacagatacc aaacagctgg tgcacagctt tgctgagggc     480
caggaccagg gcagcgccta tgccaaccgc acggccctct cccggacct gctggcacag     540 ggcaacgcat ccctgaggct gcagcgcgtg cgtgtggcgg acgagggcag cttcacctgc     600
ttcgtgagca tccgggattt cggcagcgct gccgtcagcc tgcaggtggc cgctccctac     660
tcgaagccca gcatgaccct ggagcccaac aaggacctgg ggccagggga cacggtgacc     720
atcacgtgct ccagctacca gggctaccct gaggctgagg tgttctggca ggatgggcag     780
ggtgtgcccc tgactggcaa cgtgaccacg tcgcagatgg ccaacgagca gggcttgttt     840
gatgtgcaca gcatcctgcg ggtggtgctg ggtgcaaatg gcacctacag ctgcctggtg     900
cgcaaccccg tgctgcagca ggatgcgcac agctctgtca ccatcacacc ccagagaagc     960
cccacaggag ccgtggaggt ccaggtccct gaggacccgg tggtggccct agtgggcacc    1020
gatgccaccc tgcgctgctc cttctcccc gagcctggct tcagcctggc acagctcaac    1080
ctcatctggc agctgacaga caccaaacag ctggtgcaca gtttcaccga aggccgggac    1140
cagggcagcg cctatgccaa ccgcacggcc ctcttccgg acctgctggc acaaggcaat    1200
gcatccctga ggctgcagcg cgtgcgtgtg gcggacgagg cagcttcac ctgcttcgtg    1260 agcatccggg atttcggcag cgctgccgtc agcctgcagg tggccgctcc ctactcgaag    1320
cccagcatga ccctggagcc caacaaggac ctgcggccag gggacacggt gaccatcacg    1380
tgctccagct accggggcta ccctgaggct gaggtgttct ggcaggatgg cagggtgtg    1440 cccctgactg gcaacgtgac cacgtcgcag atggccaacg agcagggctt gtttgatgtg    1500
cacagcgtcc tgcgggtggt gctgggtgcg aatggcacct acagctgcct ggtgcgcaac    1560
cccgtgctgc agcaggatgc gcacggctct gtcaccatca gggcagcc tatgacattc    1620 cccccagagg ccctgtgggt gaccgtgggg ctgtctgtct gtctcattgc actgctggtg    1680
```

```
gccctggctt tcgtgtgctg agaaagatc aaacagagct gtgaggagga gaatgcagga    1740
gctgaggacc aggatgggga gggagaaggc tccaagacag ccctgcagcc tctgaaacac    1800
tctgacagca agaagatga tggacaagaa atagcctgac catgaggacc agggagctgc    1860 taccccctccc tacagctcct accctctggc tgcaatgggg ctgcactgtg agccctgccc    1920
ccaacagatg catcctgctc tgacaggtgg gctccttctc caaggatgc gatacacaga    1980 ccactgtgca gccttatttc tccaatggac atgattccca agtcatcctg ctgccttttt    2040
tcttatagac acaatgaaca gaccacccac aaccttagtt ctctaagtca tcctgcctgc    2100
tgccttattt cacagtacat acatttctta gggacacagt acactgacca catcaccacc    2160
ctcttcttcc agtgctgcgt ggaccatctg gctgcctttt ttctccaaaa gatgcaatat    2220
tcagactgac tgacccctg ccttatttca ccaaagacac gatgcatagt caccccggcc    2280
ttgtttctcc aatggccgtg atacactagt gatcatgttc agccctgctt ccacctgcat    2340
agaatctttt cttctcagac agggacagtg cggcctcaac atctcctgga gtctagaagc    2400
tgtttccttt cccctccttc ctcctcttgc tctagcctta atactggcct tttccctccc    2460
tgccccaagt gaagacaggg cactctgcgc ccaccacatg cacagctgtg catggagacc    2520
tgcaggtgca cgtgctggaa cacgtgtggt tcccccctgg cccagcctcc tctgcagtgc    2580
ccctctcccc tgcccatcct ccccacggaa gcatgtgctg gtcacactgg ttctccaggg    2640
gtctgtgatg gggcccctgg gggtcagctt ctgtccctct gccttctcac ctctttgttc    2700
cttctttttc atgtatccat tcagttgatg tttattgagc aactacagat gtcagcactg    2760
tgttaggtgc tgggggccct gcgtgggaag ataaagttcc tccctcaagg actccccatc    2820
cagctgggag acagacaact aactacactg caccctgcgg tttgcagggg gctcctgcct    2880
ggctccctgc tccacacctc ctctgtggct caaggcttcc tggatacctc acccccatcc    2940
cacccataat tcttacccag agcatggggt tggggcggaa acctggagag agggacatag    3000
cccctcgcca cggctagaga atctggtggt gtccaaaatg tctgtccagg tgtgggcagg    3060
tgggcaggca ccaaggccct ctggaccttt catagcagca gaaaaggcag agcctggggc    3120
agggcagggc caggaatgct ttggggacac cgaggggact gccccccacc cccaccatgg    3180
tgctattctg gggctgggc agtcttttcc tggcttgcct ctggccagct cctgcctct    3240 ggtagagtga gacttcagac gttctgatgc cttccggatg tcatctctcc ctgccccagg    3300
aatggaagat gtgaggactt ctaatttaaa tgtgggactc ggagggattt tgtaaactgg    3360
gggtatattt tggggaaaat aaatgtcttt gtaaaaagct taaaaaaaaa aaaaaaaa     3419
```

<210> SEQ ID NO 2
<211> LENGTH: 534
<212> TYPE: PRT
<213> ORGANISM: Homo sapiens

<400> SEQUENCE: 2

```
Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
```

-continued

```
            65                  70                  75                  80
Glu Gly Gln Asp Gln Gly Ser Ala Tyr Ala Asn Arg Thr Ala Leu Phe
                    85                  90                  95

Pro Asp Leu Leu Ala Gln Gly Asn Ala Ser Leu Arg Leu Gln Arg Val
                100                 105                 110

Arg Val Ala Asp Glu Gly Ser Phe Thr Cys Phe Val Ser Ile Arg Asp
                115                 120                 125

Phe Gly Ser Ala Ala Val Ser Leu Gln Val Ala Pro Tyr Ser Lys
            130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
                180                 185                 190

Ser Gln Met Ala Asn Glu Gln Gly Leu Phe Asp Val His Ser Ile Leu
            195                 200                 205

Arg Val Val Leu Gly Ala Asn Gly Thr Tyr Ser Cys Leu Val Arg Asn
        210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
                260                 265                 270

Glu Pro Gly Phe Ser Leu Ala Gln Leu Asn Leu Ile Trp Gln Leu Thr
            275                 280                 285

Asp Thr Lys Gln Leu Val His Ser Phe Thr Glu Gly Arg Asp Gln Gly
        290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
                340                 345                 350

Ser Leu Gln Val Ala Ala Pro Tyr Ser Lys Pro Ser Met Thr Leu Glu
            355                 360                 365

Pro Asn Lys Asp Leu Arg Pro Gly Asp Thr Val Thr Ile Thr Cys Ser
370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
                420                 425                 430

Asn Gly Thr Tyr Ser Cys Leu Val Arg Asn Pro Val Leu Gln Gln Asp
            435                 440                 445

Ala His Gly Ser Val Thr Ile Thr Gly Gln Pro Met Thr Phe Pro Pro
450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495
```

-continued

```
Glu Glu Glu Asn Ala Gly Ala Glu Asp Gln Asp Gly Glu Gly Gly
            500                 505                 510

Ser Lys Thr Ala Leu Gln Pro Leu Lys His Ser Asp Ser Lys Glu Asp
        515                 520                 525

Asp Gly Gln Glu Ile Ala
        530

<210> SEQ ID NO 3
<211> LENGTH: 17
<212> TYPE: DNA
<213> ORGANISM: Artificial
<220> FEATURE:
<223> OTHER INFORMATION: Primer 2Ig-B7-H3 UP

<400> SEQUENCE: 3
atgctgcgtc ggcgggg                                                  17

<210> SEQ ID NO 4
<211> LENGTH: 23
<212> TYPE: DNA
<213> ORGANISM: Artificial
<220> FEATURE:
<223> OTHER INFORMATION: Primer B7-H3-DW

<400> SEQUENCE: 4
ggtcaggcta tttcttgtcc atc                                           23

<210> SEQ ID NO 5
<211> LENGTH: 18
<212> TYPE: DNA
<213> ORGANISM: Artificial
<220> FEATURE:
<223> OTHER INFORMATION: Primer 4Ig-B7-H3 UP

<400> SEQUENCE: 5
cagccgcctc acaggaag                                                 18
```

THERAPEUTIC AND DIAGNOSTIC METHODS AND COMPOSITIONS TARGETING 4IG-B7-H3 AND ITS COUNTERPART NK CELL RECEPTOR

CROSS-REFERENCE TO RELATED APPLICATIONS

This application is a divisional of U.S. Ser. No. 11/659,175, filed Jan. 31, 2007, which is the U.S. national stage application of International Patent Application No. PCT/IB2005/002688, filed Aug. 2, 2005, which claims the benefit of U.S. Provisional Patent Application No. 60/598,727, filed Aug. 3, 2004, the disclosures of which are hereby incorporated by reference in their entireties, including all figures, tables and amino acid or nucleic acid sequences.

FIELD OF THE INVENTION

The present invention relates to the identification of 4Ig-B7-H3 protein as a tumor associated molecule that imparts protection from NK cell-mediated lysis via a 4Ig-B7-H3 receptor on NK cells. The invention provides compounds that interfere with interactions between the 4Ig-B7-H3 protein and its receptor that can be used to potentiate NK cell cytotoxicity. Also provided are compounds that bind 4Ig-B7-H3-expressing cells so as to inhibit or eliminate them. The compounds are particularly useful in the treatment of tumors, inflammatory conditions, infections and transplantation. Also provided are methods for diagnosing disease by detecting a 4Ig-B7-H3 protein.

BACKGROUND

Natural killer (NK) cells are a sub-population of lymphocytes that are involved in non-conventional immunity. Characteristics and biological properties of NK cells include the expression of surface antigens such as CD16, CD56 and/or CD57, and the absence of the alpha/beta or gamma/delta TCR complex expressed on the cell surface; the ability to bind to and kill cells that fail to express "self" MHC/HLA antigens by the activation of specific cytolytic enzymes; the ability to kill tumor cells or other diseased cells that express a NK activating receptor-ligand; and the ability to release protein molecules called cytokines that stimulate or inhibit the immune response.

NK cell activity is regulated by a complex mechanism that involves both activating and inhibitory signals. Several distinct classes of NK-specific receptors have been identified that play an important role in the NK cell mediated recognition and killing of HLA Class I deficient target cells. One such class of receptors, the NCRs (for Natural Cytotoxicity Receptors), includes NKp30, NKp46 and NKp44, all members of the Ig superfamily. Their cross-linking, induced by specific mAbs, strongly activates NK cells, resulting in increased intracellular $Ca^{++}$ levels, triggering of cytotoxicity, and lymphokine release.

NK cells are negatively regulated by major histocompatibility complex (MHC) class I-specific inhibitory receptors. These specific receptors bind to polymorphic determinants of MHC class I molecules or HLA present on other cells and inhibit NK cell lysis. In humans, certain members of a family of receptors termed killer Ig-like receptors (K IRs) recognize groups of HLA class I alleles.

NK cell population or clones that are KIR mismatched, i.e., population of NK cells that express KIR that are not compatible with a HLA molecules of a host, have been shown to be the most likely mediators of the graft anti-leukemia effect seen in allogeneic transplantation (Ruggeri, L., et al, Science 295, 2097-2100). One way of reproducing this effect in a given individual would be to use reagents that block interactions between inhibitory receptors on NK cells and their ligands which impart a protection from NK cell mediated lysis. Accordingly, practical and effective approaches in the modulation of NK cell activity would be of great value. Such an approach would be useful in the treatment of a wide range of diseases.

Certain proliferative diseases such as cancers lack effective treatment. Neuroblastomas, carcinomas and melanomas are particularly notable examples of such cancers. Neuroblastoma has a particularly poor prognosis. Neuroblastoma, the most common solid tumor of childhood, can arise anywhere along the sympathetic nervous system (Brodeur, G.-M. Neuroblastoma. (2003) *Nat Rev Cancer*. 3,203-216; Schwab, M., Westermann, F., Hero, B., & Berthold, F. (2003) *Lancet Oncol*. 4,472-480). Frequently, the primary tumor localizes in the abdomen with the adrenal gland being the most common site. The age of 1 year represents an important prognostic cut-off. Under 1 year of age most tumors are localized (stages 1-2) or, if disseminated, undergo maturation into benign ganglioneuromas or regress spontaneously (the so called stage 4S). On the contrary, most children of more than 1 year of age present with a highly disseminated disease at diagnosis with metastasis involving bone marrow (BM), brain, liver and skin (stage 4) and a very poor prognosis. Indeed, neuroblastoma is the tumor with the highest risk of death in children. In particular, due to drug resistance or relapse after conventional therapy, children at stage 4 have very poor survival rates (3 years probability survival <15%). One of the aims of the current research is to improve our understanding of the biological behavior of neuroblastoma and to identify novel markers that would be used for diagnosis, monitoring of the disease as well as for attempting innovative therapeutic approaches. In particular, the characterization of surface molecules expressed by neuroblastoma cells would allow a more precise identification and quantification of tumor cells, particularly in the BM, a frequent site of tumor relapses. This will improve the diagnosis and allow to better define the risk grade in a particular patient as well as to deliver the most appropriate therapy. In this context, the disialoganglioside GD2 is generally used as a neuroblastoma-associated marker (Schulz, G., Cheresh, D.-A., Varki, N.-M., Yu, A., Staffileno, L.-K., & Reisfeld R.-A. (1984) *Cancer Res*. 44,5914-5920; Hakomori, S. (1984) *Annu.Rev.Immunol*. 2, 103-126). However, anti-GD2-monoclonal antibodies (mAb) also react with cells other than tumor cells. A conceivable explanation is that GD2 shed from the cell surface of neuroblastoma may bind to the surface of other cells and react with anti-GD2 specific mAb (Ladish, S., Wu, Z.-L, Feig, S., Schwartz, E., Floutsis, G., Wiley, F., Lenarsky, C., & Seeger, R. (1987) *Int. J. Cancer*. 39, 73-76; Valentino, L., Moss, T., Olson, E., Wang, H.-J., Elashoff, R., & Ladisch, S. (1990) *Blood* 75,1564-1567). Identification of novel surface antigens expressed by neuroblastoma would also allow to selectively isolate fresh tumor cells that could be assessed for their susceptibility to NK-mediated lysis. Indeed, in vitro-cultured neuroblastoma cell lines have been shown to be susceptible to NK-mediated lysis (Sivori, S., Parolini, S., Marcenaro, E., Castriconi, R., Pende, D., Millo, R., & Moretta, A. (2000) *J. Neuroimmunol*. 107: 220-225). There is therefore a need in the art for novel surface antigens expressed on cancer cells.

SUMMARY OF THE INVENTION

The aim of the present study was to identify novel surface markers that would allow a precise detection of neuroblastoma cells. Thanks to the generation of novel mAbs, the inventors identified the 4Ig-B7-H3 molecule (Sun, M., Richards, S., Prasad, D.-V., Mai, X.-M., Rudensky, A, & Dong, C. (2002) *J. Immunol.* 168,6294-6297; Steinberger, P., Majidic, O., Derdak, S.-V., Pfistershammer, K., Kirchberger, S., Klauser, C., Zlabinger, G., Pickl, W.-F., Stockl, J. & Knapp, W. (2004) *J. Immunol.* 172, 2352-2359) as a valuable surface antigen for detection of neuroblastoma cells, particularly in BM aspirates, as well as other cancer cells. Perhaps more importantly, the inventors provide evidence that 4Ig-B7-H3 molecules play a protective role in tumor cells by inhibiting NK-mediated cell lysis. This inhibitory effect can be reversed by mAb-mediated masking of 4Ig-B7-H3 molecule. The results provide a basis for novel immunotherapeutic approaches, for example using compounds that eliminate tumor cells expressing the antigen or that remove protective effect to the tumor cells conferred by the antigen, compounds that potentiate the activity of NK cells, of infusing activated NK cells to patients.

The 4Ig-B7-H3 polypeptide is a member of the B7 family, described in Steinberger et al, 2004, J. Immunol. 172:2352-2359, the disclosure of which is incorporated herein by reference. This four immunoglobulin domain-containing 4Ig-B7-H3 polypeptide had been previously referred to as B7-H3 and reported to have 2 immunoglobin domains (Chapoval et al, Nat. Immunol. 2:269, the disclosure of which is incorporated herein by reference). This 2Ig form appears to describe an alternatively spliced form. It will be appreciated that the methods of the invention described with respect to the four immunoglobulin domain-containing protein can also be practised with the two-immunoglobulin domain containing protein. As used herein, the term "4Ig-B7-H3 receptor" or "4Ig-B7-H3R" refers to a cell surface molecule capable of interacting with the 4Ig-B7-H3 protein, and that is found on all or a fraction of NK cells. Preferably, the NK cell receptor is expressed exclusively on NK cells (resting or activated), although the term also encompasses receptors that are also expressed on other cell types. The nucleotide (cDNA) sequence encoding the 4Ig-B7-H3 protein and the amino acid sequences of the 4Ig-B7-H3 protein are shown in SEQ ID NOS 1 and 2, respectively, as well as in Genbank accession nos. NM_001024736 and NP_001019907, respectively, and in FIG. 3 of Steinberger et al. (2004), the disclosures of each of the preceding being incorporated herein by reference for the nucleic acid and amino acid sequences.

The invention now provides compounds that interfere with interactions between the 4Ig-B7-H3 protein and its receptor that can be used to potentiate NK cell cytotoxicity. Also provided are compounds that bind 4Ig-B7-H3-expressing cells, which compounds will be useful to inhibit or eliminate them as well as to identify them (e.g as a diagnostic or research tool). The compounds are particularly useful in the treatment of tumors, inflammatory conditions, infections and transplantation.

The present study provides two important insights into neuroblastoma cell biology and into the relationship of this tumor with NK-mediated immune responses. First, we identified 4Ig-B7-H3 (Sun (2002); Steinberger (2004)) as a novel surface marker that is specific for tumor cells, especially neuroblastoma, at least in BM aspirates. Second, we show that this molecule, belonging to the B7 family, inhibits the NK-mediated lysis of neuroblastoma by interacting with a still undefined receptor expressed by NK cells. The present data may have a noticeable impact in improving the diagnosis of neuroblastoma and, possibly, in future attempts of new therapeutic approaches.

In a preferred aspect, the invention thus provides a method of killing a tumor cell, the method comprising bringing said cell into contact with a ligand that specifically binds to a 4Ig-B7-H3 polypeptide, wherein the ligand is capable of inducing death of the tumor cell. In one example the ligand is an antibody capable of mediating lysis of a cell to which it is bound, for example an antibody of the IgG1 or IgG3 subtype, or an antibody linked to a toxic moiety. Alternatively, the ligand is a small molecule which is toxic to a cell to which it is bound or which is linked to a molecule which is toxic to a cell to which it is bound The invention therefore also provides more generally a method of inducing the lysis of a cell or of relieving the resistance to lysis of a cell, the method comprising bringing said cell into contact with a ligand, preferably an antibody, that specifically binds to a 4Ig-B7-H3 polypeptide and is capable of mediating the lysis of the cell. Preferably the ligand is an antibody, for example an antibody having an Fc region capable of interacting with an Fc receptor (e.g. CD16) on an NK cell, or an antibody functionalized with a toxic molecule.

In another aspect the invention discloses a method of targeting a tumor cell, the method comprising bringing said cell into contact with a ligand, preferably an antibody, that specifically binds to a 4Ig-B7-H3 polypeptide. The ligand may optionally be linked to a molecule of interest which is to be brought into contact with the tumor cell.

In another aspect the invention discloses a method of identifying a tumor cell, the method comprising bringing a cell into contact with a ligand, preferably an antibody, that specifically binds to a 4Ig-B7-H3 polypeptide, and detecting binding of the ligand to said cell, wherein a determination that said ligand binds to said cell indicates that the cell is a tumor cell. In another embodiment, the method comprises detecting a nucleic acid encoding a 4Ig-B7-H3 polypeptide in a cell, preferably bringing a nucleic acid from a cell into contact with a nucleic acid probe that hybridises to a nucleic acid encoding a 4Ig-B7-H3 polypeptide, and detecting the presence of said nucleic acid encoding a 4Ig-B7-H3 polypeptide, wherein a determination that said nucleic acid encoding a 4Ig-B7-H3 polypeptide is present indicates that the cell is a tumor cell. Optionally, said method further comprises the step of treating an individual harboring such a tumor cell with a ligand of a 4Ig-B7-H3 polypeptide, preferably a cytotoxic antibody or other ligand capable of inducing or enhancing the death or lysis of a cell.

In another aspect the invention discloses a method for treating an individual having a tumor, the method comprising determining whether tumor cells in said subject express a 4Ig-B7-H3 polypeptide, the expression of a 4Ig-B7-H3 polypeptide being indicative of a subject responding to a ligand of a 4Ig-B7-H3 polypeptide, and treating said subject whose tumor cells express a 4Ig-B7-H3 polypeptide with a ligand of a 4Ig-B7-H3 polypeptide. More preferably, the ligand is a cytotoxic antibody or other ligand capable of inducing or enhancing the death or lysis of a cell.

In another aspect, the invention provides a method of potentiating NK cell activation comprising bringing an NK cell into contact with a compound that blocks an interaction between a 4Ig-B7-H3 polypeptide and a 4Ig-B7-H3 receptor, or between a 4Ig-B7-H3 polypeptide and an NK cell.

In another aspect, the invention provides a method of inhibiting NK cell activation comprising bringing an NK cell into contact with a 4Ig-B7-H3 polypeptide.

In another aspect, the invention provides a method of identifying an NK cell, comprising bringing an NK cell into contact with a 4Ig-B7-H3 polypeptide and detecting binding of the polypeptide to the NK cell, wherein a determination that the polypeptide binds the cell indicates the cell is an NK cell.

In another aspect, the invention provides a method of identifying a tumor cell, comprising bringing an cell into contact with a ligand of a 4Ig-B7-H3 polypeptide, and detecting binding of the ligand to the cell, wherein a determination that the ligand binds the cell indicates the cell is a tumor cell.

In another aspect, the invention provides a method of identifying a dendritic cell, comprising bringing an cell into contact with a ligand of a 4Ig-B7-H3 polypeptide, and detecting binding of the ligand to the cell, wherein a determination that the ligand binds the cell indicates the cell is a dendritic cell.

In another aspect, the invention provides a method of treating a patient with a proliferative disorder, preferably a tumor, the method comprising, administering a therapeutically effective amount of an antibody to said patient that specifically binds to a 4Ig-B7-H3 polypeptide. Preferably said therapeutic antibody has a human IgG1 or an IgG3 Fc portion and is capable of inducing the elimination of a target cell to which it is bound. Optionally, the method further comprises determining the 4Ig-B7-H3 status of tumor cells within said patient; preferably 4Ig-B7-H3 status is determined using an immunological assay or an assay to detect 4Ig-B7-H3-encoding mRNA in the cells.

In another aspect, the invention provides a method of potentiating NK cell activity in an individual comprising administering to said individual a compound that blocks an interaction between the 4Ig-B7-H3 polypeptide and an NK cell (or between the 4Ig-B7-H3 polypeptide and a 4Ig-B7-H3 receptor).

In another aspect, the invention provides a method of treatment of a disease in a human subject in need thereof, comprising: a) administering to said subject a compound that blocks an interaction between the 4Ig-B7-H3 polypeptide and a 4Ig-B7-H3 receptor or an NK cell; and, b) administering to said subject a therapeutic antibody that can be bound by CD16.

Preferably said therapeutic antibody has a human IgG1 or an IgG3 Fc portion and is capable of inducing the elimination of a target cell to which it is bound.

Preferably, said compound that blocks an interaction between the 4Ig-B7-H3 polypeptide and a 4Ig-B7-H3 receptor or an NK cell is an antibody or comprises an antigen binding fragment thereof.

Methods of Potentiating NK ell Activity

The present invention thus provides novel compositions and methods that overcome current difficulties in NK cell activation and provide additional advantageous features and benefits. In one exemplary aspect, the invention provides compounds that facilitate the activation of human NK cells. More particularly, the invention provides novel compounds that block interactions of the 4Ig-B7-H3 protein with the inhibitory 4Ig-B7-H3 receptor (4Ig-B7-H3R) on NK cells and neutralizes the receptor's inhibitory signals, resulting in potentiation of NK cell cytotoxicity in NK cells expressing 4Ig-B7-H3R. Preferred compound are modified 4Ig-B7-H3 proteins, and anti-4Ig-B7-H3 antibodies and fragments and derivatives thereof.

In a first aspect, the invention provides a modified 4Ig-B7-H3 protein, wherein said protein blocks interaction of a 4Ig-B7-H3 protein with the inhibitory 4Ig-B7-H3 receptor (4Ig-B7-H3R) on NK cells, neutralizes the 4Ig-B7-H3R-mediated inhibitory signal of the NK cells, and potentiates the activity of the NK cells. Such a modified B7-H3 protein is typically a fragment of a 4Ig-B7-113 protein, a 4Ig-B7-H3 protein or fragment comprising one or more amino acid deletions or substitutions, or any other B7-H3 protein or fragment which has been modified so as to block the activity of a B7-H3 receptor on an NK cell. Selecting a suitable protein for use in such a method can for example be carried out by determining whether the 4Ig-B7-H3 polypeptide binds an NK cell, and whether the polypeptide inhibits the activation or cytotoxicity of an NK cell, wherein a suitable 4Ig-B7413 polypeptide will bind an NK cell but will not inhibit the activation or cytotoxicity of an NK cell.

In a second aspect, the invention provides antibodies, antibody fragments, and derivatives of either thereof, wherein said antibody, fragment, or derivative blocks interaction of the 4Ig-B7-H3 protein with the inhibitory 4Ig-B7-H3 receptor (4Ig-B7-H3R) on NK cell neutralizes the 4Ig-B7-H3R-mediated inhibitory signal of the NK cells, and potentiates the activity of the NK cells. More preferably, the antibody binds a human 4Ig-B7-H3 receptor. In another preferred embodiment, the antibody of this invention binds the human 4Ig-B7-H3 protein.

The NK potentiating compounds of this invention specifically block the functioning of a 4-Ig-B7-H3 receptor and/or inhibit binding of a 4Ig-B7-H3 molecule to a 4-Ig-B7-H3 receptor, thereby facilitating NK cell activity. Both activities are inferred by the term "neutralize the inhibitory activity of human 4Ig-B7-H3R," as used herein. The ability of the antibodies of this invention to "facilitate NK cell activity," "facilitate NK cell cytotoxicity," "facilitate NK cells," "potentiate NK cell activity, " "potentiate NK cell cytotoxicity," or "potentiate NK cells" in the context of this invention means that the antibody permits NK cells expressing a 4Ig-B7-H3R on their surface to be capable of lysing cells that express on their surface a corresponding ligand for that particular inhibitory receptor (e.g., a 4Ig-B7-H3 protein). In one aspect, the invention provides an antibody that facilitates NK cell activity in vivo.

Also encompassed is a method of activating an NK cell, the method comprising contacting an NK cell with a compound, preferably an antibody, fragment, or derivative which blocks the interaction of the 4Ig-B7-H3 protein with the inhibitory 4Ig-B7-H3 receptor (4Ig-B7-H3R). The activation of the NK cell may be in vivo or in vitro. In a preferred aspect, the invention encompasses a method of treating an individual, for example an individual having a tumor, inflammatory disease or infectious disease, the method comprising contacting an NK cell with a compound, preferably an antibody, fragment, or derivative which blocks the interaction of the 4Ig-B7-H3 protein with the inhibitory 4Ig-B7-H3 receptor (4Ig-B7-H3R). Preferably the compound neutralizes the 4Ig-B7-H3R-mediated inhibitory signal of the NK cells.

In a preferred embodiment, the invention provides an antibody that binds the 4Ig-B7-H3 human receptor, reverses inhibition of NK cell cytotoxicity mediated by this receptor, and competes with 5B14 or 7-517 for binding to the 4Ig-B7-H3 human receptor. Optionally, said antibody is a chimeric, human, or humanized antibody.

In another preferred embodiment, the invention provides an antibody that binds the human 4Ig-B7-H3 protein, reverses inhibition of NK cell cytotoxicity mediated by this protein, and competes with 5B14 or 7-517 for binding to the human 4Ig-B7-H3. Optionally, said antibody is not 7-517. Optionally, said antibody is a chimeric, human, or humanized antibody.

In another aspect, the present invention provides a method of producing an antibody suitable for use in potentiating NK cell activity, and/or for the treatment of a proliferative or inflammatory disorder or an infectious disease, said method comprising: i) providing one or a plurality of antibodies that specifically bind to a 4Ig-B7-H3 polypeptide or a 4Ig-B7-H3 receptor; ii) testing the ability of each of the antibodies to potentiate NK cell activity; iii) selecting an antibody from the plurality that potentiates NK cell activity; and iv) making the antibody suitable for human administration.

In another aspect, the present invention provides a method of producing an antibody suitable for use in potentiating NK cell activity, and/or for the treatment of a proliferative or inflammatory disorder or an infectious disease, said method comprising: i) providing one or a plurality of antibodies that specifically bind to a 4Ig-B7-H3 polypeptide or a 4Ig-B7-H3 receptor; ii) testing the ability of each of the antibodies to block interaction of the 4Ig-B7-H3 protein with a 4Ig-B7-H3 receptor or an NK cell; iii) selecting an antibody from the plurality that blocks said interaction; and iv) making the antibody suitable for human administration.

Preferably, the antibody in the above methods is made suitable for human administration by humanizing or chimerizing it.

In other aspects the invention provides use of a modified 4Ig-B7-H3 protein to block 4Ig-B7-H3R function and relieve NK inhibition (e.g. potentiate NK cell activity). It will be appreciated that proteins of the invention can be in any suitable form, including in purified or isolated form. The present invention provides variants of the 4Ig-B7-H3 proteins which function as 4Ig-B7-H3 inhibitors, preferably competitive inhibitors to a native 4Ig-B7-H3 protein. Examples include peptides comprising amino acid sequences sufficiently homologous to or derived from the amino acid sequence of the 4Ig-B7-H3 protein, e.g., an amino acid sequence shown in SEQ ID NO 2 or in Steinberger et al (2004), supra, which include less amino acids than the full length 4Ig-B7-H3 protein and/or which comprises an amino acid substitution so as to bind a 4Ig-B7-H3 receptor and compete with a native 4Ig-B7-H3 polypeptide but which block the NK cell inhibitory activity of the 4Ig-B7-H3 receptor on NK cells. Such a protein would potentiate NK cell activity. Preferred examples of an NK potentiating polypeptide include a 4Ig-B7-H3 protein comprising a contiguous span of at least 6 amino acids, preferably at least 8 to 10 amino acids, more preferably at least 12, 15, 20, 25, 30, 40, 50, 100, 150, 200, 250, 300, 400 or 500 amino acids of a sequence of SEQ ID NO 2. In one example, the protein comprises at least 1, 2, 3, 5, 10 or 20 amino acid substitutions. In another aspect, a 4Ig-B7-H3 protein comprises a portion of a 4Ig-B7-H3 protein, and comprises one or more domains selected from the domains consisting of: IgV1, IgC1, IgV2 and IgC2. Preferably the NK cell potentiating polypeptide is a soluble 4Ig-B7-H3 polypeptide.

Methods of Eliminating 4Ig-B7-H3-Expressing Disease Cells

The present invention also demonstrates that the human 4Ig-B7-H3 protein and its receptor provide methods for producing antibodies useful for the treatment of proliferative and inflammatory disorders characterized by 4Ig-B7-H3-expressing cells. 4Ig-B7-H3 ligands, including but not limited to antibodies, are capable of specifically targeting the expanded cells underlying such disorders, for example expanded neuroblastoma, melanoma or carcinoma cells, and mature and/or immature dendritic cells. The ligands can limit the pathological effects of the cell proliferation by, e.g., neutralizing the protective effect of the 4Ig-B7-H3 protein to the proliferating cell, by targeting proliferating cells for destruction by the immune system (e.g. via antibody-dependent cytotoxicity, also referred to as ADCC), or, by killing the cells directly by contacting them with a cytotoxic agent such as a radioisotope, toxin, or drug. Methods of using the ligands and antibodies for the treatment of any of a number of proliferative disorders, preferably neuroblastomas, melanomas or carcinomas, are also provided, as are kits comprising the herein-described antibodies as well as instructions for their use.

Accordingly, the present invention provides a method of treating a patient with having a proliferative or inflammatory disorder, the method comprising administering to the patient a ligand, preferably an antibody, that specifically binds to a 4Ig-B7-H3 polypeptide. The present invention also provides a method of treating a patient with a proliferative or inflammatory disorder, the method comprising a) determining the 4Ig-B7-H3 status of a target cell within the patient, and b) administering to the patient a ligand, preferably an antibody, that specifically binds to a 4Ig-B7-H3 polypeptide, preferably a 4Ig-B7-H3 that is prominently expressed on the target cell. The target cell is preferably a proliferating cell.

Examples of preferred proliferating disorders are tumors, including but not limited to neuroblastoma, carcinomas and melanomas. Diagnostic protocols relating to said method are further detailed herein.

In one embodiment, the 4Ig-B7-H3 status of a target cell is determined using an immunological assay. In another embodiment, the 4Ig-B7-H3 status is determined using a functional assay to determine the activity of the 4Ig-B7-H3 present on target cells (e.g. proliferating cells). In another embodiment, the 4Ig-B7-H3 status is determined using an assay to detect 4Ig-B7-H3-encoding mRNA in the target cells. In another embodiment, the receptor is detectably present on at least 50% of the target cells.

In other embodiments, the invention provides a method of identifying a proliferating cell, especially a tumor cell, or a dendritic cell, the method comprising detecting the presence or absence of a 4Ig-B7-H3 polypeptide or nucleic acid, wherein a positive detection indicates that the cells is a proliferating cell, especially a tumor cell, or a dendritic cell. The 4Ig-B7-H3 status of a target cell is determined using any suitable method, for example an immunological assay, an assay to detect 4Ig-B7-H3-encoding mRNA in the target cells.

In one embodiment, the antibody used to treat a subject or proliferating cell comprises an Fc portion, preferably an Fc portion of the IgG1 or IgG3 subclass. In another embodiment, the antibody is an antibody fragment, preferably an antigen-binding fragment. In another embodiment, the antibody is a cytotoxic antibody. In another embodiment, the cytotoxic antibody comprises an element selected from the group consisting of radioactive isotope, toxic peptide, and toxic small molecule. In another embodiment, the antibody is humanized or chimeric. In another embodiment, the radioactive isotope, toxic peptide, or toxic small molecule is directly attached to the antibody. In another embodiment, the cytotoxic antibody is derived from the same antibody used to determine said 4Ig-B7-H3 status in the immunological assay.

In another aspect, the present invention provides a method of producing an antibody suitable for use in the treatment of a proliferative of inflammatory disorder, said method comprising: i) providing one or a plurality of antibodies that specifically bind to a 4Ig-B7-H3 polypeptide; ii) testing the ability of each of the antibodies to bind to a 4Ig-B7-H3 polypeptide or to a target cell; iii) selecting an antibody from the plurality that binds to said 4Ig-B7-H3 polypeptide or target cell; and iv) making the antibody suitable for human administration. In one embodiment, the target cells are proliferating cells, In an other embodiment, the target cells are cells taken from a patient having proliferative of inflammatory disorder.

Preferably, the antibody in the above methods is made suitable for human administration by humanizing or chimerizing it.

In another embodiment, the method further comprises the step of linking a cytotoxic agent to the antibody. In another embodiment, the cytotoxic agent is a radioactive isotope, a toxic polypeptide, or a toxic small molecule. In another embodiment, the cytotoxic agent is directly linked to the antibody. In another embodiment, the antibody is an antibody fragment.

In one embodiment, the antibody binds to at least 20%, 30%, 40%, 50%, 60%, 70% or 80% of the target cells (proliferating cells such as tumor cells, for example) taken from one or more of the patients. In another embodiment the antibody may be used to eliminate a small numuber of target cells that have escaped or have the potential to escape lysis by NK cells (such as via ADCC), for example the antibody may bind to a smaller portion of target cells, e.g. less than 10%, 5%, 1%, 0.1% of target cells taken from one or more of the patients.

It will be appreciated that while the present specification provides numerous examples of antibodies that bind to 4Ig-B7-H3, it will also be to use any other non-antibody or non-polypeptide 4Ig-B7-H3 ligands in the same manner. For example, any small molecule or peptide which binds to 4Ig-B7-H3 can be used to eliminate a target (e.g. tumor) cell; said small molecule or peptide may advantageously comprise or be linked to a toxic moiety that directly induces death of the target cell.

The 4Ig-B7-H3 ligands may also be useful for the treatment of tumors which are non-responsive or refractory to immunotherapeutic treatment, for example, because an individual's tumor cells are resistant to lysis by a cytotoxic T lymphocyte, or most preferably an NK cell. "Non-responsive" or "refractory" describes patients treated with a cancer therapy (e.g., an immunotherapy) which is not clinically adequate to treat or relieve one or more symptoms associated with cancer. Typically, such patients suffer from severe, persistently active disease and require additional therapy to ameliorate the symptoms associated with their cancer. The phrase can also describe patients who respond to therapy yet suffer from side effects, relapse, develop resistance, etc.

In other embodiments, as further provided below, the invention provides diagnostic methods that can be used in the diagnosis and treatment of individuals. The invention provides a method of diagnosis, comprising: detecting the presence or absence of a 4Ig-B7-H3 polypeptide or nucleic acid in an individual, wherein a positive detection indicates that the individual is suffering from or is susceptible to a disorder. Preferably the disorder may include but is not limited to a proliferative disorder, for example a tumor or immunoproliferative disorder. The 4Ig-B7-H3 status of a target cell is determined using using any suitable method, for example an immunological assay, an assay to detect 4Ig-B7-H3-encoding mRNA in the target cells.

Diagnostics

In one aspect the invention provides method that can be used in diagnostic and prognostic methods. The invention provides methods for determining whether a particular cell is a tumor cell, and/or whether an individual harbouring such a cell has or is susceptible to having a tumor or cancer, the method comprising detecting the expression of a 4Ig-B7-H3 polypeptide by a cell, wherein a determination that said cell expresses a 4Ig-B7-H3 polypeptide indicates that said cell is a tumor cell, and/or that an individual harbouring said cell has or is susceptible to having a tumor or cancer.

The invention also provides method that can be used to determine whether a cell, generally a tumor cell, is or may become resistant or susceptible to lysis, as well as whether a cell is susceptible of becoming a tumor cell (e.g. because it is resistant to lysis), the method comprising detecting the expression of a 4Ig-B7-H3 polypeptide by a tumor cell, wherein a determination that said cell expresses a 4Ig-B7-H3 polypeptide indicates that the cell may be or may become resistant or susceptible to lysis, and/or that said cell is susceptible of becoming a tumor cell.

Accordingly the invention also provides methods of determining whether an individual may be or is susceptible to being resistant to immunotherapeutic treatments, particularly treatment that involve or preferably increase the activity of cells capable of lysing tumor cells, for example cytotoxic T lymphocytes, alpha/beta ($\alpha\beta$) T cells (preferably CD8+), $\gamma\delta$ T cells (e.g. particularly cells expressing a $\gamma\delta$, TCR heterodimer encoded by V$\gamma$9/V$\delta$2 genes), NK.T cells and/or NK cells. Non-limiting examples of said immunotherapeutic treatments include the administration of cytotoxic antibodies that bind a tumor antigen and induce death of a cell to which they are bound, particularly via ADCC mechanisms. Specific non-limiting examples of the latter group include any of the antibodies listed in Table 2 herein. Other non-limiting examples of said immunotherapeutic treatments include the administration of antibodies that increase the activity of cytotoxic T lymphocytes, alpha/beta ($\alpha\beta$) T cells (preferably CD8+), $\gamma\delta$ T cells (e.g. particularly cells expressing a $\gamma\delta$, TCR heterodimer encoded by V$\gamma$9/V$\delta$2 genes), NK.T cells and/or NK cells. Specific non-limiting examples of the latter group include any of the NK-potentiating disclosed in WO 05/009465 filed Jul. 23, 2004 or U.S. provisional application No. 60/489,489 filed Jul. 24, 2003, or TLR agonist compounds described in PCT/IB2005/000509, filed Feb. 8, 2005, titled "Composition and method for the treatment of carcinoma" or in U.S. Pat. Nos. 6,194,388; 6,008,200; 6,207,646; 6,239,116; and 6,429,199. The disclosures of each of the foregoing references are included herein by reference for the immunotherapeutic compounds disclosed therein.

The invention also provides a method of determining whether a tumor or tumor cell is amenable to treatment by a ligand of a 4Ig-B7-H3 polypeptide, for example a cytotoxic antibody or other ligand capable of inducing or enhancing the death or lysis of a cell which expresses a 4Ig-B7-H3 polypeptide.

Determining whether a cell or a tumor cell expresses 4Ig-B7-H3 can be carried out as described in the examples, e.g. by detecting the presence of one or more 4Ig-B7-H3 polypeptides in a biological sample from a cancer patient, generally from a tumor biopsy. For example, neuroblastoma, melanomas and carcinomas may express 4Ig-B7-H3 proteins and that these types of tumors, as well as others, can be treated with a 4Ig-B7-H3 ligand according to the invention.

In other specific embodiments, a diagostic assay is performed on a tumor sample from a patient to determine whether the tumor sample comprises 4Ig-B7-H3-expressing cells. Such assays are described herein; for example antibody-based immunohistochemistry assays can be used advantageously. Preferably a tumor biopsy is performed, yielding a biological sample. A determination that said biological sample comprises 4Ig-B7-H3 expressing cells indicates that the patient can benefit from the administration of a 4Ig-B7-H3 ligand. The patient is then treated with the 4Ig-B7-H3 ligand.

Preferably, the step of determining whether cancer cells in said subject express a 4Ig-B7-H3 polypeptide is performed on a tumoral sample derived from a patient. For example, the sample can be a biopsy of the patient's tumor, a cell or tissue culture, etc. Such sample can be obtained by conventional methods. In a particular embodiment, the sample is obtained by non-invasive methods and/or from tissue collections.

Therefore, in one embodiment of the methods and uses according to the present invention, the step of determining whether cancer cells in said subject express a 4Ig-B7-H3 receptor comprises : providing a tumoral sample from the patient and detecting the expression of a 4Ig-B7-H3 polypeptide. The expression of a 4Ig-B7-H3 polypeptide may be detected at the nucleic acid level or at the polypeptide level.

Various techniques known in the art may be used to detect or quantify 4Ig-B7-H3 expression, including sequencing, hybridisation, amplification and/or binding to specific ligands (such as antibodies). Suitable methods include Southern blot (for DNAs), Northern blot (for RNAs), fluorescent in situ hybridization (FISH), gel migration, ELISA, radio-immunoassays (RIA) and immuno-enzymatic assays (IEMA).

Some of these approaches are particularly suited for assessing a polypeptide sequence or expression level, such as Northern blot, ELISA and RIA. These latter require the use of a ligand specific for the polypeptide, more preferably of a specific antibody.

Different types of ligands may be used, such as specific antibodies. In a specific embodiment, the sample is contacted with an antibody specific for a 4Ig-B7-H3 polypeptide and the formation of an immune complex is determined. Various methods for detecting an immune complex can be used, such as ELISA, radioimmunoassays (RIA) and immuno-enzymatic assays (IEMA).

Within the context of this invention, an antibody designates a polyclonal antibody, a monoclonal antibody, as well as fragments or derivatives thereof having substantially the same antigen specificity. Fragments include Fab, Fab'2, CDR regions, etc. Derivatives include single-chain antibodies, humanized antibodies, poly-functional antibodies, etc. Any of the 4Ig-B7-H3-specific antibodies described herein are suitable for use.

In a specific embodiment, the method comprises contacting a sample from the subject with (a support coated with) an antibody specific for a 4Ig-B7-H3 polypeptide, and determining the presence of an immune complex.

In an alternative embodiment, the expression of a 4Ig-B7-H3 receptor in said cancer cell is determined using a 4Ig-B7-H3-specific nucleic acid primer or probe. Such primer or probes are designed to specifically hybridise with a 4Ig-B7-H3 nucleic acid, under suitable hybridisation conditions (for example under stringent conditions), thereby allowing detection of a gene or RNA coding for 4Ig-B7-H3. A particular embodiment comprises contacting a tumor sample from the patient with a 4Ig-B7-H3-specific primer or probe, and determining the existence of a hybrid or amplification product. The presence (or amount) of 4Ig-B7-H3 mRNA in a sample can provide an indication as to the expression of said receptor. Such determination may be accomplished by various techniques known in the art, including through RT-PCR. To that purpose, total RNA is isolated from cancer cells using commercially available kits, such as the RNeasy Mini kit (Qiagen, Valencia, Calif.). DNase I-treated total RNA (3 µg) is reverse-transcribed by using random primers with RNaseH-free reverse transcriptase (Invitrogen, San Diego, Calif.). 4Ig-B7-H3 can be amplified using specific primers described in the Examples.

Prior to determining expression of 4Ig-B7-H3, the sample may be treated to improve availability of 4Ig-B7-H3 nucleic acids or polypeptides. Such treatment may include, for instance, a lysis of the cells or tissue (e.g., mechanical, enzymatic or physical).

The invention also relates to a diagnostic kit comprising products and reagents for detecting in a tumoral sample from a subject the expression of a 4Ig-B7-H3 gene or polypeptide. Said diagnostic kit according to the present invention comprises any primer, any pair of primers, any nucleic acid probe and/or any ligand, preferably antibody, described in the present invention. Said diagnostic kit according to the present invention can further comprise reagents and/or protocols for performing a hybridization, amplification or antigen-antibody immune reaction.

Further Aspects

In further aspects, the invention provides a method of inhibiting NK cell activity comprising bringing an NK cell into contact with a 4Ig-B7-H3 polypeptide. Also provided is a method of identifying an NK cell activity comprising bringing an NK cell into contact with a 4Ig-B7-H3 polypeptide and detecting binding of the polypeptide to the NK cell. Preferably such a 4Ig-B7-H3 protein comprises, consists essentially of, or consists of the amino acid sequence shown in SEQ ID NO 2, or a portion thereof. In another aspect the invention provides a method for rendering a target cell sensitive to lysis by an NK cell, the method comprising bringing said target cell into contact with a compound capable of selectively inhibiting the activity of, or decreasing the expression, preferably cell surface expression, of a 4Ig-B7-H3 protein on the target cell; preferably the compound inhibits the expression of the 4Ig-B7-H3 gene, inhibits translation of 4Ig-B7-H3 RNA, inhibits 4Ig-B7-H3 cell surface expression or inhibits functioning, especially ligand binding, or the 4Ig-B7-H3 protein. In related embodiments, the invention provides methods of screening of identifying compounds for the treatment of disease, the method comprising determining whether a candidate compound capable of selectively inhibiting the activity of, or decreasing the expression, preferably cell surface expression, of a 4Ig-B7-H3 protein on the target cell, or preferably whether the compound inhibits the expression of the 4Ig-B7-H3 gene, inhibits translation of 4Ig-B7-H3 RNA, inhibits 4Ig-B7-H3 cell surface expression or inhibits functioning, especially ligand binding, or the 4Ig-B7-H3 protein, wherein a positive determination that the compound has any of said activities identifies the candidate compound as a compound suitable for the treatment of disease (e.g. a tumor).

In another aspect, the present invention provides antibodies produced using any of the herein-described methods. The invention also encompasses fragments and derivatives of the antibodies having substantially the same antigen specificity and activity (e.g., which can bind to the same antigens as the parent antibody). Such fragments include, without limitation, Fab fragments, Fab'2 fragments, CDR and ScFv.

In another embodiment, any of the aforementioned method involving an antibody that binds a 4Ig-B7-H3 polypeptide may be carried out with antibodies 5B14 or 7-517, or with antibodies that compete with them. Thus, in one embodiment, the invention encompasses use according to any of the methods herein, of an antibody that competes with monoclonal antibodies 5B14 or 7-517. Optionally an antibody which competes with antibody 5B14 or 7-517 is not antibody 5B 14 or 7-517 itself, respectively. Preferably said antibodies are chimeric antibodies, humanized antibodies, or human antibodies.

The term "competes with" when referring to a particular monoclonal antibody (e.g. 5B14 or 7-517) means that an antibody competes with the monoclonal antibody (e.g. 5B14 or 7-517) in a binding assay using either recombinant 4Ig-B7-H3 molecules or surface expressed 4Ig-B7-H3 molecules. For example, if an antibody reduces binding of 5B14 or 7-517 to a 4Ig-B7-H3 molecule in a binding assay, the antibody "competes" with 5B14 or 7-517. An antibody that "competes" with 5B14 or 7-517 may compete with 5B14 or 7-517 for binding to the human 4Ig-B7-H3 molecule.

In another embodiment, the invention comprises an antibody that binds a 4Ig-B7-H3 polypeptide, wherein the antibody is 5B14 or 7-517. Also encompassed is a host cell, particularly a hybridoma which produces any of the aforementioned antibodies.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to 4Ig-B7-H3 antigen epitopes. Additionally, it is proposed that monoclonal antibodies specific to the particular 4Ig-B7-H3 of different species may be utilized in other useful applications In general, both polyclonal and monoclonal antibodies against 4Ig-B7-H3 may be used in a variety of embodiments. For example, they may be employed in antibody cloning protocols to obtain cDNAs or genes encoding other 4Ig-B7-H3. They may also be used in inhibition studies to analyze the effects of 4Ig-B7-H3-related peptides, especially a 4Ig-B7-H3 receptor found on NK cells, in cells or animals. 4Ig-B7-H3 antibodies will also be useful in immunolocalization studies to analyze the distribution of 4Ig-B7-H3 during various cellular events, for example, to determine the cellular or tissue-specific distribution of 4Ig-B7-H3 polypeptides at different points in tumor progression. A particularly useful application of such antibodies is in purifying native or recombinant 4Ig-B7-H3, for example, using an antibody affinity column, eg. in order to co-precipitate a 4Ig-B7-H3 receptor from a biological sample derived from NK cells. The operation of such immunological techniques will be known to those of skill in the art in light of the present disclosure.

In another aspect, the present invention provides kits comprising any one or more of the herein-described antibodies. One embodiment, the kit comprises at least one diagnostic antibody and at least one therapeutic (e.g., cytotoxic) antibody. In another embodiment, the diagnostic antibody and the therapeutic antibody specifically bind to the same NK cell receptor. In another embodiment, the kit also comprises instructions for using the antibodies according to the present methods.

The invention also comprises pharmaceutical compositions comprising one or more of the present antibodies, or a fragment or derivative thereof, and a pharmaceutically acceptable carrier or excipient.

DESCRIPTION OF THE FIGURES

FIG. 4: Biochemical characterization of the 5B14-reactive molecule and cytofluorimetric analysis of cell transfectants. Panel A: 293T and ACN cell lines were surface labeled with 125I and immunoprecipitated with the 5B 14 mAb. Samples, either untreated (−) or treated (+) with N-glycosidase F, were analyzed in an 8% SDS-PAGE under reducing conditions. Molecular weight markers (kD) are indicated. Panel B: CHO-K cells either untransfected or transfected with the 4Ig-B7-H3 cDNA were stained with 5B14 mAb followed by PE-conjugated goat anti-mouse isotype specific second reagent and analyzed by flow cytometry. White profiles indicate cells incubated with the second reagent only.

FIG. 7: Shows Table 1, Surface reactivity of the 5B14 mAb on different cell types. Normal cells and in vitro cultured cell lines of different histotype were analyzed by indirect immunofluorescence and FACS analysis for reactivity with the 5B 14 and anti-GD2 mAbs. Mean Fluorescence Intensity (MFS): overlapping the negative control (−)(MFI set on 5); MFI below 20 (+/−); MFI between 20 and 100 (+); MFI over 100 (++).

FIG. 8: Domain structure of 4-Ig-B7-H3 as described in Steinberger et al, (2004).

DETAILED DESCRIPTION OF THE INVENTION

Introduction

Figure 1:
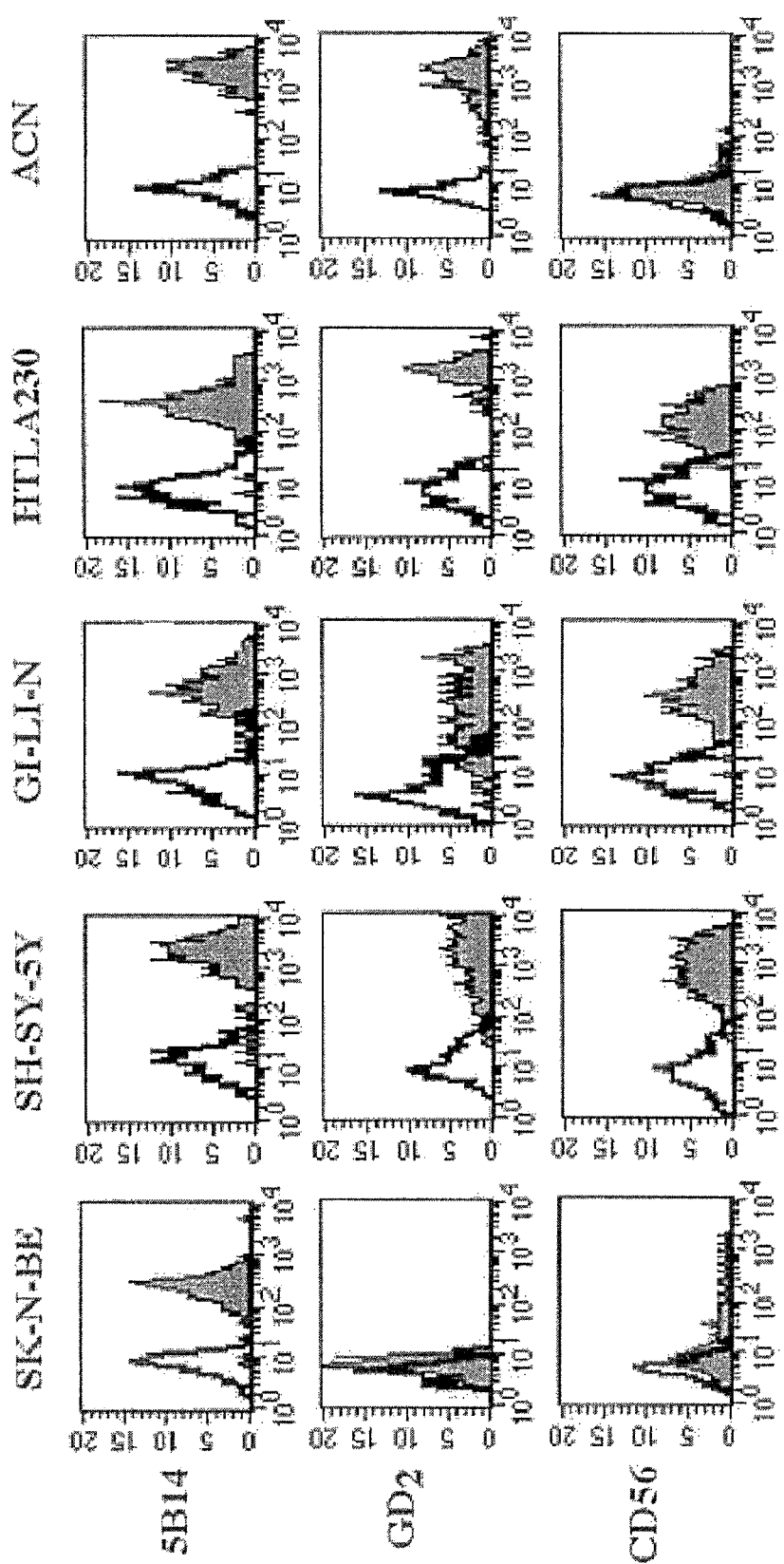
FIG. 1: Reactivity of the 5B14 mAb with neuroblastoma cell lines. Different neuroblastoma cell lines were stained with 5B14 mAb or mAbs to the indicated molecules followed by PE-conjugated goat anti-mouse isotype-specific second reagent and analyzed by flow cytometry. White profiles indicate cells incubated with the second reagent only.

The present invention provides novel methods for producing and using antibodies suitable for the diagnosis and treatment of proliferative disorders, particularly tumors, inflammatory disorders and immunoproliferative disorders. Antibodies, antibody derivatives, or antibody fragments produced using the herein described methods are encompassed, as are methods of diagnosing and treating patients using the antibodies. In particular, the invention provides compounds that facilitate the activation of human NK cells; these compounds act by blocking interactions of the 4Ig-B7-H3 protein with the inhibitory 4Ig-B7-H3 receptor (4Ig-B7-H3R) on NK cells and neutralizes the receptor's inhibitory signals, resulting in potentiation of NK cell cytotoxicity in NK cells expressing 4Ig-B7-H3R. This potentiation of NK cell activity has a wide range of therapeutic applications. Potentiation of NK cells can be beneficial for the treatment of proliferative disorders such as tumors as well as infectious disease and inflammatory disorders. Potentiation of NK cells has also been demonstrated to result in increased efficacy of therapeutic antibodies, particularly antibodies capable of inducing ADCC-mediated cell killing of a target cell to which they are bound (for example antibodies which bind tumors antigens). A range of such therapeutic antibodies arc further discussed herein.

Additionally, based on the discovery that the 4Ig-B7-H3 protein is selectively expressed on overproliferating cells (e.g. tumor or immune cells), the present invention provides a method of treating disorders characterized by such overproliferating cells by specifically targeting those cells that express 4Ig-B7-H3—preferably using cytotoxic antibodies. In this way, the number of overproliferating cells is specifically reduced, while sparing other immune and non-immune cells. The compound that targets the cells expression 4Ig-B7-H3 can act via any suitable mechanism, e.g., neutralizing the protective effect of the 4Ig-B7-H3 protein to the proliferating cell, by targeting proliferating cells for destruction by the immune system (e.g. via antibody-dependent cytotoxicity, also referred to as ADCC), or, by killing the cells directly by contacting them with a cytotoxic agent such as a radioisotope, toxin, or drug. Additionally, based on the same discovery, the invention also provides methods of diagnosis of disease, as detection of 4Ig-B7-H3 can be used as diagnostic tool to identify proliferating cells (e.g. tumors, immunoproliferative disorders). Generally, the present methods relating to targeting 4Ig-B7-H3-expressing cells involve the use of monoclonal antibodies specific for 4Ig-B7-H3. Advantageously, two sets of antibodies are used. One set, comprising directly or indirectly labeled antibodies, are diagnostic in nature and used to determine whether 4Ig-B7-H3 is expressed on cells (e.g. tumor cells) from a patient. The second set, used for treatment, corresponds to monoclonal antibodies that are generally raised in a non-human animal but which have been rendered suitable for use in humans, e.g., are humanized or chimerized. In certain embodiments, the antibodies are further derivatized with cytotoxic agents, directly or indirectly, so that they kill cells expressing 4Ig-B7-H3. For example, the antibodies can be linked to radioactive isotopes, cytotoxic polypeptides, or cytotoxic small molecules.

Definitions

As used herein, the following terms have the meanings ascribed to them unless specified otherwise.

As used herein, "NK" cells refers to a sub-population of lymphocytes that are involved in non-conventional immunity. NK cells can be identified by virtue of certain characteristics and biological properties, such as the expression of specific surface antigens including CD16, CD56 and/or CD57, the absence of the alpha/beta or gamma/delta TCR complex on the cell surface, the ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response. Any of these characteristics and activities can be used to identify NK cells, using methods well known in the art.

As used here, "4Ig-B7-H3 status" refers to the identity and prominence of the 4Ig-B7-H3 protein expressed on proliferating or other cells (e.g. tumor cells, dendritic cells, proliferating immune cells, etc.) taken from an individual, e.g., a cancer patient. For example, an examination of cells taken from a patient may find that 4Ig-B7-H3 is expressed in 30%, 40%, 50%, etc., of the cells. "Prominently expressed" refers to the 4Ig-B7-H3 protein that is expressed in a substantial number of overproliferating or tumor cells taken from a given patient. While the definition of the term "prominently expressed" is not bound by a precise percentage value, in most cases a protein said to be "prominently expressed" will be present on at least 20%, 30%, 40%, preferably 50%, 60%, 70%, or more of the neuroblastoma, melanoma, carcinoma or other overproliferating cells taken from a patient.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG and/or IgM are the preferred classes of antibodies employed in this invention, with IgG being particularly preferred, because they are the most common antibodies in the physiological situation and because they are most easily made in a laboratory setting. Preferably the antibody of this invention is a monoclonal antibody. Particularly preferred are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g. 4Ig-B7-H3 protein or a 4Ig-B7-H3 receptor, as assessed using either recombinant forms of the proteins, epitopes therein, or native proteins present on the surface of isolated NK or relevant target cells. Competitive binding assays and other methods for determining specific binding are further described below and are well known in the art.

A "human-suitable" antibody refers to any antibody, derivatized antibody, or antibody fragment that can be safely used in humans for, e.g. the therapeutic methods described herein. Human-suitable antibodies include all types of humanized, chimeric, or fully human antibodies, or any antibodies in which at least a portion of the antibodies is derived from humans or otherwise modified so as to avoid the immune response that is generally provoked when native non-human antibodies are used.

"Toxic" or "cytotoxic" peptides or small molecules encompass any compound that can slow down, halt, or reverse the proliferation of cells, decrease their activity (e.g., the cytolytic activity of NK cells) in any detectable way, or directly or indirectly kill them. Toxic or cytotoxic compounds can work for example by killing the cells by inducing ADCC, provoking apoptosis or otherwise. As used herein, a toxic "peptide" can include any peptide, polypeptide, or derivative of such, including peptide- or polypeptide-derivatives with unnatural amino acids or modified linkages. A toxic "small molecule" can include any toxic compound or element, preferably with a size of less than 10 kD, 5 kD, 1 kD, 750 D, 600 D, 500 D, 400 D, 300 D, or smaller.

By "immunogenic fragment", it is herein meant any polypeptidic or peptidic fragment which is capable of eliciting an immune response such as (i) the generation of antibodies binding said fragment and/or binding any form of the molecule comprising said fragment, including the membrane-bound receptor and mutants derived therefrom, (ii) the stimulation of a T-cell response involving T-cells reacting to the bi-molecular complex comprising any MHC molecule and a peptide derived from said fragment, (iii) the binding of transfected vehicles such as bacteriophages or bacteria expressing genes encoding mammalian immunoglobulins. Alternatively, an immunogenic fragment also refers to any construction capable of eliciting an immune response as defined above, such as a peptidic fragment conjugated to a carrier protein by covalent coupling, a chimeric recombinant polypeptide construct comprising said peptidic fragment in its amino acid sequence, and specifically includes cells transfected with a cDNA of which sequence comprises a portion encoding said fragment.

For the purposes of the present invention, a "humanized" antibody refers to an antibody in which the constant and variable framework region of one or more human immunoglobulins is fused with the binding region, e.g. the CDR, of an animal immunoglobulin. Such humanized antibodies are designed to maintain the binding specificity of the non-human antibody from which the binding regions are derived, but to avoid an immune reaction against the non-human antibody.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "human" antibody is an antibody obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference). A human antibody can also be obtained by determining the sequence of an antibody isolated from a human and expressing a nucleotide sequence encoding said antibody from a recombinant host cell in cell culture.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The term "biological sample" as used herein includes but is not limited to a biological fluid (for example serum, lymph, blood), cell sample or tissue sample (for example bone marrow).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

As used herein, the term "hybridizes under stringent conditions" describes conditions for hybridization and washing under which nucleotide sequences at least 30% (preferably, 35%, 40%, 45%, 50%, 55%, 60%, 65%, 70%, 75%, 80%, 85%, 90%, 95% or 98%) identical to each other typically remain hybridized to each other. Such stringent conditions are known to those skilled in the art and can be found in Current Protocols in Molecular Biology, John Wiley & Sons, N.Y. (1989). In one, non-limiting example stringent hybridization conditions are hybridization at 6×sodium chloride/sodium citrate (SSQ at about 45° C., followed by one or more washes in 0.1×SSC, 0.2% SDS at about 68° C. In a preferred, non-limiting example stringent hybridization conditions are hybridization in 6×SSC at about 45° C., followed by one or more washes in 0.2×SSC, 0.1% SDS at 50-65° C. (i.e., one or more washes at 50° C., 55° C., 60° C. or 65° C.). It is understood that the nucleic acids of the invention do not include nucleic acid molecules that hybridize under these conditions solely to a nucleotide sequence consisting of only A or T nucleotides. In a particular embodiment, typical stringent hybridisation conditions include temperatures above 30° C., preferably above 35° C., more preferably in excess of 42° C., and/or salinity of less than about 500 mM, preferably less than 200 mM. Hybridization conditions may be adjusted by the skilled person by modifying the temperature, salinity and/or the concentration of other reagents such as SDS, SSC, etc.

Producing Monoclonal Antibodies Specific for 4Ig-B7-H3

The present invention involves the production and use of antibodies, antibody fragments, or antibody derivatives that are suitable for use in humans and that target the 4Ig-B7-H3 protein or the 4Ig-B7-H3R protein. The antibodies of this invention may be produced by any of a variety of techniques known in the art. Typically, they are produced by immunization of a non-human animal, preferably a mouse, with an immunogen comprising a 4Ig-B7-H3 or 4Ig-B7-H3R protein present on the surface of NK cells or target cells. The receptor may comprise entire 4Ig-B7-H3R-expressing NK cells, or 4Ig-B7-1l3 expressing target cells (e.g. neuroblastoma, melanoma, carcinoma, mature or immature dendritic cells), or cell membranes, the full length sequence of 4Ig-B7-H3 or 4Ig-B7-H3R, or a fragment or derivative thereof, typically an immunogenic fragment, i.e., a portion of the polypeptide comprising an epitope exposed on the surface of cells expressing 4Ig-B7-H3 or 4Ig-B7-H3R. Such fragments typically contain at least 7 consecutive amino acids of the mature polypeptide sequence, even more preferably at least 10 consecutive amino acids thereof. They are essentially derived from the extracellular domain of the 4Ig-B7-H3 or 4Ig-B7-H3R protein.

In preferred embodiments, the 4Ig-B7-H3 or 4Ig-B7-H3R protein or peptide used to generate antibodies is a human 4Ig-B7-H3 or 4Ig-B7-H3R protein or peptide.

In a most preferred embodiment, the immunogen comprises a wild-type human 4Ig-B7-H3 or 4Ig-B7-H3R polypeptide in a lipid membrane, typically at the surface of a cell. In a specific embodiment, the immunogen comprises intact NK or target cells, particularly intact human NK or target cells, optionally treated or lysed. The 4-Ig-B7-H3 protein and cDNA sequence and the protein structure are described in Steinberger et al. (2004) J. Immunol. 172:2352-2359 and in FIGS. 8 and 9 herein.

In one embodiment, the antibodies are derived from one or more already-existing monoclonal antibodies that recognize 4Ig-B7-H3 or 4Ig-B7-H3R, e.g. 5B14 or 7-517 latter see, e.g., Steinberger et al. (2004) J. Immunol. 172:2352-2359). Such antibodies can be directly or indirectly labeled (i.e., used with a labeled secondary antibody) for use as diagnostic antibodies for the herein-described typing step to determine the 4Ig-B7-H3 status of patients. In addition, the antibodies can be made suitable for human administration and, optionally, made toxic as described herein for use as cytotoxic antibodies in the present therapeutic methods.

The present diagnostic or therapeutic (e.g. cytotoxic) antibodies can be full length antibodies or antibody fragments or derivatives. Examples of antibody fragments include Fab, Fab', Fab'-SH, F(ab')$_2$, and Fv fragments; diabodies; single-chain Fv (scFv) molecules; single chain polypeptides containing only one light chain variable domain, or a fragment thereof that contains the three CDRs of the light chain variable domain, without an associated heavy chain moiety; single chain polypeptides containing only one heavy chain variable region, or a fragment thereof containing the three CDRs of the heavy chain variable region, without an associated light chain moiety; and multispecific antibodies formed from antibody fragments. Such fragments and derivatives and methods of preparing them are well known in the art. For example, pepsin can be used to digest an antibody below the disulfide linkages in the hinge region to produce F(ab)'2, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993)). While various antibody fragments are defined in terms of the digestion of an intact antibody, one of skill will appreciate that such fragments may be synthesized de novo either chemically or by using recombinant DNA methodology.

The preparation of monoclonal or polyclonal antibodies is well known in the art, and any of a large number of available techniques can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy (1985)). Techniques for the production of single chain antibodies (U.S. Pat. No. 4,946,778) can be adapted to produce antibodies to desired polypeptides. Also, transgenic mice, or other organisms such as other mammals, may be used to express humanized, chimeric, or similarly-modified antibodies. Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). In one embodiment, the method comprises selecting, from a library or repertoire, a monoclonal antibody or a fragment or derivative thereof that cross reacts with at least one NK receptor. For example, the repertoire may be any (recombinant) repertoire of antibodies or fragments thereof, optionally displayed by any suitable structure (e.g., phage, bacteria, synthetic complex, etc.).

The step of immunizing a non-human mammal with an antigen may be carried out in any manner well known in the art for (see, for example, E. Harlow and D. Lane, *Antibodies: A Laboratory Manual.*, Cold Spring Harbor Laboratory Press, Cold Spring Harbor, N.Y. (1988)). Generally, the immunogen is suspended or dissolved in a buffer, optionally with an adjuvant, such as complete Freund's adjuvant. Methods for determining the amount of immunogen, types of buffers and amounts of adjuvant are well known to those of skill in the art and are not limiting in any way on the present invention.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be utilized as long as they result in the production of B cells expressing an antibody directed to the antigen used in immunization.

In another embodiment, lymphocytes from an unimmunized non-human mammal are isolated, grown in vitro, and then exposed to the immunogen in cell culture. The lymphocytes arc then harvested and the fusion step described below is carried out.

For monoclonal antibodies, which are preferred for the purposes of the present invention, the next step is the isolation of cells, e.g., lymphocytes, splenocytes, or B cells, from the immunized non-human mammal and the subsequent fusion of those splenocytes, or B cells, or lymphocytes, with an immortalized cell in order to form an antibody-producing hybridoma. Accordingly, the term "preparing antibodies from an immunized animal," as used herein, includes obtaining B-cells/splenocytes/lymphocytes from an immunized animal and using those cells to produce a hybridoma that expresses antibodies, as well as obtaining antibodies directly from the serum of an immunized animal. The isolation of splenocytes, e.g., from a non-human mammal is well-known in the art and, e.g., involves removing the spleen from an anesthetized non-human mammal, cutting it into small pieces and squeezing the splenocytes from the splenic capsule and through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the antibody-producing cells are fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors available from the Salk Institute Cell Distribution Center, San Diego, Calif. U.S.A., X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

The hybridomas can be grown on a feeder layer of macrophages. The macrophages are preferably from littermates of the non-human mammal used to isolate splenocytes and are typically primed with incomplete Freund's adjuvant or the like several days before plating the hybridomas. Fusion methods are described, e.g., in (Goding, "Monoclonal Antibodies: Principles and Practice," pp. 59-103 (Academic Press, 1986)), the disclosure of which is herein incorporated by reference.

The cells are allowed to grow in the selection media for sufficient time for colony formation and antibody production. This is usually between 7 and 14 days. The hybridoma colonies are then assayed for the production of antibodies that specifically recognize the desired substrate, e.g. a 4Ig-B7-H3 or 4Ig-B7-H3R protein. The assay is typically a colorimetric ELISA-type assay, although any assay may be employed that can be adapted to the wells that the hybridomas are grown in. Other assays include immunoprecipitation and radioimmunoassay. The wells positive for the desired antibody production are examined to determine if one or more distinct colonies are present. If more than one colony is present, the cells may be re-cloned and grown to ensure that only a single cell has given rise to the colony producing the desired antibody. Positive wells with a single apparent colony are typically recloned and re-assayed to ensure that only one monoclonal antibody is being detected and produced.

Hybridomas that are confirmed to be producing a monoclonal antibody of this invention are then grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Amersham Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

In preferred embodiments, the DNA encoding an antibody that binds a determinant present on 4Ig-B7-H3 or 4Ig-B7-H3R is isolated from the hybridoma, placed in an appropriate expression vector for transfection into an appropriate host. The host is then used for the recombinant production of the antibody, variants thereof, active fragments thereof, or humanized or chimeric antibodies comprising the antigen recognition portion of the antibody.

DNA encoding the monoclonal antibodies of the invention can be readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant expression in bacteria of DNA encoding the antibody is well known in the art (see, for example, Skerra et al. (1993) Curr. Op. Immunol. 5:256; and Pluckthun (1992) Immunol. Revs. 130:151. Antibodies may also be produced by selection of combinatorial libraries of immunoglobulins, as disclosed for instance in Ward et al. (1989) Nature 341:544.

In a specific embodiment, the antibody binds essentially the same epitope or determinant as one of the monoclonal antibodies 5B14 or 7-517 (for the latter see, e.g., Steinberger et al. (2004) J. Immunol. 172:2352-2359, the entire disclosure of which is herein incorporated by reference). The term "binds to substantially the same epitope or determinant as" the monoclonal antibody x means that an antibody "can compete" with x, where x is 5B14, etc. The identification of one or more antibodies that bind(s) to substantially the same epitope as the monoclonal antibody in question can be readily determined using any one of a variety of immunological screening assays in which antibody competition can be assessed. Such assays are routine in the art (see, e.g., U.S. Pat. No. 5,660,827, which is herein incorporated by reference). It will be understood that actually determining the epitope to which the antibody binds is not in any way required to identify an antibody that binds to the same or substantially the same epitope as the monoclonal antibody in question.

For example, where the test antibodies to be examined are obtained from different source animals, or are even of a different Ig isotype, a simple competition assay may be employed in which the control (e.g. 5B14) and test antibodies are admixed (or pre-adsorbed) and applied to a sample containing the epitope-containing protein, e.g. 4Ig-B7-H3 in the case of 5B 14. Protocols based upon ELISAs, radioimmunoassays, Western blotting and the use of BIACORE (as described, e.g., in the examples section) are suitable for use in such simple competition studies and are well known in the art.

In certain embodiments, one would pre-mix the control antibodies (e.g. 5B14) with varying amounts of the test antibodies (e.g., 1:10 or 1:100) for a period of time prior to applying to the antigen (e.g. 4Ig-B7-H3 epitope) containing sample. In other embodiments, the control and varying amounts of test antibodies can simply be admixed during exposure to the antigen sample. As long as one can distinguish bound from free antibodies (e.g., by using separation or washing techniques to eliminate unbound antibodies) and the control antibody from the test antibodies (e.g., by using species- or isotype-specific secondary antibodies or by specifically labeling the control antibody with a detectable label) one will be able to determine if the test antibodies reduce the binding of the control antibody to the antigen, indicating that the test antibody recognizes substantially the same epitope as the control. The binding of the (labeled) control antibodies in the absence of a completely irrelevant antibody would be the control high value. The control low value would be obtained by incubating the labeled control antibodies 5B14) with unlabeled antibodies of exactly the same type (e.g. 5B14), where competition would occur and reduce binding of the labeled antibodies. In a test assay, a significant reduction in labeled antibody reactivity in the presence of a test antibody is indicative of a test antibody that recognizes the same epitope, i.e., one that "cross-reacts" with the labeled control antibody. Any test antibody that reduces the binding of the labeled control to each antigen by at least 50% or more preferably 70%, at any ratio of control:test antibody between about 1:10 and about 1:100 is considered to be an antibody that binds to substantially the same epitope or determinant as the control, Preferably, such test antibody will reduce the binding of the control to the antigen by at least 90%.

In one embodiment, competition can be assessed by a flow cytometry test. Cells bearing a given activating receptor are incubated first with a control antibody that is known to specifically bind to the receptor (e.g., NK cells expressing 4Ig-B7-H3, and the 5B14 antibody), and then with the test antibody that has been labeled with, e.g., a fluorochrome or biotin. The test antibody is said to compete with the control if the binding obtained with preincubation with saturating amounts of control antibody is 80%, preferably, 50, 40 or less of the binding (mean of fluorescence) obtained by the antibody without preincubation with the control. Alternatively, a test antibody is said to compete with the control if the binding obtained with a labeled control (by a fluorochrome or biotin) on cells preincubated with saturating amount of antibody to test is 80%, preferably 50%, 40%, or less of the binding obtained without preincubation with the antibody.

In one preferred example, a simple competition assay may be employed in which a test antibody is pre-adsorbed and applied at saturating concentration to a surface onto which is immobilized the substrate for the antibody binding, e.g. the 4Ig-B7-H3 protein, or epitope-containing portion thereof, which is known to be bound by 5B 14. The surface is preferably a BIACORE chip. The control antibody (e.g. 5B14) is then brought into contact with the surface at a substrate-saturating concentration and the substrate surface binding of the control antibody is measured. This binding of the control antibody is compared with the binding of the control antibody to the substrate-containing surface in the absence of test antibody. In a test assay, a significant reduction in binding of the substrate-containing surface by the control antibody in the presence of a test antibody is indicative of a test antibody that recognizes the same epitope, i.e., one that "cross-reacts" with the control antibody. Any test antibody that reduces the binding of the control antibody to the antigen-containing substrate by at least 30% or more preferably 40% is considered to be an antibody that binds to substantially the same epitope or determinant as the control antibody. Preferably, such test antibody will reduce the binding of the control antibody to the substrate by at least 50%. It will be appreciated that the order of control and test antibodies can be reversed, that is the control antibody is first bound to the surface and the test antibody is brought into contact with the surface thereafter. Preferably, the antibody having higher affinity for the substrate antigens is bound to the substrate-containing surface first since it will be expected that the decrease in binding seen for the second antibody (assuming the antibodies are cross-reacting) will be of greater magnitude. Further examples of such assays are provided in the Examples and in Saunal. et al. (1995) J. Immunol. Meth 183: 33-41, the disclosure of which is incorporated herein by reference.

In one embodiment, anti-4Ig-B7-H3 antibodies are capable of interacting with multiple proteins of the B7 family, that is, are capable of interacting with 4Ig-B7-H3 and at least one other protein of the B7 family, particularly if it is ensured that such antibodies do not show excessive cross-reactivity with other, unrelated proteins. Similarly, anti-4Ig-B7-H3R antibodies are capable of interacting with multiple receptors of proteins of the B7 family, that is, are capable of interacting with 4Ig-B7-H3R and at least one other receptor of a protein of the B7 family.

Preferably, the anti-4Ig-B7-H3 or anti-4Ig-B7-H3R antibodies do not show excessive cross-reactivity with other, unrelated proteins. Preferably, monoclonal antibodies that recognize an epitope from 4Ig-B7-H3 or 4Ig-B7-H3R will react with an epitope that is present on a substantial percentage of target or NK cells, respectively, especially in patients (e.g. having a proliferative disorder, tumor, inflammatory disorder, etc), but will not significantly react with $CD20^+$ B cells, or with other immune or non-immune cells. Preferably the anti-4Ig-B7-H3 or anti-4Ig-B7-H3R antibodies will not significantly react with other proteins of the B7 family or the receptors therefore, respectively. Other proteins of the B7 family include for example B7-1 (CD80), B7-2 (CD86), B7-H2 (ICOS-L), B7-H1 (PD-L1), B7-DC (PD-L2, B7-H4 (B7S1, B7x) and BT3). Receptors for other proteins of the B7 family include but are not limited to CD28, ICOS or CTLA-4, PD-1 and BTLA, mainly expressed on T cells. In preferred embodiments, the antibody will also be nonreactive with monocytes, granulocytes, platelets, and red blood cells. In preferred embodiments, the antibodies will only recognize a single receptor for the 4Ig-B7-H3 protein, thereby restricting as much as possible the effects of the therapeutic (e.g., cytotoxic) antibodies to the overproliferating cells underlying the disorder.

Once an antibody that specifically recognizes 4Ig-B7-H3 or 4Ig-B7-H3R is identified, it can be tested for its ability to bind to target cells (e.g. proliferating cells, tumors cells, dendritic cells) or NK cells, respectively. Target cells may be taken from patients with proliferative disorders such as neuroblastoma, melanoma or carcinoma, for example.

An antibody that specifically recognizes 4Ig-B7-H3 may be validated in an immunoassay to test its ability to bind to target cells taken from patients with a disorder, for example, a proliferative disorder. For example, a tumor biopsy is performed and cells are taken from a plurality of patients, e.g. a needle biopsy or bone marrow aspirate in the case of suspected neuroblastoma. The ability of a given antibody to bind to the target cells is then assessed using standard methods well known to those in the art. Antibodies that are found to bind to a substantial proportion of target cells (e.g., 20%, 30%, 40%, 50%, 60%, 70%, 80% or more) from a significant percentage of patients (e.g., 5%, 10%, 20%, 30%, 40%, 50% or more) are suitable for use in the present invention, both for diagnostic purposes during the 4Ig-B7-H3 status typing step described herein, or for use in the herein-described therapeutic methods, e.g., for derivitization to form human-suitable, cytotoxic antibodies. However, it will be appreciated that an antibody which binds less than said proportion of target cells may still be used advantageously, for example. to eliminate or prevent the possibility of escape of tumor cells from NK cell lysis. To assess the binding of the antibodies to the cells, the antibodies can either be directly or indirectly labeled. When indirectly labeled, a secondary, labeled antibody is typically added. The binding of the antibodies to the cells can then be detected using, e.g., cytofluorometric analysis (e.g. FACScan). See, e.g., Zambello et al. (2003) Blood 102:1797 or any other standard method.

NK Potentiating Antibodies

In the case of NK potentiating antibodies, the anti-4Ig-B7-H3 and anti-4Ig-B7-H3 antibodies of this invention are able to neutralize the 4Ig-B7-H3R-mediated inhibition of NK cell cytotoxicity. These antibodies are thus "neutralizing" or "inhibitory" antibodies, in the sense that they block, at least partially and detectably, the inhibitory signaling pathway mediated by a 4Ig-B7-H3R when it interacts with 4Ig-B7-H3 molecule. Inhibition of 4Ig-B7-H3 or 4Ig-B7-H3R-mediated inhibition of NK cell cytotoxicity can be assessed by various assays or tests, such as binding or cellular assays.

Once an antibody that binds 4Ig-B7-H3 or 4Ig-B7-H3R is identified, it can be tested for its ability to neutralize the inhibitory effect of the 4Ig-B7-H3R in intact NK cells. In a specific embodiment, the neutralizing activity can be illustrated by the capacity of said antibody to reconstitute lysis by 4Ig-B7-H3R-positive NK clones of 4Ig-B7-H3 positive target cells. In another specific embodiment, the neutralizing activity of the antibody is defined by the ability of the antibody to inhibit the binding of 4Ig-B7-H3 molecules to 4Ig-B7-H3R. In one embodiment, the inhibitory activity of an antibody of this invention can be assessed in a cell based cytotoxicity assay, as disclosed herein.

In another variant, the inhibitory activity of an antibody of this invention can be assessed in a cytokine-release assay, wherein NK cells are incubated with the test antibody and a target cell line expressing 4Ig-B7-H3 recognized by a 4Ig-B7-H3R molecule of the NK population, to stimulate NK cell cytokine production (for example IFN-γ and/or GM-CSF production). In an exemplary protocol, IFN-γ production from PBMC is assessed by cell surface and intracytoplasmic staining and analysis by flow cytometry after about 4 days in culture. Briefly, Brefeldin A (Sigma Aldrich) can be added at a final concentration of about 5 μg/ml for the least about 4 hours of culture. The cells can then incubated with anti-CD3 and anti-CD56 mAb prior to permeabilization (IntraPrep™; Beckman Coulter) and staining with PE-anti-IFN-γ or PE-IgG1 (Pharmingen). GM-CSF and IFN-γ production from polyclonal activated NK cells can be measured in supernatants using ELISA (GM-CSF: DuoSet Elisa, R&D Systems, Minneapolis, Minn.; IFN-γ: OptE1A set, Pharmingen).

Antibodies of this invention may partially or fully neutralize the 4Ig-B7-H3R-mediated inhibition of NK cell cytotoxicity. The term "neutralize 4Ig-B7-H3R-mediated inhibition of NK cell cytotoxicity," as used herein means the ability to increase to at least about 20%, preferably to at least about 30%, at least about 40%, at least about 50% or more (e.g., about 25-100%) of specific lysis obtained at the same effector:target cell ratio with NK cells or NK cell lines that are not blocked by their 4Ig-B7-H3R, as measured by a classical chromium release test of cytotoxicity, compared with the level of specific lysis obtained without antibody when an NK cell population expressing a 4Ig-B7-H3R is put in contact with a target cell expressing the cognate 4Ig-B7-H3 molecule (recognized by the 4Ig-B7-H3R expressed on NK cell). For example, preferred antibodies of this invention are able to induce the lysis of target cell populations (whether matched or HLA compatible or not, or autologous) expressing 4Ig-B7-H3R, i.e., cell populations that would not be effectively lysed by NK cells in the absence of said antibody. Accordingly, the antibodies of this invention may also be defined as facilitating NK cell activity in vivo.

Upon immunization and production of antibodies in a vertebrate or cell, particular selection steps may be performed to isolate antibodies as claimed. In this regard, in a specific embodiment, the invention also relates to methods of producing such antibodies, comprising:

a) immunizing a non-human mammal with an immunogen comprising an 4Ig-B7-H3 or 4Ig-B7-H3R polypeptide, or a fragment thereof, or a cell expressing any of the foregoing;

b) preparing antibodies from said immunized animal, wherein said antibodies bind a 4Ig-B7-H3 or 4Ig-B7-H3R polypeptide, c) selecting antibodies of (b) that are (i) capable of neutralizing inhibition of NK cell cytotoxicity on a population of NK cells expressing said 4Ig-B7-H3R polypeptide, or (ii) capable of neutralizing inhibition of NK cell cytotoxicity towards target cells expressing 4Ig-B7-H3.

In a preferred embodiment, the antibodies prepared in step (b) are monoclonal antibodies. Thus, the term "preparing antibodies from said immunized animal," as used herein, includes obtaining B-cells from an immunized animal and using those B cells to produce a hybridoma that expresses antibodies, as well as obtaining antibodies directly from the serum of an immunized animal.

In yet another preferred embodiment, the antibodies selected in step (c) cause at least about 10% specific lysis mediated by NK cells displaying a 4Ig-B7-H3R, and preferably at least about 40% specific lysis, at least about 50% specific lysis, or more preferably at least about 70% specific lysis (e.g., about 60-100% specific lysis), as measured in a standard chromium release assay, towards a target cell expressing a 4Ig-B7-H3 protein, compared with the lysis or cytotoxicity obtained at the same effector/target ratio with NK cells that are not blocked by such a 4Ig-B7-H3 protein.

Optionally, the method also or alternatively may further comprise additional steps of making fragments of the monoclonal antibody or derivatives of the monoclonal antibody or such fragments, e.g., as described elsewhere herein.

In a preferred embodiment, the non-human animal used to produce antibodies according to applicable methods of the invention is a mammal, such as a rodent (e.g., mouse, rat, etc.), bovine, porcine, horse, rabbit, goat, sheep, etc. Also, the non-human mammal may be genetically modified or engineered to produce "human" antibodies, such as the Xenomouse™ (Abgenix) or HuMAb-Mouse™ (Medarex). Such methods are further described herein in the section titled "Producing antibodies suitable for use in humans".

In another variant, the invention provides a method for obtaining an antibody that comprises:

a) selecting, from a library or repertoire, a monoclonal antibody, a fragment of a monoclonal antibody, or a derivative of either thereof that specifically binds a 4Ig-B7-H3 or 4Ig-B7-H3R polypeptide, and b) selecting an antibody, fragment, or derivative of (a) that is capable of neutralizing inhibition of NK cell cytotoxicity on a population of NK cells expressing 4Ig-B7-H3R.

The repertoire may be any (recombinant) repertoire of antibodies or fragments thereof, optionally displayed by any suitable structure (e.g., phage, bacteria, synthetic complex, etc.). Selection of inhibitory antibodies may be performed as disclosed above and further illustrated in the examples.

These antibodies are thus "neutralizing" or "inhibitory" antibodies, in the sense that they block, at least partially and detectably, the inhibitory signaling pathway mediated by a 4Ig-B7-H3R when it interacts with 4Ig-B74-H3 molecule. Inhibition of 4Ig-B7-H3 or 4Ig-B7-H3R-mediated inhibition of NK cell cytotoxicity can be assessed by various assays or tests, such as binding or cellular assays.

It will be appreciated that depending on the particular application and format, NK cell potentiating antibodies may be depleting or non-depleting towards cells to which they bind. For example, an NK cell potentiating antibody which binds 4Ig-B7-H3 and blocks the interaction of the 4Ig-B7-H3 protein with its receptor may advantageously be, but is not required to be, depleting toward the 4Ig-B7-H3-expressing cells to which it is bound. Optionally, depleting antibodies comprise a cytotoxic moiety. Optionally, depleting antibodies comprise an Fc region, preferably of the IgG1 or IgG3 subclass. In another embodiment, a depleting antibody is modified so as to increase binding to FcgammaR3a (CD 16) on NK cells, preferably comprising one or more amino acid substitutions in the Fc region of the antibody, as further described herein.

An NK cell potentiating antibody which binds 4Ig-B7-H3R on NK cells and blocks the interaction of the 4Ig-B7-H3 receptor with 4Ig-B7-H3 may advantageously be, but is not required to be, non-depleting. Such a non-depleting antibody may have the advantage of avoiding potential depletion of NK cells involved in killing target cells. In other aspects, a non-depleting antibody comprises or consists of an antigen-binding-fragment, optionally further linked to a moiety (for example a PEG polymer) capable of increasing the serum half life of the fragment. In other aspects, this antibody comprises an Fc region of the IgG2 or IgG4 subclass. In another embodiment, this antibody is modified so as to decrease binding to FcgammaR3a (CD16) on NK cells, preferably comprising one or more amino acid substitutions in the Fc region of the antibody, as further described herein. Antibodies that bind 4Ig-B7-H3-expressing target cells In the case of antibodies that bind 4Ig-B7-H3-expressing cells, the anti-4Ig-B7-H3 antibodies of this invention may be useful in diagnostic and/or therapeutic methods. When used as a diagnostic such antibodies may be useful to identify overproliferating or other cells that express 4Ig-B7-H3, for example to diagnose a tumor or to identify cells that are resistant to lysis by NK cells. Such diagnostic antibodies can be used in vivo or in vitro, that is, they may be administered to an individual or they may be used to detect cells in a biological sample or in cell culture. When used as a therapeutic, the antibodies that bind 4Ig-B7-H3-expressing cells may neutralize the protective effect of the 4Ig-B74-H3 protein to the cell, by targeting the cells for destruction by the immune system (e.g. via antibody-dependent cytotoxicity, also referred to as ADCC), or, by killing the cells directly by contacting them with a cytotoxic agent such as a radioisotope, toxin, or drug.

It will be appreciated that depending on the particular application and format, the antibodies that bind 4Ig-B7-H3-expressing cells (e.g. preferably anti-4IG-B7-H3 antibodies) may, but are not required to, block interactions between the 4Ig-B7-H3 protein and 4Ig-B7-H3R, and moreover need not neutralize the protective effect of the 4Ig-B7-H3 protein to the 4Ig-B7-H3-expressing cell. In particular, such blocking or neutralizing mechanism may not be needed when the anti-4IG-B7-H3 antibodies remain capable of targeting the cells for destruction by the immune system (e.g. via antibody-dependent cytotoxicity, also referred to as ADCC), or when the anti-4IG-B7-H3 antibodies are capable of killing the cells directly by bringing them into contact with a cytotoxic agent such as a radioisotope, toxin, or drug. Nevertheless, in preferred aspects, an antibody is capable of both (a) blocking interactions between the 4Ig-B7-H3 protein and 4Ig-B7-H3R, and (b) mediating target cell depletion, the latter depletion step generally comprising targeting the cells for destruction by the immune system (e.g. via antibody-dependent cytotoxicity, also referred to as ADCC), or bringing them into contact with a cytotoxic agent. Optionally, depleting antibodies comprise a cytotoxic moiety. Optionally, depleting antibodies comprises an Fc region, preferably of the IgG1 or IgG3 subclass. In another embodiment, this antibody is modified so as to increase binding to FcgammaR3a (CD1 6) on NK cells, preferably comprising one or more amino acid substitutions in the Fc region of the antibody, as further described herein.

It will also be appreciated that depending on the particular application and format, the antibodies that bind 4Ig-B7-H3-expressing cells (e.g. preferably anti-4IG-B7-H3 antibodies) may be depleting or non-depleting towards the 4Ig-B7-H3-expressing cells. For example, an antibody that neutralizes the protective effect of the 4Ig-B7-H3 protein to a proliferating cell by blocking the interaction of the 4Ig-B7-H3 protein with its receptor need not be depleting toward the 4Ig-B7-H3-expressing cells to which it is bound. In preferred aspects, this antibody comprises or consists of an antigen-binding-fragment, optionally further linked to a moiety capable of increasing the serum half life of the fragment. In other aspects, this antibody comprises an Fc region of the IgG2 or IgG4 subclass. In another embodiment, this antibody is modified so as to decrease binding to FcgammaR3a (CD16) on NK cells, preferably comprising one or more amino acid substitutions in the Fc region of the antibody, as further described herein.
Producing Antibodies Suitable for use in Humans Once monoclonal antibodies are produced, generally in non-human animals, that can specifically bind to 4Ig-B7-H3 or 4Ig-B7-H3R, the antibodies will generally be modified so as to make them suitable for therapeutic use in humans. For example, if they are not human antibodies, they may be humanized, chimerized, or selected from a library of human antibodies using methods well known in the art. Such human-suitable antibodies can be used directly in the present therapeutic methods, or can be further derivatized into cytotoxic antibodies, as described infra, for use in the methods.

In one, preferred, embodiment, the DNA of a hybridoma producing an antibody of this invention, e.g. a 5B14-like antibody, can be modified prior to insertion into an expression vector, for example, by substituting the coding sequence for human heavy- and light-chain constant domains in place of the homologous non-human sequences (e.g., Morrison et al. (1984) *PNAS* 81:6851), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody of the invention.

In one particularly preferred embodiment, the antibody of this invention is humanized. "Humanized" forms of antibodies according to this invention are specific chimeric immunoglobulins, immunoglobulin chains or fragments thereof (such as Fv, Fab, Fab', F(ab')$_2$, or other antigen-binding subsequences of antibodies) which contain minimal sequence derived from the murine or other non-human immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody. In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. For further details see Jones et al. (1986) Nature 321: 522; Reichmann et al. (1988) Nature 332: 323; Verhoeyen et al. (1988) Science 239:1534 (1988); Presta (1992) Curr. Op. Struct. Biol. 2:593; each of which is herein incorporated by reference in its entirety.

The choice of human variable domains, both light and heavy, to be used in making the humanized antibodies is very important to reduce antigenicity. According to the so-called "best-fit" method, the sequence of the variable domain of an antibody of this invention is screened against the entire library of known human variable-domain sequences. The human sequence which is closest to that of the mouse is then accepted as the human framework (FR) for the humanized antibody (Sims et al. (1993) J. Immun., 151:2296; Chothia and Lesk (1987) J. Mol. Biol. 196:901). Another method uses a particular framework from the consensus sequence of all human antibodies of a particular subgroup of light or heavy chains.

The same framework can be used for several different humanized antibodies (Carter et al. (1992) PNAS 89:4285; Presta et al. (1993) J. Immunol. 51:1993)).

It is further important that antibodies be humanized while retaining their high affinity for 4Ig-B7-H3 or 4Ig-B7-H3R, preferably human receptors, and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Human antibodies may also be produced according to various other techniques, such as by using, for immunization, other transgenic animals that have been engineered to express a human antibody repertoire. In this technique, elements of the human heavy and light chain loci are introduced into mice or other animals with targeted disruptions of the endogenous heavy chain and light chain loci (see, e.g., Jakobovitz et al. (1993) Nature 362:255; Green et al. (1994) Nature Genet. 7:13; Lonberg et al. (1994) Nature 368:856; Taylor et al. (1994) Int. Immunl 6:579, the entire disclosures of which are herein incorporated by reference). Alternatively, human antibodies can be constructed by genetic or chromosomal transfection methods, or through the selection of antibody repertoires using phage display methods. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell (see, e.g., Johnson et al. (1993) Curr Op Struct Biol 3:5564-571; McCafferty et al. (1990) Nature 348:552-553, the entire disclosures of which are herein incorporated by reference). Human antibodies may also be generated by in vitro activated B cells (see, e.g., U.S. Pat. Nos. 5,567,610 and 5,229,275, the disclosures of which are incorporated in their entirety by reference).

In one embodiment, "human" monoclonal antibodies are made using an animal such as a XenoMouse® (Abgenix, Fremont, Calif.) for immunization. A XenoMouse is a murine host that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference. An analogous method can be achieved using a HuMAb-Mouse™ (Medarex).

The antibodies of the present invention may also be derivatized to "chimeric" antibodies (immunoglobulins) in which a portion of the heavy and/or light chain is identical with or homologous to corresponding sequences in the original antibody, while the remainder of the chain(s) is identical with or homologous to corresponding sequences in antibodies derived from another species or belonging to another antibody class or subclass, as well as fragments of such antibodies, so long as they exhibit the desired biological activity (see, e.g., Morrison et al. (1984) PNAS 81:6851; U.S. Pat. No. 4,816,567).

Preparing Cytotoxic Antibodies

While antibodies in underivatized or unmodified form, particularly of the IgG1 or IgG3 type are expected to inhibit the proliferation of the overproliferating 4Ig-B7-H3-expressing cells or be cytotoxic towards overproliferating 4Ig-B7-H3-expressing cells such as in those from a neuroblastoma, carcinoma and melanoma patients, it is also possible to prepare derivatized antibodies to make them cytotoxic. In one embodiment, once 4Ig-B7-H3 specific antibodies are isolated and rendered suitable for use in humans, they will be derivatized to make them toxic to cells. In this way, administration of the antibody to patients will lead to the relatively specific binding of the antibody to overproliferating cells, thereby directly killing or inhibiting the cells underlying the disorder. Because of the specificity of the treatment, other, non-overproliferating cells of the body will be minimally affected by the treatment.

Any of a large number of toxic moieties or strategies can be used to produce such antibodies. In certain, preferred embodiments, the antibodies will be directly derivatized with radioisotopes or other toxic compounds. In such cases, the labeled monospecific antibody can be injected into the patient, where it can then bind to and kill cells expressing the target antigen, with unbound antibody simply clearing the body. Indirect strategies can also be used, such as the "Affinity Enhancement System" (AES) (see, e.g., U.S. Pat. No. 5,256,395; Barbet et al. (1999) Cancer Biother Radiopharm 14:153-166; the entire disclosures of which are herein incorporated by reference). This particular approach involves the use of a radiolabeled hapten and an antibody that recognizes both the NK cell receptor and the radioactive hapten. In this case, the antibody is first injected into the patient and allowed to bind to target cells, and then, once unbound antibody is allowed to clear from the blood stream, the radiolabeled hapten is administered. The hapten binds to the antibody-antigen complex on the overproliferating 4Ig-B7-H3-expressing cells, thereby killing them, with the unbound hapten clearing the body.

Any type of moiety with a cytotoxic or cytoinhibitory effect can be used in conjunction with the present antibodies to inhibit or kill specific 4Ig-B7-H3-expressing cells, including radioisotopes, toxic proteins, toxic small molecules, such as drugs, toxins, immunomodulators, hormones, hormone antagonists, enzymes, oligonucleotides, enzyme inhibitors, therapeutic radionuclides, angiogenesis inhibitors, chemotherapeutic drugs, vinca alkaloids, anthracyclines, epidophyllotoxins, taxanes, antimetabolites, alkylating agents, antibiotics, COX-2 inhibitors, SN-38, antimitotics, antiangiogenic and apoptotoic agents, particularly doxorubicin, methotrexate, taxol, CPT-11, camptothecans, nitrogen mustards, gemcitabine, alkyl sulfonates, nitrosoureas, triazenes, folic acid analogs, pyrimidine analogs, purine analogs, platinum coordination complexes, Pseudomonas exotoxin, ricin, abrin, 5-fluorouridine, ribonuclease (RNase), DNase I, Staphylococcal enterotoxin-A, pokeweed antiviral protein, gelonin, diphtherin toxin, Pseudomonas exotoxin, and Pseudomonas endotoxin and others (see, e.g., Remington's Pharmaceutical Sciences, 19th Ed. (Mack Publishing Co. 1995); Goodman and Gilman's The Pharmacological Basis of Therapeutics (McGraw Hill, 2001); Pastan et al. (1986) Cell 47:641; Goldenberg (1994) Cancer Journal for Clinicians 44:43; U.S. Pat. No. 6,077,499; the entire disclosures of which are herein incorporated by reference). It will be appreciated that a toxin can be of animal, plant, fungal, or microbial origin, or can be created de novo by chemical synthesis.

The toxins or other compounds can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (see, e.g., Yu et al. (1994) Int. J. Cancer 56: 244; Wong, Chemistry of Protein. Conjugation and Cross-linking (CRC Press 1991); Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, engineering and clinical application, Ritter et al. (eds.), pages 60-84 (Cambridge University Press 1995), Cattel et al. (1989) Chemistry today 7:51-58, Delprino et al. (1993) J. Pharm. Sci 82:699-704; Arpicco et al. (1997) Bioconjugate Chemistry 8:3; Reisfeld et al. (1989) Antihody, Immunicon. Radiopharrn. 2:217; the entire disclosures of each of which are herein incorporated by reference).

In one, preferred, embodiment, the antibody will be derivatized with a radioactive isotope, such as 1-131. Any of a number of suitable radioactive isotopes can be used, including, but not limited to, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium- 161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-105, Palladium-109, Praseodymium-143, Promethium-149, Erbium-169, Iridium-194, Gold-198, Gold-199, and Lead-211. In general, the radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Also preferred are radionuclides that substantially decay with generation of alpha-particles.

In selecting a cytotoxic moiety for inclusion in the present methods, it is desirable to ensure that the moiety will not exert significant in vivo side effects against life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The term "significant side effects", as used herein, refers to an antibody, ligand or antibody conjugate, that, when administered in vivo, will produce only negligible or clinically manageable side effects, such as those normally encountered during chemotherapy.

Once antibodies are obtained that are known to specifically bind to the desired antigen (e.g. preferably 4Ig-B7-H3), and which have been rendered suitable for use in humans, and optionally derivatized to include a toxic moiety, they will generally be assessed for their ability to interact with, affect the activity of, and/or kill target cells. In general, the assays described above for detecting antibody binding to 4Ig-B7-H3 and 4Ig-B7-H3R, including competition-based assays, ELISAs, radioimmunoassays, Western blotting, BIACORE-based assays, and flow cytometry assays, can be equally applied to detect the interaction of humanized, chimeric, or other human-suitable antibodies, such as cytotoxic antibodies, with their target cells. Typically, target cells will be cells taken from patients with a proliferative disorder, especially tumor or inflammatory disorder.

In the present assays, the ability of the humanized or human-suitable, therapeutic (e.g. cytotoxic) antibody to bind to 4Ig-B7-H3 polypeptides or to cells expressing said polypeptides will be compared with the ability of a control protein, e.g. an antibody raised against a structurally unrelated antigen, or a non-Ig peptide or protein, to bind to the same target. Antibodies or fragments that bind to the target cells or 4Ig-B7-H3 polypeptide, as assessed using any suitable assay with 25%, 50%, 100%, 200%, 1000%, or higher increased affinity relative to the control protein, are said to "specifically bind to" or "specifically interact with" the target, and are preferred for use in the therapeutic methods described below.

In addition to binding, the ability of the antibodies to inhibit the proliferation of, or, preferably, kill, target cells can be assessed. In one embodiment, human cells expressing 4Ig-B7-H3 are taken from a patient with a disorder, are introduced into plates, e.g., 96-well plates, and exposed to various amounts of the relevant antibodies. By adding a vital dye, i.e. one taken up by intact cells, such as AlamarBlue (BioSource International, Camarillo, Calif.), and washing to remove excess dye, the number of viable cells can be measured by virtue of the optical density (the more cells killed by the antibody, the lower the optical density). (See, e.g., Connolly et al. (2001) J Pharm Exp Ther 298:25-33, the disclosure of which is herein incorporated by reference in its entirety). Any other suitable in vitro cytotoxicity assay, assay to measure cell proliferation or survival, or assay to detect target cell activity can equally be used, as can in vivo assays, e.g. administering the antibodies to animal models, e.g., mice, containing human cells expressing 4Ig-B7-H3, and detecting the effect of the antibody administration on the survival or activity of the 4Ig-B7-H3-expressing target cells over time. Also, where the antibody cross-reacts with a non-human 4Ig-B7-

H3 protein, e.g., a primate 4Ig-B7-H3-expressing cell, the therapeutic antibodies can be used in vitro or in vivo to assess the ability of the antibody to bind to and/or kill target cells from the animal that express 4Ig-B7-H3.

Any antibody, preferably a human-suitable antibody, e.g. a cytotoxic antibody, that can detectably slow, stop, or reverse the proliferation of the overproliferating cells, in vitro or in vivo, can be used in the present methods. Preferably, the antibody is capable of stopping the proliferation (e.g., preventing an increase in the number of cells in vitro or in vivo expressing the targeted 4Ig-B7-H3 polypeptide), and most preferably the antibody can reverse the proliferation, leading to a decrease in the total number of such cells. In certain embodiments, the antibody is capable of producing a 10%, 20%, 30%, 40%, 50%, 60%, 70%, 80%, 90%, 95%, 96%, 97%, 98%, 99%, or 100% decrease in the number of cells expressing the 4Ig-B7-H3 polypeptide.

In one preferred embodiment, therefore, the present invention provides a method for producing an antibody suitable for use in the treatment of a proliferative disorder such as carcinoma, melanoma and neuroblastoma, the method comprising the following steps: a) providing a plurality of antibodies that specifically bind to 4Ig-B7-H3 present on the surface of cells; b) testing the ability of the antibodies to bind to cells (preferably proliferating cells or tumor cells) taken from one or more patients with a proliferative disorder; c) selecting an antibody from said plurality that binds to a substantial number of cells taken from one or more of said patients; and d) making said antibody suitable for human administration. In one embodiment, the method further comprises a step in which a cytotoxic agent is linked to said antibody. In such methods, "substantial number" can mean e.g., 30%, 40%, 50%, preferably 60%, 70%, 80%, 90% or a higher percentage of the cells.

It will be appreciated that equivalent methods can be used to produce antibodies suitable for treating animals, or for testing in an animal model. In that case, the antibodies will be ensured to be capable of specifically recognizing a 4Ig-B7-H3 protein from the relevant animal, and prevalent in an animal disease involving unwanted cell proliferation. Similarly, the antibody will be modified to be suitable for administration into the particular animal.

Antibodies having Modified Ability to Induce ADCC

In some embodiments, the invention provides altered antibodies that have altered affinity, either higher or lower affinity, for an activating FcγR, e.g., FcγRIII. In certain preferred embodiments, altered antibodies having higher affinity for FcγR are provided. Preferably such modifications also have an altered Fe-mediated effector function. This may be advantageous when using an anti-Ig4-B7-H3 antibody to target an Ig4-B7-H3-expressing cell for elimination.

Modifications that affect Fc-mediated effector function are well known in the art (See U.S. Pat. No. 6,194,351, which is incorporated herein by reference in its entirety). The amino acids that can be modified include but are not limited to proline 329, proline 331, and lysine 322. Proline 329 and/or 331 and lysine 322 can, preferably be replaced with alanine, however, substitution with any other amino acid is also contemplated. See International Publication No.: WO 00/142072 and U.S. 6,194,551 which are incorporated herein by reference in their entirety.

Thus, modification of the Fe region can comprise one or more alterations to the amino acids found in the antibody Fc region. Such alterations can result in an antibody with an altered antibody-mediated effector function, an altered binding to other Fc receptors (e.g., Fc activation receptors), an altered ADCC activity, an altered Clq binding activity, an altered complement dependent cytotoxicity activity, or any combination thereof The invention also provides antibodies with altered oligosaccharide content. As used herein, oligosaccharides refer to carbohydrates containing two or more simple 20 sugars and the two terms may be used interchangeably herein. Carbohydrate moieties of the instant invention will be described with reference to commonly used nomenclature in the art. For a review of carbohydrate chemistry, see, e.g., Hubbard et al., 198 1 Ann. Rev. Biochem., 50: 555-583, which is incorporated herein by reference in its entirety'. This nomenclature includes for example, Man which represents mannose; GlcNAc which represents 2-N-acetylglucosamine; Gal which represents galactose; Fuc for fucose and Glc for glucose. Sialic acids are described by the shorthand notation NeuNAc for 5-N-acetylneuraminic acid, and NeuNGc for 5-glycolneuraminic.

Antibodies typically contain carbohydrate moieties at conserved positions in the constant region of the heavy chain, and up to 30% of human IgGs have a glycosylated Fab region. IgG has a single N-linked biantennary carbohydrate structure at Asn 297 which resides in the CH2 domain (Jefferis et al., 1998, Immunol. Rev. 163: 59-76; Wright et al., 1997, Trends Biotech 15: 26-32). Human IgG typically has a carbohydrate of the following structure; GlcNAc(Fucose)-GlcNAc-Man-(ManGlcNAc)2. However variations among IgGs in carbohydrate content do occur which leads to altered function, see, e.g., Jassal et al., 35 2001 Biochem. Biophys. Res. Commun. 288: 243-9; Groenink et al., 1996 J. Immunol. 26: 37 1404-7; Boyd et al., 1995 Mol. Immunol. 32: 13 1 1-8; Kumpel et al., 1994, Human Antibody Hybridomas, 5: 143-5.

Antibodies comprising a variation in the carbohydrate moiety that is attached to Asn 297 are also provided by the subject invention. The carbohydrate moiety can have a galactose and/or galactose-sialic acid at one or both of the terminal GlcNAc and/or a third GlcNac chain. In some embodiments, the antibodies are substantially free of one or more selected sugar groups, e.g., one or more sialic acid residues, one or more galactose residues, and/or one or more fucose residues. An antibody that is substantially free of one or more selected sugar groups may be prepared using common methods known to one skilled in the art, including for example recombinantly producing an antibody of the invention in a host cell that is defective in the addition of the selected sugar groups(s) to the carbohydrate moiety of the antibody, such that about 90-100% of the antibody in the composition lacks the selected sugar group(s) attached to the carbohydrate moiety.

Alternative methods for preparing such antibodies include for example, culturing cells under conditions which prevent or reduce the addition of one or more selected sugar groups, or post-translational removal of one or more selected sugar groups. In a specific embodiment, a method of producing a substantially homogenous antibody preparation, wherein about 80-100% of the antibody in the composition lacks a fucose on its carbohydrate moiety, e.g., the carbohydrate attachment on Asn 297 is provided. The antibody may be prepared for example by (a) use of an engineered host cell that is deficient in fucose metabolism such that it has a reduced ability to fucosylate proteins expressed therein; (b) culturing cells under conditions which prevent or reduce fucosylation; (c) post-translational removal of fucose, e.g., with a fucosidase enzyme; or (d) purification of the antibody so as to select for the product which is not fucosylated. Most preferably, nucleic acid encoding the desired antibody is expressed in a host cell that has a reduced ability to fucosylate the antibody expressed therein.

Host cells for the production of such antibodies are, preferably, dihydrofolate reductase (DHR) deficient. DHR deficient Chinese hamster ovary cells (CHO) are known in the art, e.g., a Lec 13 CHO cell (lectin resistant CHO mutant cell line; Ribka & Stanley, 1986, Somatic Cell & Molec. Gen. 12(1): 51-62; Ripka et al., 1986 Arch. Biochem. Biophys. 249(2): 533-45), CHO-K1, DUX-B11, CHO-DP12 or CHO-DG44. Such cells can be modified so that the antibody is not substantially fucosylated. Thus, the cell may display altered expression and/or activity for the fucosyltransferase enzyme, or another enzyme or substrate involved in adding fucose to the N-linked oligosaccharide so that the enzyme has a diminished activity and/or reduced expression level in the cell. For methods to produce antibodies with altered fucose content, see, e.g., WO 03/035835 and Shields et al., 2002, J Biol. Chem. 277(30): 26733-40; both of which are incorporated herein by reference in their entirety.

The altered carbohydrate modifications can modulate one or more of the following characteristics of the antibody: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (see Shields R. L. et al., 2001, 10 J. Biol. Chem. 277(30): 26733-40; Davies J. et al., 2001, Biotechnology & Bioengineering, 74(4): 288-294).

The altered carbohydrate modifications enhance the binding of antibodies of the invention to FcγR receptors (e.g., FcγRIIIA). Altering carbohydrate modifications in accordance with the methods of the invention includes, for example, increasing the carbohydrate content of the antibody or decreasing the carbohydrate content of the antibody. Methods of altering carbohydrate contents are known to those skilled in the art, see, e.g., Wallick et al., 1988, Journal of Exp. Med. 168(3): 1099-1 109; Tao et al., 1989 Journal of Immunology, 143(8): 2595-2601; Routledge et al., 1995 Transplantation, 60(8): 847-53; Elliott et al. 2003; Nature Biotechnology, 2 1: 4 14-2 1; Shields et al. 2002 Journal of Biological Chemistry, 277(30): 26733-40; all of which are incorporated herein by reference in their entirety. In some aspects of the invention, antibodies comprising one or more glycosylation sites, so that one or more carbohydrate moieties are covalently attached to the antibody are provided. In other embodiments, the invention encompasses antibodies comprising one or more glycosylation sites and one or more modifications in the Fc region, such as those disclosed supra and those known to one skilled in the art. In preferred embodiments, the one or more modifications in the Fc region enhance the affinity of the antibody for an activating FcγR, e.g., FcγIIIA, relative to the antibody comprising the wild type Fc regions. Antibodies of the invention with one or more glycosylation sites and/or one or more modifications in the Fc region have an enhanced antibody mediated effector function, e.g., enhanced ADCC activity or NK activating activity.

In some embodiments, the invention further comprises antibodies comprising one or more modifications of amino acids that are directly or indirectly known to interact with a carbohydrate moiety of the antibody, including but not limited to amino acids at positions 241, 243, 244, 245, 245, 249, 256, 258, 260, 262, 264, 265, 296, 299, and 301. Amino acids that directly or indirectly interact with a carbohydrate moiety of an antibody are known in the art, see, e.g., Jefferis et al., 1995 Immunology Letters, 44: 11 1-7, which is incorporated herein by reference in its entirety.

Antibodies that have been modified by introducing one or more glycosylation sites into one or more sites of the antibodies, preferably without altering the functionality of the antibody, e.g., binding activity to FcγRIII can also be used in the practice of the subject invention. Glycosylation sites may be introduced into the variable and/or constant region of the antibodies of the invention. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. The antibodies of the invention may comprise one or more glycosylation sites, including N-linked and O-linked glycosylation sites. Any glycosylation site for N-linked or O-linked glycosylation known in the art may be used in accordance with the instant invention. An exemplary N-linked glycosylation site that is useful in accordance with the methods of the present invention, is the amino acid sequence: Asn-X-Thr/Ser, wherein X may be any amino acid and Thr/Ser indicates a threonine or a serine. Such a site or sites may be introduced into an antibody of the invention using methods well known in the art to which this invention pertains. See, for example, "In Vitro Mutagenesis," Recombinant DNA: A Short Course, J. D. Watson, et al. W.H. Freeman and Company, New York, 1983, chapter 8, pp. 106-1 16, which is incorporated herein by reference in its entirety.

An exemplary method for introducing a glycosylation site into an antibody of the invention may comprise: modifying or mutating an amino acid sequence of the antibody so that the desired Asn-X-Thr/Ser sequence is obtained. In some embodiments, the invention encompasses methods of modifying the carbohydrate content of an antibody of the invention by adding or deleting a glycosylation site. Methods for modifying the carbohydrate content of antibodies are well known in the art and encompassed within the invention, see, e.g., U.S. Pat. No. 6,218,149; EP 0 359 096 B1; U.S. Publication No. US 200210028486; WO 03/035835; U.S. Publication No. 2003/0115614; U.S. Pat. No. 6,218,149; U.S. Pat. No. 6,472,511; all of which are incorporated herein by reference in their entirety. In other embodiments, the invention encompasses methods of modifying the carbohydrate content of an antibody of the invention by deleting one or more endogenous carbohydrate moieties of the antibody.

The invention further encompasses methods of modifying an effector function of an antibody of the invention, wherein the method comprises modifying the carbohydrate content of the antibody using the methods disclosed herein or known in the art. Standard techniques known to those skilled in the art can be used to introduce mutations in the nucleotide sequence encoding an antibody, or fragment thereof, including, e.g., site-directed mutagenesis and PCR-mediated mutagenesis, which results in amino acid substitutions. Preferably, the derivatives include less than 15 amino acid substitutions, less than 10 amino acid substitutions, less than 5 amino acid substitutions, less than 4 amino acid substitutions, less than 3 amino acid substitutions, or less than 2 amino acid substitutions relative to the original antibody or fragment thereof. In a preferred embodiment, the derivatives have conservative amino acid substitutions made at one or more predicted nonessential amino acid residues. The present invention also encompasses antibodies or fragments thereof comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of the anti-Ig4-B7-H3 antibodies discussed herein. In another preferred embodiment, the invention provides "altered antibodies" or fragments thereof that specifically bind FcγR (e.g., FcγR found on NK cells) with greater affinity than unaltered antibodies or fragments thereof that specifically bind to the same FcγR.

4Ig-B7-H3 Polypeptides, Mimetics and Inhibitors

The invention also provides methods of using 4Ig-B7-H3 polypeptides and variants and derivatives thereof. Such polypeptides may be used for example to identify 4Ig-B7-H3 ligands, to identify cells expressing 4Ig-B7-H3 ligands (e.g. NK cells), to modulate (stimulate or inhibit) an 4Ig-B7-H3R and/or NK cell or more generally immune cell or T lymphocyte activity.

In one aspect the invention provides 4Ig-B7-H3 chimeric or fusion proteins. As used herein, a 4Ig-B7-H3 "chimeric protein" or "fusion protein" comprises a 4Ig-B7-H3 polypeptide operatively linked, preferably fused in frame, to a non-4Ig-B7-H3 polypeptide. In a preferred embodiment, a 4Ig-B7-H3 fusion protein comprises at least one biologically active domain of a 4Ig-B7-H3 protein (see FIG. 8). In another preferred embodiment, a 4Ig-B7-H3 fusion protein comprises at least two biologically active domains of a 4Ig-B7-H3 protein. For example, in one embodiment, the fusion protein is a GST-4Ig-B7-H3 fusion protein in which the 4Ig-B7-H3 sequences are fused to the C-terminus of the GST sequences. Such fusion proteins can facilitate the purification of recombinant 4Ig-B7-H3. In another embodiment, the fusion protein is a 4Ig-B7-H3 protein containing a heterologous signal sequence at its N-terminus, such as for example to allow for a desired cellular localization in a certain host cell. The 4Ig-B7-H3-fusion proteins of the invention can be used for example as immunogens to produce anti-4Ig-B7-H3 antibodies in a subject, to purify 4Ig-B7-H3 ligands, to modulate NK cell activity, and in screening assays to identify molecules which inhibit the interaction of 4Ig-B7-H3 with a 4Ig-B7-H3 receptor.

In a preferred example, the fusion protein comprises a 4Ig-B7-H3 protein, preferably a 4Ig-B7-H3 protein having at least one amino acid deletion, substitution or insertion, fused to an Fc portion of an immunoglobulin protein. Antibodies comprise two functionally independent parts, a variable domain known as "Fab", which binds antigen, and a constant domain, known as "Fc" which provides the link to effector functions such as complement or phagocytic cells. The Fc portion of an immunoglobulin has a long plasma halflife, whereas the Fab is short-lived (Capon, et al., Nature 337: 525-531 (1989)). Preferably the Fc portion is fused at the C terminal of the 4Ig-B7-H3 protein, but can also be fused at the N-terminal. Fc-fusion proteins and methods of making them are described in the present examples, as well as in PCT publication nos. WO 03/104282, WO 03/068977, WO 00/69913, and WO 98/28427 and U.S. patent publication no. US20040067520A1. Therapeutic protein products have been constructed using the Fc domain to provide longer halflife or to incorporate functions such as Fc receptor binding, protein A binding, complement fixation and placental transfer which all reside in the Fc proteins of immunoglobulins. For example, the Fc region of an IgG1 antibody has been fused to the N-terminal end of CD30-L (U.S. Pat. No. 5,480,981). IL-10, an antiinflammatory and antirejection agent has been fused to murine Fcγ2a in order to increase the cytokine's short circulating half-life (Zheng, X. et al., The Journal of Immunology, 154: 5590-5600 (1995)). Studies have also evaluated the use of tumor necrosis factor receptor linked with the Fc protein of human IgG1 to treat patients with septic shock (Fisher, C. et al., N. Engl. J. Med., 334: 1697-1702 (1996); and Van Zee, K. et al., The Journal of Immunology, 156: 2221-2230 (1996)). Fc has also been fused with CD4 receptor to produce a therapeutic protein for treatment of AIDS. (Capon et al., Nature, 337:525-531 (1989)). In addition, the N-terminus of interleukin 2 has also been fused to the Fc portion of IgG1 or IgG 3 to overcome the short half life of interleukin 2 and its systemic toxicity (Harvill et al., Immunotechnology, 1: 95-105 (1995)). The disclosures of each of the above references are incorporated herein by reference for methods of making and using Fc fusion proteins.

The present invention also pertains to use of variants of the 4Ig-B7-H3 proteins which function as either 4Ig-B7-H3 mimetics or inhibitors of NK cell activity. Biologically active portions of a 4Ig-B7-H3 protein include peptides comprising amino acid sequences sufficiently homologous to or derived from the amino acid sequence of the 4Ig-B7-H3 protein, e.g., an amino acid sequence shown in SEQ ID NO 2 or in Steinberger et al (2004), supra, which include less amino acids than the full length 4Ig-B7-H3 protein, and exhibit at least one activity of a 4Ig-B7-H3 protein. Preferably said activity comprises potentiating the activity of an NK cell. Typically, biologically active portions comprise a domain or motif with at least one activity of the 4Ig-B7-H3 proteins, preferably at least one domain from the domains shown in FIG. 8. A biologically active portion of a 4Ig-B7-H3 protein can be a polypeptide which is, for example at least 15, 25, 40, 50, 75, 100, 150, 200, 250 or 300, 400 or 500 amino acids in length. Preferably, an active 4Ig-B7-H3 polypeptide is in tetrameric form, or is capable of forming a 4-Ig-B7-H3 tetramer.

In a preferred embodiment, the invention provides a 4Ig-B7-H3 protein capable of inhibiting NK cell activity and/or capable or binding to a 4Ig-B7-H3 receptor. Preferably such a 4Ig-B7-H3 protein comprises, consists essentially of or consists of the amino acid sequence shown in SEQ ID NO 2. The invention also concerns the polypeptide encoded by a nucleotide sequences shown in SEQ ID NO 1 or in FIG. 3 in Steinberger et al. (2004), a complementary sequence thereof or a fragment thereto. The present invention embodies isolated, purified, and recombinant 4Ig-B7-H3 polypeptide comprising a contiguous span of at least 6 amino acids, preferably at least 8 to 10 amino acids, more preferably at least 12, 15, 20, 25, 30, 40, 50, 100, 150, 200, 250, 300, 400 or 500 amino acids of a sequence of SEQ ID NO 2. In other preferred embodiments the contiguous stretch of amino acids comprises the site of a mutation or functional mutation, including a deletion, addition, swap or truncation of the amino acids in the 4Ig-B7-H3 protein sequence. Optionally said portion of a full length 4Ig-B7-H3 protein is a soluble 4Ig-B7-H3 protein. In one example a portion of a full length 4Ig-B7-H3 protein comprises one or more domains selected from the domains consisting of: IgV1, IgC1, IgV2 and IgC2. Preferably said portion of a full length 4Ig-B7-H3 protein comprises two, three of all four of the IgV1, IgC1, IgV2 and IgC2 domains. Optionally said portion of a full length 4Ig-B7-H3 protein further comprises an L domain. In one aspect, said portion of a full length 4Ig-B7-H3 protein does not comprise a TM domain, and/or does not comprise a CT domain. The domains of the native 4Ig-B7-H3 protein and the amino acid positions corresponding thereto are provided in FIG. 8.

In other preferred embodiments, a 4Ig-B7-H3 protein capable of potentiating NK cell activity is a 4Ig-B7-H3 polypeptide comprising at least 1, 2, 3, 5, 10 or 20 amino acid substitutions. Preferably said polypeptide is capable of binding to a 4Ig-B7-H3R protein and blocking the NK-inhibitory activity of the 4Ig-B7-H3R protein. In another embodiment, a 4Ig-B7-H3 protein capable of blocking 4Ig-B7-H3R activity and potentiating NK cell activity is a portion of a full length 4Ig-B7-H3 protein comprising a contiguous span of at least 6 amino acids, preferably at least 8 to 10 amino acids, more preferably at least 12, 15, 20, 25, 30, 40, 50, 100, 150, 200, 250, 300, 400 or 500 amino acids of a sequence of SEQ ID NO 2; optionally said portion of a full length 4Ig-B7-H3 protein is a soluble 4Ig-B7-H3 protein. In one example a portion of a full length 4Ig-B7-H3 protein comprises one or more domains selected from the domains consisting of: IgV1, IgC1, IgV2 and IgC2. Preferably said portion of a full length 4Ig-B7-H3 protein comprises two, three of all four of the IgV1, IgC1, IgV2 and IgC2 domains. Optionally said portion of a full length 4Ig-B7-H3 protein further comprises an L domain. In one aspect, said portion of a full length 4Ig-B7-H3 protein does not comprise a TM domain, and/or does not comprise a CT domain. The domains of the native 4Ig-B7-H3 protein and the amino acid positions corresponding thereto are provided in FIG. 8.

A 4Ig-B7-H3 protein capable of potentiating NK cell is preferably a composition which binds an NK cell but will not inhibit the activation or cytotoxicity of an NK cell. Furthermore, said 4Ig-B7-H3 protein is preferably a composition comprising a 4Ig-B7-H3 polypeptide comprising at least one amino acid insertion, deletion or substitution compared to the 4Ig-B7-H3 polypeptide of SEQ ID NO 2. Preferably the composition comprising a 4Ig-B7-H3 polypeptide is a soluble polypeptide. Preferably the 4Ig-B7-H3 polypeptide is fused to a Fc portion of an immunoglobulin heavy chain protein.

In other aspects, a 4Ig-B7-H3 inhibitor polypeptide (e.g. an NK cell potentiating polypeptide) is not in tetrameric form, or preferably comprises a modification (e.g. one or more amino acid substitutions or an amino acid deletion) or comprises a fragment of the wild-type 4Ig-B7-H3 protein and is not capable of forming a 4Ig-B7-H3 tetramer under physiological conditions.

In other embodiments, the 4Ig-B7-H3 protein is substantially homologous to a sequence of SEQ ID NO 2, and retains the functional activity of a protein of SEQ ID NO 2, yet differs in amino acid sequence due to natural allelic variation or mutagenesis. Accordingly, in another embodiment, the 4Ig-B7-H3 proteins are proteins which comprise an amino acid sequence at least about 60% homologous to an amino acid sequence of SEQ ID NO 2 and retain the functional activity of the 4Ig-B7-H3 protein of SEQ ID NO 2. Preferably, the proteins are at least about 30%, 40%, 50%, 60%, 70%, 80%, 85%, 90%, 92%, 95%, 97%, 98%, 99% or 99.8% homologous to a protein of SEQ ID NO 2 or to a fragment thereof.

To determine the percent homology of two amino acid sequences or of two nucleic acids, the sequences are aligned for optimal comparison Purposes (e.g., gaps can be introduced in the sequence of a first amino acid or nucleic acid sequence for optimal alignment with a second amino or nucleic acid sequence and non-homologous sequences can be disregarded for comparison purposes). In a preferred embodiment, the length of a reference sequence aligned for comparison purposes is at least 30%, preferably at least 40%, more preferably at least; 50%, even more preferably at least 60%, and even more preferably at least 70%, 80%, 90% or 95% of the length of the reference sequence (e.g., when aligning a second sequence to a 4Ig-B7-H3 amino acid sequences of SEQ ID NO 2 having 534 amino acid residues, at least 100, preferably at least 200, more preferably at least 250, even more preferably 500 amino acid residues are aligned or when aligning a second sequence to a 4Ig-B7-H3 nucleic acid sequence of SEQ ID NO 2, preferably a human 4Ig-B7-H3 sequence comprising, consisting essentially of or consisting of 3419 or 3452 nucleotides which encode the amino acids of the 4Ig-B7-H3 protein, preferably at least 100, preferably at least 200, more preferably at least 300, even more preferably at least 400, and even more preferably at least 500, 600, at least 700, at least 800, at least 900, or more than 1000 nucleotides are aligned.

The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "identity" is equivalent to amino acid or nucleic acid "homology"). The percent homology between the two sequences is a function of the number of identical positions shared by the sequences (i.e., % homology=number (#) of identical positions/total number (#) of positions 100).

The comparison of sequences and determination of percent homology between two sequences can be accomplished using a mathematical algorithm. A preferred, non-limiting example of a mathematical algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873 Such an algorithm is incorporated into the NBLAST and XBLAST programs (version 2.0) of Altschul, et al. (1990) J. Mol. Biol. 215:403. BLAST nucleotide searches can be performed with the NBLAST program, score 1.00, limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Variants of the 4Ig-B7-H3 proteins can be generated by mutagenesis, e.g., discrete point mutation(s) or truncation of a 4Ig-B7-H3 protein. A 4Ig-B7-H3 agonist protein can retain substantially the same, or a subset, of the biological activities of the naturally occurring form of a 4Ig-B7-H3 protein. A 4Ig-B7-H3 antagonist protein can inhibit one or more of the activities of the naturally occurring form of the 4Ig-B7-H3 protein by, for example, competitively inhibiting the binding of a naturally occurring 4Ig-B7-H3 protein to a 4-Ig-B7-H3 receptor on an NK cell. Thus, specific biological effects can be elicited by treatment with a variant of limited function. In one embodiment, variants of a 4Ig-B7-H3 protein which function as either 4Ig-B7-H3 agonists (mimetics) or as 4Ig-B7-H3 antagonists can be identified by screening combinatorial libraries of mutants, e.g., truncation mutants, of a 4Ig-B7-H3 protein for 4Ig-B7-H3 protein agonist or antagonist activity. In one embodiment, a variegated library of 4Ig-B7-H3 variants is generated by combinatorial mutagenesis at the nucleic acid level and is encoded by a variegated gene library. A variegated library of 4Ig-B7-H3 variants can be produced by, for example, enzymatically ligating a mixture of synthetic oligonucleotides into gene sequences such that a degenerate set of potential 4Ig-B7-H3 sequences is expressible as individual polypeptides, or alternatively, as a set of larger fusion proteins (e.g., for phage display) containing the set of 4Ig-B7-H3 sequences therein. There are a variety of methods which can be used to produce libraries of potential 4Ig-B7-H3 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential 4Ig-B7-H3 sequences.

In addition, libraries of fragments of a 4Ig-B7-H3 protein coding sequence can be used to generate a variegated population of 4Ig-B7-H3 fragments for screening and subsequent selection of variants of a 4Ig-B7-H3 protein. In one embodiment, a library of coding sequence fragments can be generated by treating a double stranded PCR fragment of a 4Ig-B7-H3 coding sequence with a nuclease under conditions wherein nicking occurs only about once per molecule, denaturing the double-stranded DNA, renaturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes N-terminal, C-terminal and internal fragments of various sizes of the 4Ig-B7-H3 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of 4Ig-B7-H3 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected.

Use of 4Ig-B7-H3 to Identify Ligands on NK Cells

Determining the ability of the 4Ig-B7-H3 protein to bind to or interact with a 4Ig-B7-H3 ligand, particularly a 4Ig-B7-H3 receptor found on NK cells, can be accomplished by any suitable method, for example methods for determining binding to candidate ligands. For example, an assay can be used in which a 4Ig-B7-H3 protein or biologically active portion thereof is contacted with a candidate ligand and the ability of the candidate ligand to bind to the 4Ig-B7-H3 protein or biologically active portion thereof is determined. Binding of the candidate ligand to the 4Ig-B7-H3 protein can be determined either directly or indirectly. Direct binding can be assessed via BIA based protocols.

In one example, a 4Ig-B7-H3 protein can be used in an immunoprecipitation method to isolate a 4Ig-B7-H3 ligand. Any suitable method can be used, see Ausubel et al (Ed.), Current Protocols in Molecular Biology, 1994, John Wiley & Sons, USA, the disclosure of which is incorporated herein by reference. It may be desirable to immobilize 4Ig-B7-H3 to facilitate separation of complexed from uncomplexed forms of 4Ig-B7-H3 or its ligand, as well as to accommodate automation of the assay. Binding of a candidate ligand to a 4Ig-B7-H3 protein can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/4Ig-B7-H3 fusion proteins or glutathioneS-transferase/target fusion proteins can be adsorbed onto glutathione sepharose beads (Sigma Chemical, St. Louis, Mo.) or glutathione derivatized microtitre plates, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of 4Ig-B7-H3 binding determined using standard techniques. Following isolation of a 4Ig-B7-H3 ligand, the ligand can be digested (e.g. tryptic fragments) and the terminal amino acid sequence can be determined.

Techniques for immobilizing proteins on matrices can also be used in the assays of the invention to identify compounds that interfere with binding of 4Ig-B7-H3 and a candidate ligand. For example, either a 4Ig-B7-H3 protein or a candidate ligand can be immobilized utilizing conjugation of biotin and streptavidin. Biotinylated 4Ig-B7-H3 protein or candidate ligand can be prepared from biotin-N-HS (N-hydroxysuccinimide) using techniques well known in the art (e.g., biotinylation Idt, Pierce Chemicals, Rockford, Ill.), and immobilized in the wells of streptavidin-coated 96 well plates (Pierce Chemical). Alternatively, antibodies reactive with 4Ig-B7-H3 protein or candidate ligand but which do not interfere with binding of the 4Ig-B7-H3 protein to its target molecule can be derivatized to the wells of the plate, and unbound candidate ligand or 4Ig-B7-H3 protein trapped in the wells by antibody conjugation. This can be carried out in the presence or absence of a compound to be tested for its ability to interfere with 4Ig-B7-H3 binding. Methods for detecting protein complexes, in addition to those described above for the GST-immobilized complexes, include immunodetection of complexes using antibodies reactive with the 4Ig-B7-H3 protein or candidate ligand, as well as enzyme-linked assays which rely on detecting an enzymatic activity associated with the 4Ig-B7-H3 protein or candidate ligand.

The methods are amenable to use of both soluble and/or membrane-bound forms of 4Ig-B7-H3 proteins. In the case in which a membrane-bound form of 4Ig-B7-H3 is used it may be desirable to utilize a solubilizing agent such that the membrane-bound form of the isolated protein is maintained in solution. Examples of such solubilizing agents include nonionic detergents such as noctylglucoside, n-dodecylglucoside, n-dodecymaltoside, octanoyl-N-methylglucamide, decanoylN-methylglucamide, Triton™ X-100, Triton™ X-114, Thesit™, Isotridecypoly(ethylene glycol ether)n,3-[(3-cholamidopropyl)dimethylamino]-I-propane sulfonate (CHAPS), 3-[(3cholamidopropyl)dimethylamminiol hydroxy-1-propane sulfonate (CHAPSO), or Ndodecyl=N, N-dimethyl ammonio-1-propane sulfonate.

Administration of Compounds for Treatment Methods

The compounds produced using the present methods can be used in the treatment a wide range of disorders. Compounds which block interaction of 4Ig-B7-H3R with its ligand (e.g. anti-4Ig-B7-H3 and anti-4Ig-B7-H3R antibodies) may be used to potentiate NK cell activity in a general fashion, and thus may be useful in the treatment of any disorder in which NK cells can have a positive effect, including but not limited to cancer, autoimmune disorders, infectious disease.

Compounds which induce killing of 4Ig-B7-H3-expressing cells are particularly effective at treating proliferative disorders, especially tumors, inflammatory and immunoproliferative disorders, most particularly neuroblastoma, carcinoma and melanoma. It will be appreciated that compounds which bind 4Ig-B7-H3 and block interaction of 4Ig-B7-H3 with its ligand, but which are not directly depleting toward the 4Ig-B7-H3-expressing cell (e.g. non-depleting anti-4Ig-B7-H3 antibodies such as certain IgG4 mAbs, or antibody fragments) may also be used effectively in treating proliferative disorders, especially tumors, inflammatory and immunoproliferative disorders, most particularly neuroblastoma, carcinoma and melanoma; such antibodies may remove the target-cell mediated inhibition of NK cells thereby exposing the target (e.g. tumor) cell to NK-mediated killing.

Optionally, present therapeutic methods may comprise a typing step in which the 4Ig-B7-H3 expression on the cells (e.g. typically proliferating cells, tumor cells, etc.) in patients is assessed. Generally, in this step, a sample of cells is taken from a patient, and tested, e.g., using immunoassays, to determine the relative prominence of 4Ig-B7-H3 on the cells. While proliferating or tumor cells are preferred for this method, it will be appreciated that any cell type that is suspected or known to express 4Ig-B7-H3 can be used. Ideally, this step is performed using a kit containing one or more antibodies, either directly or indirectly labeled, that together recognize the 4Ig-B7-H3 protein. If the 4Ig-B7-H3 protein is detected on cells, an anti-4Ig-B7-H3 antibody can be administered such that the overproliferating cells will be specifically targeted.

In addition to the immunological assays described above, other methods can also be used to determine the identity of and relative expression level of 4Ig-B7-H3 in cells taken from patients. For example, RNA-based methods, e.g., RT-PCR or Northern blotting, can be used to examine the relative transcription level of various NK cell receptors in cells taken from a patient. In many cases, a single or small number of receptor-specific transcripts will predominate, allowing treatment of the patient using cytotoxic antibodies specific to the particular receptor(s) encoded by the transcript(s).

In one embodiment the invention provides a kit produced according to the present invention which comprises at least one diagnostic antibody against 4Ig-B7-H3, as well at least one therapeutic antibodies against 4Ig-B7-H3 or 4Ig-B7-H3R.

The kits of the present invention may contain any number of diagnostic and/or therapeutic antibodies, e.g., 1, 2, 3, 4, 5, 6, 7, 8, 9, 10, or any other number of diagnostic and/or therapeutic antibodies. In such kits, the diagnostic antibodies will often be labeled, either directly or indirectly (e.g., using secondary antibodies). Therapeutic antibodies can be unmodified, i.e. without any linked cytotoxic or other moieties, working by, for example, simply binding to target cells and thereby blocking ligand-receptor interaction so as to potentiate NK cell activity, by inactivating the target cells, triggering cell death, or marking target cells for destruction by the immune system. In other embodiments, the therapeutic antibodies will be linked to one or more cytotoxic moieties. It will be appreciated that this description of the contents of the kits is not limiting in any way. For example, for the therapeutic antibodies, the kit may contain any combination of unmodified or cytotoxic antibodies. In addition, the kit may contain other types of therapeutic compounds as well, such as chemotherapeutic or anti-proliferative agents. Preferably, the kits also include instructions for using the antibodies, e.g., detailing the herein-described methods for typing NK receptor status in patients and administering therapeutic antibodies accordingly.

In addition, the treatment may involve multiple rounds of therapeutic (e.g. cytotoxic) antibody administration. For example, following an initial round of antibody administration, the overall number of disease cells (e.g. tumor or proliferating cells) in the patient can be re-measured, and, if still elevated, an additional round of 4Ig-B7-H3 status typing can be performed, followed by an additional round of therapeutic antibody administration. It will be appreciated that the antibodies administered in this additional round of administration will not necessarily be identical to those used in the initial round.

The invention provides methods of potentiating NK cell activity in a patient in need thereof, comprising the step of administering a composition according to this invention to said patient. The method is more specifically directed at increasing NK cell activity in patients having a disease in which increased NK cell activity is beneficial, which involves, affects or is caused by cells susceptible to lysis by NK cells, or which is caused or characterized by insufficient NK cell activity, such as a cancer, another proliferative disorder, an infectious disease or an immune disorder. More specifically, the methods of the present invention are utilized for the treatment of a variety of cancers and other proliferative diseases including, but not limited to, carcinoma, including that of the bladder, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xeroderma pigmentosum, keratoacanthoma, seminoma, thyroid follicular cancer and teratocarcinoma. Preferred disorders that can be treated according to the invention include hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sezary syndrome (SS); Adult T-cell leukemia lymphoma (ATLL); a/d T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic (Ki 1+) large cell lymphoma; intestinal T-cell lymphoma; T-lymphoblastic; and lymphoma/leukemia (T-Lbly/T-ALL).

Other proliferative disorders can also be treated according to the invention, including for example hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty. The compounds and methods of this invention can be used to treat or prevent infectious diseases, including preferably any infections caused by viruses, bacteria, protozoa, molds or fungi. The compounds can furthermore be used to treat or prevent any disorder involving cells which express a 4Ig-B7-H3 polypeptide.

Pharmaceutical Compositions

The invention also provides compositions, e.g., pharmaceutical compositions, that comprise any of the present antibodies, including fragments and derivatives thereof, in any suitable vehicle in an amount effective for potentiation of NK cell activity, the treatment of disease, or to inhibit the proliferation or activity of, or to kill, cells expressing 4Ig-B7-H3 in patients. The composition generally further comprises a pharmaceutically acceptable carrier. It will be appreciated that the present methods of administering antibodies and compositions to patients can also be used to treat animals, or to test the efficacy of any of the herein-described methods or compositions in animal models for human diseases.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, ophthalmically, by nasal aerosol or inhalation. Such compositions are prepared according to techniques well-known in the art of pharmaceutical formulation.

In one embodiment, the antibodies of this invention may be incorporated into liposomes ("immunoliposomes"), alone or together with another substance for targeted delivery to a patient or an animal. Such other substances can include nucleic acids for the delivery of genes for gene therapy or for the delivery of antisense RNA, RNAi or siRNA for suppressing a gene in an NK cell, or toxins or drugs for the activation of NK cells through other means, or any other agent described herein that may be useful for activation of NK cells or targeting of tumor or infected cells.

In another embodiment, the antibodies of the invention can be modified to improve its bioavailability, half life in vivo, etc. For example, the antibodies can be pegylated, using any of the number of forms of polyethylene glycol and methods of attachment known in the art (see, e.g., Lee et al. (2003) Bioconjug Chem. 14(3):546-53; Harris et al. (2003) Nat Rev Drug Discov. 2(3):214-21; Deckert et al. (2000) Int J Cancer. 87(3):382-90).

Several monoclonal antibodies have been shown to be efficient in clinical situations, such as Rituxan (Rituximab), Herceptin (Trastuzumab) Xolair (Omalizumab), Bexxar (Tositumomab), Campath (Alemtuzumab), Zevalin, Oncolym and similar administration regimens (i.e., formulations and/or doses and/or administration protocols) may be used with the antibodies of this invention. Schedules and dosages for administration can be determined in accordance with known methods for these products, for example using the manufacturers' instructions. For example, a monoclonal antibody can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody of the invention may between about 10 mg/m2 and 500 mg/m2. However, it will be appreciated that these schedules are exemplary and that optimal schedule and regimen can be adapted taking into account the affinity of the antibody and the tolerability of the antibodies that must be determined in clinical trials.

According to another embodiment, the antibody compositions of this invention may further comprise one or more additional therapeutic agents, including agents normally utilized for the particular therapeutic purpose for which the antibody is being administered. The additional therapeutic agent will normally be present in the composition in amounts typically used for that agent in a monotherapy for the particular disease or condition being treated. Such therapeutic agents include, but are not limited to, therapeutic agents used in the treatment of cancers, therapeutic agents used to treat infectious disease, therapeutic agents used in other immunotherapies, cytokines (such as IL-2 or IL-15), other antibodies and fragments of other antibodies. So long as a particular therapeutic approach is not known to be detrimental to the patient's condition in itself, and does not significantly counteract the NK cell receptor antibody-based treatment, its combination with the present invention is contemplated.

In connection with solid tumor treatment, the present invention may be used in combination with classical approaches, such as surgery, radiotherapy, chemotherapy, and the like. The invention therefore provides combined therapies in which humanized or human-suitable antibodies against NK cell receptors are used simultaneously with, before, or after surgery or radiation treatment; or are administered to patients with, before, or after conventional chemotherapeutic, radiotherapeutic or anti-angiogenic agents, or targeted immunotoxins or coaguligands. The NK cell receptor antibody-based therapeutic and anti-cancer agents may be administered to the patient simultaneously, either in a single composition, or as two distinct compositions using different administration routes.

When one or more agents (e.g., anti-cancer or other NK potentiating agent) are used in combination with the present antibody-based therapy, there is no requirement for the combined results to be additive of the effects observed when each treatment is conducted separately. Although at least additive effects are generally desirable, any increased anti-cell proliferation effect above one of the single therapies would be of benefit. Also, there is no particular requirement for the combined treatment to exhibit synergistic effects, although this is certainly possible and advantageous. The therapeutic anti-4Ig-B7-H3 or anti-4Ig-B7-H3R antibody-based treatment may precede, or follow, the other treatment by, e.g., intervals ranging from minutes to weeks and months. It also is envisioned that more than one administration of either the therapeutic antibody-based composition or the other agent will be utilized. The agents may be administered interchangeably, on alternate days or weeks; or a cycle of anti-4Ig-B7-H3 or anti-4Ig-B7-H3R antibody-based treatment may be given, followed by a cycle of other therapy. In any event, to achieve inhibition of cell overproliferation using a combined therapy, all that is required is to deliver both agents in a combined amount effective to exert an anti-proliferative effect, irrespective of the times for administration. The same principles will apply to the treatment of infected cells in infectious disease and proliferating immune cells in inflammatory conditions.

In other aspects, immunomodulatory compounds or regimens may be practiced in combination with the present invention. Preferred examples include treatment with cytokines. Various cytokines may be employed in such combined approaches. Examples of cytokines include IL-1alpha IL-1beta, IL-2, IL-3, IL-4, IL-5, IL-6, IL-7, IL-8, IL-9, IL-10, , IL-11, IL-12, IL-13, IL-15, IL-21, TGF-beta, GM-CSF, M-CSF, G-CSF, TNF-alpha, TNF-beta, LAF, TCGF, BCGF, TRF, BAF, BDG, MP, LIF, OSM, TMF, PDGF, IFN-alpha, IFN-beta, IFN-gamma. Cytokines are administered according to standard regimens, consistent with clinical indications such as the condition of the patient and the relative toxicity of the cytokine.

Other preferred examples of compounds or regimens that may be practiced in combination with those of the present invention include compositions modulating the activity of NK cells. For example, in certain, preferred embodiments, the antibodies of the present invention will be administered in conjunction with compounds capable of blocking inhibitory NK cell receptors, such as natural ligands, antibodies or small molecules that can inhibit the activity of CD94/NKG2A receptors or inhibitory KIR receptors such as KIR2DL1, KIR2DL2, KIR2DL3, KIR3DL1, and KIR3DL2 (see, e.g., PCT Patent Application no. PCT/FR 04/01702 filed Jul. 1, 2004, titled "Compositions and methods for regulating NK cell activity, Yawata et al. (2002) Crit Rev Immunol. 22(5-6): 463-82; Middleton et al. (2002) Transpl Immunol. 10(2-3): 147-64; Vilches et al. (2002) Armu Rev Immunol.20:217-51; or Long et al. 2001 Immunol Rev. 181:223-33), the disclosures of each of which are herein incorporated by reference in their entireties). Alternatively, agonists of activating NK cell receptors, can also be used. Said agonist may stimulate any activating receptor of a NK cell, e.g. NKp30 (see, e.g., PCT WO 01/36630, the disclosure of which is herein incorporated by reference in its entirety), NKp44 (see, e.g., Vitale et al. (1998) J. Exp. Med. 187:2065-2072, the disclosure of which is herein incorporated by reference in its entirety), NKp46 (see, e.g., Sivori et al. (1997) J. Exp. Med. 186:1129-1136; Pessino et al. (1998) J. Exp. Med. 188:953-960; the disclosures of which are herein incorporated by reference in their entireties), NKG2D (see, e.g., OMIM 602893), IL-2R, IL-12R, IL-15R, IL-18R, IL-21R, or an activatory KIR receptor, for example a KIR2DS4 receptor (Carrington and Norman, The KIR Gene Cluster, May 3, 2003, available at: www.ncbi.nlm.nih.gov/books), or any other receptor present on a substantial fraction of NK cells, and whose activation leads to the activation or proliferation of the cell, preferably even if the cell had previously been inhibited via an inhibitory receptor such as an inhibitory KIR receptor. See e.g. US patent application no. 60/567,058 filed Apr. 30, 2004, the disclosure of which is incorporated herein by reference.

In a typical example, a cytokine (for example IL-2, IL-12, IL-15, IL-18 or IL-21) is administered daily for a period of 5-10 days, the cytokine(s) being first injected on the same day as the first injection of the compound which inhibits 4Ig-B7-H3R activity or blocks an interaction of 4Ig-B7-H3 and 4Ig-B7-H3R. Said method preferably comprises one or two injections/day of cytokine(s) by subcutaneous route. The dosage of the cytokine will be chosen depending on the condition of the patient to be treated. In preferred examples, a relatively low dose of cytokine can be used. For example, an effective dose of a cytokine such as IL-2 is typically lower than 1 million units/square meters/day of cytokine(s), when the cytokine-containing pharmaceutical composition is used for daily subcutaneous injection. In a preferred example, IL-2 is injected subcutaneously at daily doses below 1 million units/m$^2$ for 5 to 10 days. Further detail of the use of cytokines is described in International Patent publication no. PCT/EP/0314716 and U.S. patent application No. 60/435,344 titled "Pharmaceutical compositions having an effect on the proliferation of NK cells and a method using the same", the disclosures of which are incorporated herein by reference. Cytokines can be administered according to the manufacturer's instructions, and modification to dosage and administration can be made as described herein with respect to therapeutic antibodies.

As chemotherapy is often used to treat proliferative disorders, the NK cell receptor antibody therapeutic compositions of the present invention may be administered in combination with other chemotherapeutic or hormonal therapy agents. A variety of hormonal therapy and chemotherapeutic agents may be used in the combined treatment methods disclosed herein. Chemotherapeutic agents contemplated as exemplary include alkylating agents, antimetabolites, cytotoxic antibiotics, vinca alkaloids, for example adriamycin, dactinomycin, mitomycin, carminomycin, daunomycin, doxorubicin, tamoxifen, taxol, taxotere, vincristine, vinblastine, vinorelbine, etoposide (VP-16), 5-fluorouracil (5FU), cytosine arabinoside, cyclophosphamide, thiotepa, methotrexate, camptothecin, actinomycin-D, mitomycin C, cisplatin (CDDP), aminopterin, combretastatin(s) and derivatives and prodrugs thereof. Hormonal agents include for example LHRH agonists such as leuprorelin, goserelin, triptorelin, and buserelin; anti-estrogens such as tamoxifen and toremifene; anti-androgens such as flutamide, nilutamide, cyproterone and bicalutamide; aromatase inhibitors such as anastrozole, exemestane, letrozole and fadrozole; and progestagens such as medroxy, chlormadinone and megestrol.

As will be understood by those of ordinary skill in the art, the appropriate doses of chemotherapeutic agents will be generally around those already employed in clinical therapies wherein the chemotherapeutics are administered alone or in combination with other chemotherapeutics. By way of example only, agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Further useful agents include compounds that interfere with DNA replication, mitosis and chromosomal segregation, and agents that disrupt the synthesis and fidelity of polynucleotide precursors may also be used. A number of exemplary chemotherapeutic agents for combined therapy are listed in Table C of U.S. Pat. No. 6,524,583, the disclosure of which agents and indications are specifically incorporated herein by reference. Each of the agents listed are exemplary and not limiting. Another useful source is "Remington's Pharmaceutical Sciences" 15th Edition, chapter 33, in particular pages 624-652. Variation in dosage will likely occur depending on the condition being treated. The physician administering treatment will be able to determine the appropriate dose for the individual subject.

The present antibodies may also be used in combination with any one or more anti-angiogenic therapies. Examples of such agents include neutralizing antibodies antisense strategies, RNA aptamers and ribozymes against VEGF or VEGF receptors (U.S. Pat. No. 6,524,583, the disclosure of which is incorporated herein by reference). Variants of VEGF with antagonistic properties may also be employed, as described in WO 98/16551, specifically incorporated herein by reference. Further exemplary anti-angiogenic agents that are useful in connection with combined therapy are listed in Table D of U.S. Pat. No. 6,524,583, the disclosure of which agents and indications are specifically incorporated herein by reference.

The present antibodies may also be advantageously combined with methods to induce apoptosis. For example, a number of oncogenes have been identified that inhibit apoptosis, or programmed cell death. Exemplary oncogenes in this category include, but are not limited to, bcr-abl, bcl-2 (distinct from bcl-1, cyclin D1; GenBank accession numbers M14745, X06487; U.S. Pat. Nos. 5,650,491; and 5,539,094; each incorporated herein by reference) and family members including Bcl-x1, Mcl-1, Bak, A1, A20. Overexpression of bcl-2 was first discovered in T cell lymphomas. bcl-2 functions as an oncogene by binding and inactivating Bax, a protein in the apoptotic pathway. Inhibition of bcl-2 function prevents inactivation of Bax, and allows the apoptotic pathway to proceed. Inhibition of this class of oncogenes, e.g., using antisense nucleotide sequences or small molecule chemical compounds, is contemplated for use in the present invention to give enhancement of apoptosis (U.S. Pat. Nos. 5,650,491; 5,539,094; and 5,583,034; each incorporated herein by reference).

Therapies involving the antibodies of the invention may also be used in combination with adjunct compounds. Adjunct compounds may include by way of example anti-emetics such as serotonin antagonists and therapies such as phenothiazines, substituted benzamides, antihistamines, butyrophenones, corticosteroids, benzodiazepines and cannabinoids; bisphosphonates such as zoledronic acid and pamidronic acid; and hematopoietic growth factors such as erythropoietin and G-CSF, for example filgrastim, lenograstim and darbepoietin.

Increasing the Efficacy of Antibodies that Induce Cell Lysis Via ADCC

In particularly preferred aspects, the NK cell potentiating compounds of the invention can be used in combination with a second antibody, particularly an antibody capable of inducing lysis of a target cell to which it is bound via an ADCC mechanism. As demonstrated in U.S. patent application No. 60/489,489, filed Jul. 24, 2003, titled "Methods and compositions for increasing the efficiency of therapeutic antibodies using compounds that block the inhibitory receptors of NK cells", the disclosure of which is incorporated herein by reference, compounds such as anti-Ig4-B7-H3 and anti-Ig4-B7-H3R antibodies may be used to increase the efficacy of such second antibody, or to reduce the dosage of or modify the treatment regimen for such second antibody.

The compounds, particularly antibodies, of the invention that potentiate NK cell activity may be used advantageously to enhance the ADCC mechanism in vivo, when a second therapeutic antibody is administered to an individual. Indeed, the present invention provides novel compositions and methods that overcome the current difficulty related to the efficacy of therapeutic antibodies. In some cases, NK cells from an individual may have poor therapeutic mAb (monoclonal antibody)-mediated ADCC because of a lack of activation of NK cells, e.g., by an inhibition by 4Ig-B7-H3 of a counterpart (inhibitory) receptor on NK cells. Preferably, an increase of the ADCC mechanism is achieved by the administration of compounds that inhibit a 4Ig-B7-H3 receptor, preferably by administration of an antibody that blocks an interaction of 4Ig-B7-H3 and 4Ig-B7-H3R on natural killer cells, thereby promoting a potentiation of natural killer cell cytotoxicity in mammalian subjects.

More specifically, the invention discloses methods of treatments of a subject in which a compound, preferably an antibody or a fragment thereof, that inhibits 4Ig-B7-H3R activity or blocks an interaction of 4Ig-B7-H3 and 4Ig-B7-H3R, is co-administered with the second therapeutic antibody to the subject. The inventors demonstrate here that the efficiency of the second therapeutic antibody can be greatly enhanced by the co-administration, e.g., co-injection, of such a compound, preferably an antibody or a fragment thereof, that overcomes the inhibition of NK cells, e.g. by blocking the inhibitory 4Ig-B7-H3R protein of an NK cell.

The invention also concerns pharmaceutical compositions comprising a compound, preferably an antibody or a fragment thereof, that inhibits 4Ig-B7-H3R activity or blocks an interaction of 4Ig-B7-H3 and 4Ig-B7-H3R, and a second therapeutic antibody. The invention also concerns kits comprising a second therapeutic antibody and a compound, preferably an antibody or a fragment thereof, that inhibits 4Ig-B7-H3R activity or blocks an interaction of 4Ig-B7-H3 and 4Ig-B7-H3R.

The invention also concerns the use of a compound, preferably an antibody or a fragment thereof, that inhibits 4Ig-B7-H3R activity or blocks an interaction of 4Ig-B7-H3 and 4Ig-B7-H3R, for increasing the efficiency of a treatment with a therapeutic antibody, or for increasing ADCC in a subject submitted to a treatment with a therapeutic antibody.

The invention also concerns the use of a compound, preferably an antibody or a fragment thereof, that inhibits 4Ig-B7-H3R activity or blocks an interaction of 4Ig-B7-H3 and 4Ig-B7-H3R, and of a second therapeutic antibody for the preparation of a drug for treating a disease. More particularly, the treatment of the disease requires the depletion of the targeted cells, preferably the diseased cells such as virally-infected cells, tumor cells or other pathogenic cells. Preferably, the disease is a cancer, infectious or immune disease. More preferably, the disease is selected from the group consisting of a cancer, an auto-immune disease, an inflammatory disease, and a viral disease. The disease also concerns a graft rejection, more particularly allograft rejection, and graft versus host disease (GVHD).

Said second antibody or therapeutic antibody will generally be an antibody which induces ADCC by binding to a (i) target antigen to be depleted, and (ii) CD16 present on NK cells. The present invention thus also comprises a method for reducing the dosage of a second therapeutic antibody, e.g. an antibody that is bound by an Fcγ receptor, preferably CD16 (FcγRIIIa). For example, co-administration of a second therapeutic antibody and a compound that inhibits 4Ig-B7-H3R activity or blocks an interaction of 4Ig-B7-H3 and 4Ig-B7-H3R allows a lower dose of the therapeutic antibody to be used. Such second antibody can be used at a 20%, 30%, 40%, 50%, 60%, 70%, 80%, 90%, or lower dose than the recommended dose in the absence of the compound.

In addition, the invention provides a method for determining a therapeutically-effective, reduced dose of a second therapeutic antibody, e.g., an antibody bound by CD16, the method comprising i) co-incubating a first concentration of the second therapeutic antibody with target cells and NK cells, and in the absence of a compound that inhibits 4Ig-B7-H3R activity or blocks an interaction of 4Ig-B7-H3 and 4Ig-B7-H3R; ii) co-incubating a second, lower concentration of the second therapeutic antibody with target cells, with NK cells, and in the presence of a compound that inhibits 4Ig-B7-H3R activity or blocks an interaction of 4Ig-B7-H3 and 4Ig-B7-H3R; iii) determining if the depletion of target cells observed in step ii) is as great as the depletion observed in step i). If it is observed that step ii) is as efficacious as step i), then the relative concentrations of the compound and the second therapeutic antibody can be varied, and depletion observed, in order to identify different conditions that would be suitable for use in a given patient, e.g., maximizing target cell depletion, lowered dose of second therapeutic antibody, or lowered dose of the compound, depending on the particular needs of the patient.

In a particular aspect, the present invention provides a method of treatment of a disease in a human subject in need thereof, comprising: a) administering to said subject a compound that inhibits 4Ig-B7-H3R activity or blocks an interaction of 4Ig-B7-H3 and 4Ig-B7-H3R; and, b) administering to said subject a second therapeutic antibody that can be bound by CD16.

In one embodiment, the second therapeutic antibody and compound are administered to the subject simultaneously. In another embodiment, the second therapeutic antibody is administered to the subject before or after administration of the compound. In another embodiment, the compound is administered to the subject within one week, within 4 days, within 3 days or on the same day (e.g. within about 24 hours) of the administration of the second therapeutic antibody. In another embodiment, the disease is a cancer, infectious or immune disease.

In one embodiment, the method further comprises an additional step in which the activity or number of NK cells in the subject is assessed prior or subsequent to the administration of the compound. In another embodiment, the additional step involves i) obtaining NK cells from the subject prior to the administration; ii) incubating the NK cells in the presence of one or more target cells that are recognized by the therapeutic antibody, in the presence or absence of the compound; and iii) assessing the effect of the compound on the ability of the NK cells to deplete the target cells; wherein a detection that the compound enhances the ability of the NK cells to deplete the target cells indicates that the compound is suitable for use in the method, and that the method is suitable for use with the subject.

In another aspect, the present invention provides a pharmaceutical composition comprising a second therapeutic antibody, e.g. that can be bound by CD16, a compound that inhibits 4Ig-B7-H3R activity or blocks an interaction of 4Ig-B7-H3 and 4Ig-B7-H3R, and pharmaceutically acceptable carrier. In another aspect, the present invention provides a kit comprising a second therapeutic antibody, e.g. that can be bound by CD16, and one or more compounds that inhibit 4Ig-B7-H3R activity or blocks an interaction of 4Ig-B7-H3 and 4Ig-B7-H3R.

For any of the above-mentioned methods, compositions, or kits, in one embodiment the second therapeutic antibody comprises a human IgG1 or an IgG3 Fc portion. In another embodiment, the compound is an anti-Ig4-B7-H3 or anti-Ig4-B7-H3R antibody or a fragment thereof. In another embodiment, the therapeutic antibody is a monoclonal antibody or fragment thereof. In another embodiment, the therapeutic antibody is not conjugated with a radioactive or toxic moiety. In another embodiment, the compound inhibits an inhibitory receptor of an NK cell. In another embodiment, the compound stimulates an activating receptor of an NK cell. In another embodiment, the compound is a human, humanized or chimeric antibody, or a fragment thereof. In one embodiment, the therapeutic antibodies or compounds can be antibody fragments or derivatives such as, inter alia, a Fab fragment, a Fab'2 fragment, a CDR and a ScFv.

Therefore, the invention concerns a method of treatment of a disease in a subject in need thereof comprising:

d) administering to said subject a compound, preferably an antibody or a fragment thereof, that inhibits 4Ig-B7-H3R activity or blocks an interaction of 4Ig-B7-H3 and 4Ig-B7-H3R; and, e) administering to said subject a therapeutic antibody.

Said therapeutic antibody is preferably an antibody that can be bound by CD16 of NK cells, preferably through its Fc region.

Preferably, said therapeutic antibody that can be used in combination with the NK-potentiating compounds of the invention has a human IgG1 or an IgG3 Fc portion, particularly a monoclonal antibody or a fragment thereof, further preferably a humanized, human or chimeric antibody or a fragment thereof, for instance rituximab.

In one embodiment, the antibody that can be used in combination with the NK-potentiating compounds of the invention is specifically recognized by an Fc gamma receptor such as FCGR3A (also called CD16, FCGR3, Immunoglobulin G Fc Receptor III; IGFR3, Receptor for Fc Fragment of IgG, Low Affinity IIIa,; see, e.g. OMIM 146740), FCGR2A (also called CD32, CDw32, Receptor for Fc Fragment of IgG, Low Affinity IIa, FCG2, Immunoglobulin G Fc Receptor II; see, e.g. OMIM 146790); FCGR2B (also called CD32, Receptor for Fc Fragment of IgG, Low Affinity IIb; FCGR2B, FC-Gamma-RIIB; see, e.g. OMIM 604590), FCG1RA (also called CD64; Receptor for Fc Fragment of IgG, High affinity Ia; IGFR1; see, e.g., OMIM 146760); FCGR1 fragment of IgG, High affinity Ic, Immunoglobulin G Fc receptor IC, IGFRC; see, e.g., OMIM 601503); or FCGR1B (also called CD64, Receptor for Fc Fragment of IgG, High affinity Ib; Immunoglobulin G Fc Receptor IB,; IGFRB; see, e.g., OMIM 601502).

Typical examples of therapeutic antibodies that can be used in combination with the NK-potentiating compounds of the invention are rituximab, alemtuzumab and trastuzumab. Such antibodies may be used according to clinical protocols that have been authorized for use in human subjects. Additional specific examples of therapeutic antibodies include, for instance, epratuzumab, basiliximab, daclizumab, cetuximab, labetuzumab, sevirumab, tuvurimab, palivizumab, infliximab, omalizumab, efalizumab, natalizumab, clenoliximab, etc. Optionally, when a compound that stimulates an activating receptor of a NK cell is a cytokine, the therapeutic antibody is an antibody other than rituximab or herceptin, or optionally other than an anti-CD20 or anti-HER2/neu antibody. Other examples of preferred therapeutic antibodies for use in accordance with the invention include anti-ferritin antibodies (US Patent Publication no. 2002/0106324), anti-p140 and anti-sc5 antibodies (WO 02/50122), and anti-KIR (killer inhibitory receptor) antibodies (The KIR receptors are described in Carrington and Norman, *The KIR Gene Cluster*, May 3, 2003, available at: http://www.ncbi.nlm.nih.gov/books), the disclosures of each of the above reference being incorporated herein by reference. Other examples of therapeutic antibodies are listed in the following table, any of which (and others) can be used in the present methods. It will be appreciated that, regardless of whether or not they are listed in the following table or described elsewhere in the present specification, any antibody that can deplete target cells, preferably by ADCC, can benefit from the present methods, and that the following Table 2 is non exhaustive, neither with respect to the antibodies listed therein, nor with respect to the targets or indications of the antibodies that are listed.

TABLE 2

Therapeutic antibodies for use in combination with NK-potentiating compounds of the invention

| Ab specificity | DCI | Commercial name | Typical Indications |
|---|---|---|---|
| Anti-CD20 | rituximab | MabThera ®, Rituxan ® | NHL B |
| Anti-CD20 | | Zevalin | NHL |
| Anti-CD20 | | Bexocar | NHL |
| Anti-CD52 | alemtuzumab | CAMPATH-1H ® | CLL, allograft |
| Anti-CD33 | | SMART-M195 | AML |
| Anti-CD33 | | Zamyl ™ | Acute myeloid Leukemia |
| Anti-HLA-DR antigen | | SMART-ID10 | NHL |
| Anti-HLA-DR | | Remitogen ™ | NHL B |
| Anti-CD22 | epratuzumab | LymphoCide ™ | NHL B |
| Anti-HER2 | | MDX-210 | Prostate and other cancers |
| Anti-erbB2 (HER-2/neu) | trastuzumab | Herceptin ®, | Metastatic breast cancer |
| Anti-CA125 | | OvaRex | Ovarian cancer |
| Anti-MUC1 | | TriAb | Metastatic breast cancer |
| Anti-MUC1 | | BravaRex | Metastatic cancers |
| Anti-PEM antigen | | Theragyn, Therex | Ovarian cancer, breast cancer |
| Anti-CD44 | bivatuzumab | | Head and neck cancer |
| Anti-gp72 | MAb, idiotypic 105AD7 | | colorectal cancer |
| Anti-EpCAM | Anti-EpCAM; MT201 | IS-IL2 | cancer |
| Anti-VEGF | MAb-VEGF | | metastatic NSCLC, colorectal cancer |
| Anti-CD18 | AMD Fab | | age-related macular degeneration |
| Anti-CD18 | Anti-CD18 | | Myocardial infarction |
| Anti-VEGF receptor | IMC-1cl I | | colorectal cancer |
| anti-nuC242 | nuC242-DMI | | Colorectal, gastric, and pancreatic cancer |
| Anti-EGFR | MAb425 | | cancer |
| Anti-EGFR | ABX-EGF | | Cancer |
| Anti-EGFR (HER-1, erbB1) | cetuximab | | ENT and colorectal Cancers |
| Anti-MUC-1 | | Therex ® | Breast and epithelial cancers |
| Anti-CEA | | CEAVac | Colorectal cancer |
| Anti-CEA | labetuzumab | CEA-Cide ™ | Solid tumors |
| Anti-αVβ3 | | Vitaxin | Leiomyosarcoma, colorectal and other cancers (anti-angiogenic) |
| Anti-KDR (VEGFR2) | | | Cancers (anti-angiogenic) |
| anti-VRS fusion protein | palivizumab | Synagis ® | Viral diseases |

TABLE 2-continued

Therapeutic antibodies for use in combination with NK-potentiating compounds of the invention

| Ab specificity | DCI | Commercial name | Typical Indications |
| --- | --- | --- | --- |
| Idem | | Numax ™ | Idem |
| CMV | sevirumab | Protovir | CMV Infection |
| HBs | tuvirumab | Ostavir ™ | Hepatitis B |
| Anti-CD25 | basiliximab | Simulect ® | Prevention/treatment allograft rejection |
| Anti-CD25 | daclizumab | Zenapax ® | Prevention/treatment allograft rejection |
| anti-TNF-α | infliximab | Remicade ™ | Crohn disease, rheumatoid arthritis |
| anti-CD80 | IDEC-114 | | psoriasis |
| anti-IgE | | E-26 | Allergic asthma and rhinitis |
| anti-IgE | omalizumab | Xolair ™ | Asthma |
| anti-IgE | Rhu-mAb E25 | | Allergy/asthma |
| anti-integrin αL (CD11a, LFA-1) | efalizumab | Xanelim ™ | psoriasis |
| Anti-beta 2 integrin | LDP-01 | | Stroke, allograft rejection |
| anti-integrin αL (CD11a, LFA-1) | anti-CD11a | | psoriasis |
| anti-CD4 | keliximab siplizumab MEDI-507 | | GVHD, psoriasis |
| Anti-CD4 | OKT4A | | Allograft rejection |
| Anti-CD3 | OKT3 | | Allograft rejection |
| Anti-CD3 | SMART-aCD3 | | Autoimmune disease, allograft rejection, psoriasis |
| Anti-CD64 | | | anemia |
| anti-CD147 | | | GvHD |
| anti-integrin α4 (α4β1-α4β7) | natalizumab | Antegren ® | Multiple Sclerosis, Crohn |
| Anti-integrin β7 | | | Crohn, ulcerative colitis |
| Alpha 4 beta 7 | LDP-02 | | Ulcerative colitis |
| Anti-HLA-DR10 beta | | Oncolym | NHL |
| Anti-CD3 | | Nuvion | T cell malignancies |
| Anti-GD2 ganglioside | | Trigem | Metastatic melanoma and small cell lung cancer |
| Anti-SK-1 antigen | | | Colorectal and pancreatic carcinoma |
| anti-CD4* | clenoliximab | | |
| anti-IL-8 | ABX-IL8 | | psoriasis |
| Anti-VLA-4 | | Antegren | MS |
| Anti-CD40L | | Antova | SLE, allograft rejection |
| Anti-CD40L | IDEC-131 | | MS, SLE |
| Anti-E-selectin | CDP850 | | psoriasis |
| Anti-CD11/CD18 | Hu23F2G | | MS, stroke |
| Anti-ICAM-3 | ICM3 | | psoriasis |
| Anti-CBL | ABX-CBL | | GVHD |
| Anti-CD147 | | | |
| Anti-CD23 | IDEC-152 | | Asthma, allergies |
| Anti-CD25 | | Simulect | Allograft rejection |
| Anti-T1-ACY | ACY-110 | | Breast cancer |
| Anti-TTS | TTS-CD2 | | Pancreatic, renal cancer |
| Anti-TAG72 | AR54 | | Breast, ovarian, lung cancer |
| Anti-CA19.9 | GivaRex | | Colorectal, pancreatic, gastric |
| Anti-PSA | ProstaRex | | Prostate cancer |
| Anti-HMFG1 | R1550 | | Breast, gastric cancer |
| | pemtumomab | Theragyn | Gastric, ovarian cancer |
| Anti-hCG | CTP-16, CTP-21 | | Mutiple cancers |
| Anti collagen Types 1-V | HU177; HUIV26; XL313 | | Multiple cancers |
| Anti-CD46 | | Crucell/J&J | Mutiple cancers |
| Anti-17A-1 | Edrecolomab | Panorex | Colorectal cancer |
| Anti-HM1.24 | AHM | | Multiple myeloma |
| Anti-CD38 | Anti-CD38 | | Multiple myeloma |
| Anti-IL15 Receptor | HuMax lymphoma | | Lymphoma |

TABLE 2-continued

Therapeutic antibodies for use in combination with NK-potentiating compounds of the invention

| Ab specificity | DCI | Commercial name | Typical Indications |
|---|---|---|---|
| Anti-IL6 | B-E8 | | Lymphoma |
| Anti-TRAIL-R1 | TRM-1 | | Mutiple cancers |
| Anti-VEGF2 | | | Mutiple cancers |
| Anti-BlyS | Lymphostat | | Mutiple cancers |
| Anti-SCLC, CEA and DTPA | Pentacea | | Lung cancer |
| Anti-CD52 | CAMPATH | | Leukemia, Lymphoma |
| Anti-Lewis Y antigen | IGN311 | | Epithelial cancers |
| Anti-VE cadherin | E4G10 | | Mutiple cancers |
| Anti-CD56 | BB10901, huN901DC1 | | Colorectal, lung cancer |
| Anti-mertansine/mucine | Cantuzumab | | Colorectal, lung, pancreatic cancer |
| Anti-AFP | AFP-cide | | Liver cancer |
| Anti-CSAp | Mu-9 | | Colorectal cancer |
| Anti-CD30 | MDX-060 | | Melanoma, Hodgkins Disease |
| Anti-PSMA | MDX-070 | | Prostate cancer |
| Anti-CD15 | MDX-11 | | Leukemia |
| Anti-TAG72 | MDX-020 | | Colorectal cancer |
| Anti-CD19, CD3 bispecific | MT103 | | Lymphoma |
| Anti-mesothelin antigen | SS1-PE38 | | Brain and overian cancer, mesothelioma |
| Anti-DNA and histones | Cotara | | Colorectal, pancreatic, sarcoma, brain and other cancers |
| Anti-a5B1 integrin | Anti-a5 B1 | | Multiple cancers |
| Anti-p97 | SGN17/19 | | Melanoma |
| Anti-CD5 | Genimune | | Leukemia, lymphoma |

In certain preferred examples, the method of the invention comprises one or several injections of two or more compounds that potentiate NK cell activity, preferably by blocking an inhibitory receptor or stimulating an activating receptor of a NK cell. Thus, these two or more compounds can be used in combination. A first of said two or more compounds may be a compound of the invention which inhibits 4Ig-B7-H3R activity or blocks an interaction of 4Ig-B7-H3 and 4Ig-B7-H3R. A second compound may be any of the compounds capable of blocking an inhibitory receptor or stimulating an activating receptor of a NK cell. This to cause an even greater augmentation of ADCC and efficacy of a further therapeutic antibody as discussed below, and/or can reduce the dosage of a particular compound that blocks an inhibitory receptor or stimulates an activating receptor of a NK cell. For example, compounds such as IL -2 are known to be toxic at increased doses. The invention therefore preferably provides a method of treatment of a disease in a subject in need thereof comprising : a) administering to said subject at least two compounds, preferably wherein one or both compounds are an antibody or a fragment thereof, that block an inhibitory receptor or stimulate an activating receptor of a NK cell; and b) administering to said subject a therapeutic antibody. For example, a preferred regimen is where said two compounds are (i) an antibody which inhibits 4Ig-B7-H3R activity or blocks an interaction of 4Ig-B7-H3 and 4Ig-B7-H3R, and (ii) a compound selected from the group consisting of: an antibody which stimulates an NKp30, NKp44, NKp46 or NKG2D receptor, an activatory KIR receptor, an antibody which blocks an inhibitory KIR receptor or NKG2A receptor, IL-2, IL-12, IL-15, IL-18 and IL-21.

Further aspects and advantages of this invention are disclosed in the following experimental section, which should be regarded as illustrative and not limiting the scope of this application.

EXAMPLES

Methods
Monoclonal Antibodies

5B14 mAb (IgM) was obtained by immunizing a 5-week-old BALB/c mouse with ACN (human neuroblastoma) cell line as previously described (Bottino, C., et al., (2003) *J Exp Med.* 198,557-567). c218 (IgG1, anti-CD56), A6-136 (IgM, anti-HLA class I), AZ20 (IgG1, anti-NKp30) were produced in our lab. The following mAbs anti-GD2 (14.G2a, IgG2A) and anti-CD45 (HI30, IgG1) were purchased from BD Biosciences Pharmingen and CALTAG laboratories (Burlingame, Calif.), respectively.

Bone Marrow Aspirates and Neuroblastoma Purification.

After informed consent, bone marrow was aspirated from two iliac crests with a 1.8 gauge needle, from 15 children diagnosed with neuroblastoma, admitted at the Hematology-Oncology Division of the G. Gaslini Institute. Diagnosis and staging were performed according to the International Neuroblastoma Staging System (Brodeur, G.-M., et al. (1993) *J Clin Oncol.* 11, 1466-1477). The amount of bone marrow aspirates residual after performing diagnostic and therapeutic evaluations was analyzed by flow cytometry upon red cells lysis. Neuroblastoma cells were purified from bone marrow aspirates (from children diagnosed with neuroblastoma) by CD45-depletion for Enrichment of Circulating Tumor Cells KIT (RosetteSep, StemCell Technologies, Vancouver, Canada). The investigation was performed after approval by the Gaslini Institute institutional review board.

Detection of GD2 and 5B14 Expression by Immunocytochemistry.

Forty cytospins of 17 mm diameter, containing up to 5×10$^5$ cells/slide, were prepared from BM aspirates. Cytospins were fixed in formalin and incubated with the anti-GD2 monoclonal antibody 14.G2a (5 micrograms/ml BD Pharmigen) or with 5B14 mouse monoclonal antibody (ascitic fluid diluted 1:100) for 30 minutes. One slide was incubated with an isotype-matched monoclonal antibody of irrelevant specificity (negative control). After washing, slides were sequentially incubated with a rabbit antimouse antibody (DAKO A/S, Denmark) diluted 1:20 for 30 minutes and an alkaline phosphatase and mouse monoclonal anti-alkaline phosphatase (APAAP) complex diluted 1:20 (DAKO) for 30 minutes. Alkaline-phosphatase substrate (DAKO Fuchsine) was subsequently added as chromogen. The slides were counterstained in hematoxylin and then cover-slipped. The results were interpreted under light microscope.

Biochemical Characterization and Purification of 5B14-Reactive Molecule.

The 5B14 mAb (IgM) was purified using Kaptiv-M (Tecnogen S.C.p.A. Caserta, Italy). 20×106 cells were labeled with 125I (NEN, Boston, Mass.), lysed in 1% NP-40 and immunoprecipitated with Sepharose-CnBr-(Pharmacia Biotech Inc. Piscataway, N.J.) coupled 5B14 mAb. Samples were analyzed by discontinuous SDS-PAGE either undigested or digested with N-glycosidase F (Boehringer Mannheim, GmbH, Germany). 293T cell membranes obtained as previously described (Bottino, C., et al., (2003)) were incubated with Sepharose CnBr-coupled 5B14 mAb. Specific proteins were eluted and upon concentration, analyzed by SDS-PAGE under non-reducing conditions. The Polyacrylamide gel was stained using Simply Blue Safestain (Invitrogen, Paisley, UK) (Bottino, C., et al., (2003)).

In-Gel Enzymatic Digestion and LC/ESI-MS/MS Analysis of Tryptic Peptides.

In-gel digestion of the purified 5B14-reactive protein stained was carried out as previously described (Bottino, C., et al., (2003)). Analysis of the resulting peptide mixtures was performed by LCQ-DECA MS/MS ion trap mass spectrometer coupled to a HPLC Surveyor (Thermo Finnigan) and equipped with a 1×150 mm column, Vydac C18, 5 µm, 300 Å (Dionex Company, San Francisco, Calif., USA) as described (Bottino, C., et al., (2003)). Computer analysis of peptide MS/MS spectra was performed using the version 1.2 of the TurboSEQUEST software (University of Washington, licensed to ThermoFinnigan Corp.) and searched against the National Center for Biotechnology Information (NCBI) human protein database.

RT-PCR Amplification of cDNAs Encoding Human 4Ig-B7-H3 and 2Ig-B7-H3.

Total RNA extracted using peQGold RNA pure (peQLab, Erlangen, Germany) from 293T cell line was reverse transcribed by standard technique using oligo (dT) priming. Primers used were 5' ATGCTGCGTCGGCGGGG (2Ig-B7-H3 UP) (SEQ ID NO 3) and 5' GGTCAGGCTATTTCT-TGTCCATC (B7-H3 DW) (SEQ ID NO 4) for 2Ig-B7-H3 and 5'CAGCCGCCTCACAGGAAG (4Ig-B7-H3 UP) (SEQ ID NO 5) and 5' GGTCAGGCTATTTCTTGTCCATC (B7-H3 DW) (SEQ ID NO 3) for 4Ig-B7-H3. Amplifications were performed with hot start technique, utilizing AmpliTAQ (Perkin Elmer-Applied Biosystems, Foster City, Calif.). 2Ig-B7-H3 amplification (953 bp) was performed for 30 cycles (30 sec. at 94° C., 30 sec. at 55° C., 30 sec. at 72° C.) followed by a 7 min. extension at 72° C. 4Ig-B7-H3 amplification (1624 bp) was performed for 15 cycles (30 sec. at 94° C., 30 sec. at 58° C., 30 sec. at 72° C.), 15 cycles (30 sec. at 94° C., 30 sec. at 55° C., 30 sec. at 72° C.) followed by a 7 min. extension at 72° C. PCR products were subcloned into pcDNA3.1/V5-His-TOPO expression vector (Invitrogen, Carlsbad, Calif.). DNA sequencing was performed using BigDye Terminator Cycle Sequencing Kit and a 377 Applied Biosystems Automatic Sequencer (Perkin Elmer-Applied Biosystems).

Soluble Molecules

2Ig-B7-H3 (RhB7-H3/Fc chimera) was purchased by R&D System, Minneapolis, Minn.). MICA soluble molecule was previously described (Andre P., (2004). *Eur J Immunol.* 34: 961-971). For the 4Ig-B7-H3Fc soluble molecule, the cDNA sequence encoding the extracellular domains (including the leader sequence) of the 4Ig-B7-H3 was amplified from codon 1 to codon 461 and cloned in pRB1 expression vector in frame with the cDNA sequence encoding the mutated hIgG1 as previously described (Falco, M., Marcenaro, E., Romeo, E., Bellora, F., Marras, D., Vely, F., Ferracci, G., Moretta, L., Moretta, A. & Bottino C. (2004). *Eur. J. Immunol.*). The pRB1-4Ig-B7-H3Fcmut construct was transiently transfected into human embryonic fibroblast 293T cell line utilizing Fugene 6 (Roche Monza, Italy). Transfected cells were cultured in DMEM/10% Ultralow IgG fetal calf serum (Invitrogen UK) and supernatants were collected at days 4 and 8 after transfection. 4Ig-B7-H3Fc molecule was purified by affinity chromatography utilizing Protein A Sepharose 4 Fast Flow (Amersham Biosciences). Purified protein was checked by SDS-PAGE followed by silver staining and by ELISA utilizing 5B14 mAb.

Stable Transfection

CHO-K cell line was transfected with pcDNA3.1V5-His-TOPO-2Ig-B7-H3 or pcDNA3.1V5-His-TOPO-4Ig-B7-H3 construct utilizing GenePORTER 2 transfection reagent (GTS, San Diego, Calif.) following manufacturer's instructions. After 48 hrs, transfected cells were selected in DMEM+ 1.5 mg/ml G418 and subcloned under limiting dilution. Selected clones were stained with 5B14 mAb followed by PE-conjugated goat anti-mouse isotype-specific second reagent (Southern Biotechnology Associated, Birmingham, Ala.) and analyzed by flow cytometry using a FACSCalibur (Becton Dickinson).

Polyclonal NK Cells

NK cells were purified using the Human NK Cell Enrichment Cocktail-RosetteSep (StemCell Technologies Inc, Vancouver, BC) and cultured on irradiated feeder cells in the presence of 100 U/ml rIL-2 (Proleukin, Chiron Corp., Emeryville, USA) and 1.5 ng/ml PHA (Gibco Ltd, Paisley, Scotland) in order to obtain polyclonal activated NK cell populations.

Cytolytic Activity and Flow Cytofluorimetric Analysis

NK cells were tested for cytolytic activity against the indicated target cells in a 4-h 51Cr-release assay as previously described (Bottino, C., et al., (2003) *J Exp Med.* 198,557-567). The concentrations of the various mAbs added for masking experiments were 10 µg/ml. The E/T ratios are indicated in the text. For one- or two-color cytofluorimetric analysis (FACSCalibur Becton Dickinson & Co, Mountain View, Calif.) cells were stained with the appropriate mAbs followed by PE- or FITC-conjugated isotype-specific goat anti-mouse second reagent (Southern Biotechnology Associated, Birmingham, Ala.).

IFN-Gamma Production

IFN-gamma production from polyclonal NK cells was measured in supernatants using ELISA (IFN-gamma: BIOSOURCE Int. Inc., California USA). NK cells (5×105 cells/ml) were incubated in 96-well U-bottom tissue culture plates either in the absence or in the presence of purified 2Ig-B7-H3 or 4Ig-B7-H3 (see above) soluble molecules or, as positive controls, in the presence of purified anti-NKp30 mAb (AZ20) or MICA soluble molecule (Andre P., (2004)) at the concentrations of 50 µg/ml or 10 µg/ml, soluble molecules and mAb, respectively.

Results

Isolation of the 5B14 mAb

In an attempt to identify novel cell surface markers expressed by human neuroblastoma cells, mice were immunized with the ACN neuroblastoma cell line. After cell fusion, hybridoma supernatants were screened by indirect immunofluorescence and cytofluorimetric analysis for surface reactivity with a panel of neuroblastoma cell lines. Using this experimental approach, a mAb termed 5B14 was selected that stained not only the immunizing cells but also all the neuroblastoma cell lines tested including SK-N-BE (FIG. 1) and GIMEN (not shown) that do not express the disialoganglioside GD2 presently considered the most reliable marker for neuroblastoma.

We next assessed the surface distribution of the 5B14-reactive molecule(s) on normal cells as well as on tumor cell lines of different histotype. As shown in Table 1 (FIG. 7), 5B14 mAb did not react with either normal lymphocytes or in vitro cultured NK, B and T cell lines. Low reactivity could be detected with monocytes while in vitro induced immature or mature DC (iDC and mDC, respectively) were brightly stained. Finally, 5B14 mAb displayed a high reactivity with a large panel of tumor cell lines of different origin, including melanomas and carcinomas.

Cytofluorimetric Analysis of Fresh Neuroblastoma Bone Marrow Infiltrates

Figure 2A:
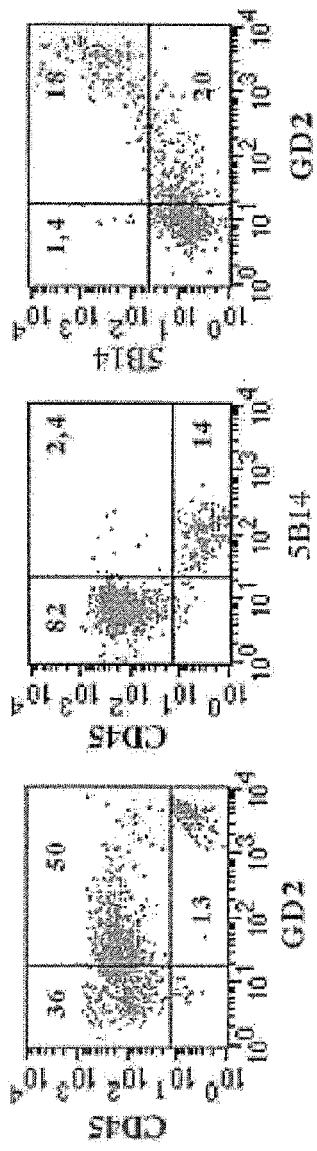
FIG. 2: Comparative cytofluorimetric analysis of 5B14 and GD2 reactivity on freshly derived neuroblastoma cells. Two representative bone marrow aspirates derived from children affected either by neuroblastoma at stage 4 (A) or at non metastatic stage 1 (B) were analyzed by double fluorescence and cytofluorimetric analysis with 5B 14 mAb or mAbs to the indicated molecules followed by PE- or FITC-conjugated goat anti-mouse isotype-specific second reagent. Three additional representative stage 4 bone marrow aspirates characterized by different number of infiltrating neuroblastoma cells are shown in panel C. Statistical analysis (in terms of % of positive cells) is indicated.

Bone marrow aspirates were derived from 16 children affected by neuroblastoma at stage 4 or (as a control), from 15 patients at the non-metastatic stage 1. Samples were analyzed by double fluorescence and cytofluorimetric analysis using either 5B14 or anti-GD2 mAbs (FIG. 2). In stage 4 samples, the anti-GD2 mAb brightly stained the infiltrating CD45-neuroblastoma cells (FIG. 2A). It is of note however, that anti-GD2 mAb also reacted with a high proportion of CD45+ normal cells. In agreement with the hypothesis that anti-GD2 mAb may bind soluble GD2 molecules shed by the neuroblastoma cell surface (Ladish, S., et al. (1987) *Int. J. Cancer.* 39, 73-76.

Figure 2B:
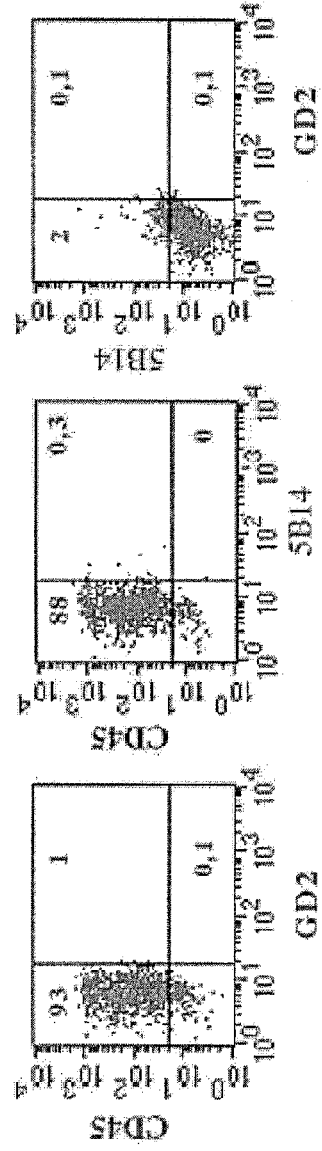
Figure 2C:
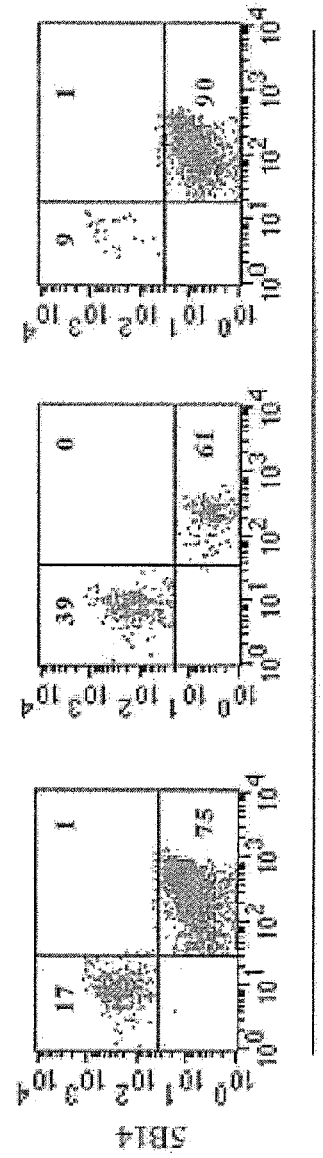

Valentino, L., et al (1990) *Blood* 75,1564-1567), anti-GD2 surface reactivity on normal cells was not detectable in samples that did not contain neuroblastoma cells, i.e. in bone marrow derived from non metastatic stage 1 patients (FIG. 2B). In stage 4 bone marrow aspirates, the infiltrating neuroblastoma cells were specifically recognized by the 5B14 mAb (FIG. 2A). Remarkably, in no instances 5B14-reactive molecules could be detected in normal CD45+ cells (FIG. 2B), as it occurs for GD2. Moreover, 5B14 surface reactivity was clearly detected regardless of the number of neuroblastoma cells infiltrating the different stage 4 bone marrow aspirates (FIG. 2C).

Immunocytochemical Analysis of Fresh Neuroblastoma Bone Marrow Infiltrates

Figures 3A, 3B, 3C, 3D:
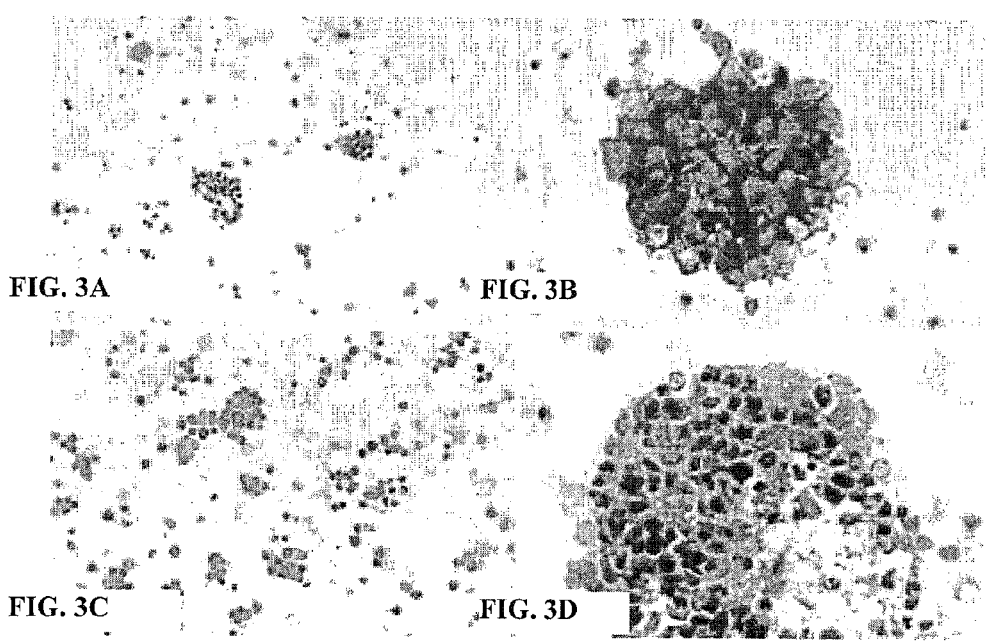
FIG. 3: Immunohistochemical detection of GD2 and 5B14 positive cells in BM aspirates from cases of stage IV neuroblastoma.Panel A: Cytospin preparation of BM aspirate (mAb GD2, APAAP, enlargement 20x.) immunostaining of single cells and clumps of NB cells. In the background, fragments showing some immunostaining. Panel B: Detail at higher magnification (mAb GD2, APAAP, 63x): the brightness of the immunostaining for mAb GD2 can mask the morphological features of the cells, thus interfering with the recognition and the quantitative evaluation of the number of NB cells. Panel C: Cytospin of BM aspirate from the same sample as in A. (mAb 5B14, APAAP, 20x). Panel D: Detail at higher magnification (mAb 5B14, APAAP, 63x) of a clump of cells from the same BM aspirate as in B. The subtler and weaker (than GD2) quality of immunostaining is visible against a somewhat "cleaner" background. The morphological features of the nuclei are readily discernible.

Bone marrow samples from patients diagnosed as having stage 4 neuroblastoma were analyzed by means of the immunocytochemical assay standardized by the E-SIOP (European International Society of Pediatric Oncology/SociétèInternationale d'Oncologie Pédiatrique) Immunocytology/Genetics Group, which is based on the detection of GD2 disialoganglioside (see Materials and Methods). Cytospins prepared with the same method from the same BM samples were tested in parallel with the 5B14 mAb. Two independent observers assessed the light microscopic features of the results. Quantitative evaluation was carried out on GD2-positive cases according to the defined minimal criteria of positively agreed upon by the ESIOP Immunocytology/Genetics Group. The results were then compared with those yielded by the 5B14 tests on the same BM samples. The staining method applied with the two monoclonal antibodies evidenced similar numbers of positive cells. Although in most samples, GD2 was highly and consistently expressed by neuroblastoma cells and not normal leukocytes, background staining was present especially in preparations containing a high number of neuroblastoma cells, such as those from most stage 4 patients at the onset of the disease (FIG. 3). This effect may interfere with positive cell discrimination and counting. Cytospins from the same cases tested with 5B14 mAb showed almost identical detection sensitivity, while non-specific or background staining was significantly less or absent (FIG. 3). In all cases the quality of staining with 5B14 mAb, although somewhat weaker or less brilliant, turned out to be decidedly more clear-cut and did not usually mask the nuclear profile or morphological details of the cells. The staining quality contributes to easier identification of the morphological hallmarks of the cells, which also plays a role in the overall evaluation of the BM samples.

Biochemical Characterization of the Surface Molecule Recognized by 5B14 mAb.

The representative 293T (embryonic fibroblasts) and ACN (neuroblastoma) human cell lines were surface labeled with 125I and cell lysates immunoprecipitated with 5B14 mAb. In both cases, 5B14 mAb immunoprecipitated a surface molecule of approximately 100 kD both under reducing (FIG. 4, panel A) and non-reducing (not shown) conditions. The protein backbone remaining after treatment with N-glycosidase F, displayed a molecular mass of approximately 60 kD, thus predicting the existence of numerous N-linked glycosylations. 5B14-reactive molecules were purified from 293T cell membranes by affinity chromatography. In-gel tryptic digested molecules were analyzed by liquid chromatography and tandem mass spectrometry (LC-MS/MS). Three different peptides allowed the identification of the 5B14-reactive molecule. It was found to correspond to a transmembrane protein of 534 amino acids characterized by four Ig-like domains in the order V/C/V/C (Sun, M., Richards, S., Prasad, D.-V., Mai, X.-M., Rudensky, A, & Dong, C. (2002) *J. Immunol.* 168, 6294-6297). This molecule has been recently termed 4Ig-B7-H3 (Steinberger, P. (2004)). In line with the biochemical analysis above, the prediction for N-glycosylation sites showed height N×S/T consensus sequences. 4Ig-B7-H3 is encoded on human chromosome 15 (15q23-q24) and appears to be the result of a gene duplication of the exons encoding the IgV-IgC domains (Sun, M., et al. (2002) *J. Immunol.* 168, 6294-6297). It is of note that the human B7-H3 was originally described as a molecule characterized by two Ig-like domains in the order V/C (Chapoval, A.-L., et al. (2001) *Nat Immunol.* 2,269-274). However, while 2Ig-B7-H3 represents the unique form found in mouse, in human it is likely to represent a short form generated by alternative splicing (Sun, M., et al. (2002)).

In order to unequivocally confirm the identity of the 5B14-reactive molecule, Chinese hamster ovarian carcinoma (CHO-K) cells transfected with 4Ig-B7-H3 cDNA were analyzed for surface reactivity with the 5B14 mAb. In all instances, no reactivity could be detected in untransfected CHO-K cells. On the other hand, 5B14 mAb strongly reacted with 4Ig-B7-H3 cell transfectants. (FIG. 4, panel B). According to the high % of identity between the distal and membrane proximal V/C domains (Steinberger, P. (2004)), 5B14 mAb also recognized 2Ig-B7-H3 cell transfectants (not shown).

4Ig-B7-H3 molecules inhibit human NK cell cytotoxicity.

Figure 5A:
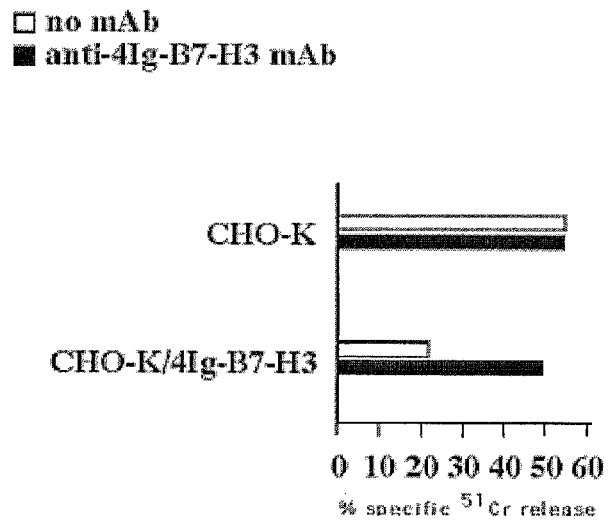
FIG. 5: 4Ig-B7-H3 molecules protect target cells from NK-mediated cytotoxicity. A polyclonal NK cell population was analyzed for cytolytic activity against CHO-K or 4Ig-B7-H3-CHO-K transfectants (panel A), or against two representative freshly purified neuroblastoma cell populations (NB1 and NB2) (panel B, left) either in the absence of mAb or in the presence of mAbs to 4Ig-B7-H3 (5B14) or HLA class I (A6-136). The effector/target ratio used was 2:1 (panel A) or 20:1 (panel B). The results are representative of three independent experiments; the standard deviation of the mean of the triplicates was <5%. Note that neuroblastoma cells were highly homogeneous as indicated by the fact that 4Ig-B7-H3 and GD2 molecules were expressed by the entire cell population (flow cytometry of NB1 and NB2in panel B, right). White profiles indicate cells incubated with the second reagent only.
Figure 5B:
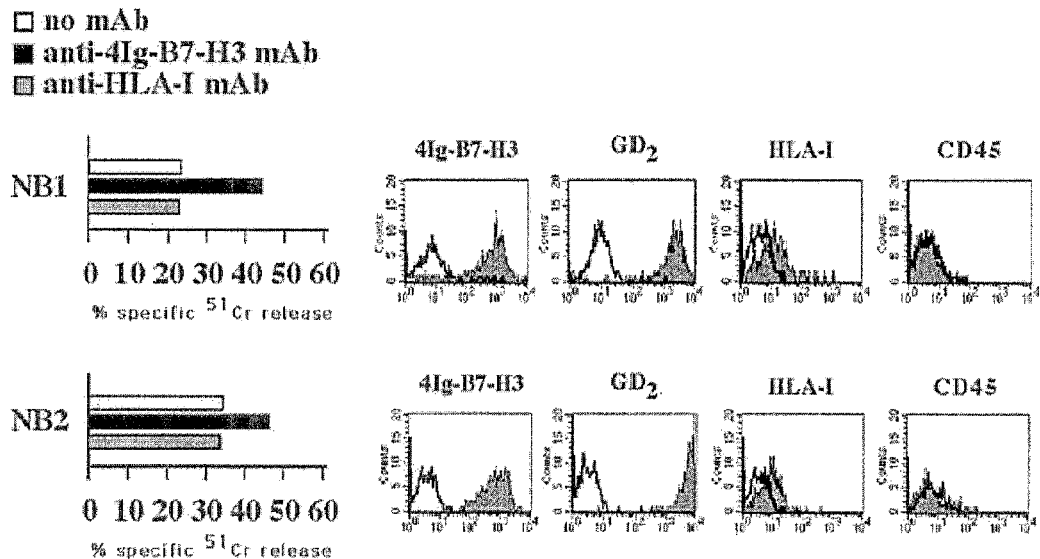

It is possible that 4Ig-B7-H3 expressed at the neuroblastoma cell surface may exert an inhibitory or enhancing effect on the NK-mediated recognition and/or lysis of the tumor cells. In order to evaluate this possibility, we analyzed the cytolytic activity of in vitro-cultured human NK cells against the CHO-K cell line either untransfected or that had been transfected with 4Ig-B7-H3 molecules. As shown in FIG. 5, panel A, NK cells efficiently lysed untransfected CHO-K cells. In this case, addition of 5B14 mAb had neither inhibitory nor enhancing effect on the cytolytic activity. On the contrary, lysis of 4Ig-B7-H3 transfected CHO-K cells was strongly reduced. Moreover, lysis could be restored in the presence of 5B14 mAb. The resulting lysis was comparable to that of untransfected CHO-K cells. These results on cell transfectants strongly suggested that 4Ig-B7-H3 molecules could also exert a "protective" role in the case of neuroblastoma cells. In order to verify this possibility, additional experiments were performed using as target cells freshly purified neuroblastoma cells derived from 5 different bone marrow aspirates of stage 4 patients. These cells were CD45– and displayed a bright fluorescence for GD2, 4Ig-B7-H3 (FIG. 5 panel B) and CD56 (not shown); i.e. they were characterized by a surface phenotype typical of neuroblastoma (Komada, Y., et al (1998) Cancer 82,591-599). Importantly, neuroblastoma cells were virtually negative for the expression of HLA class I molecules (FIG. 5 panel B) known to protect target cells from the NK-mediated attack by interacting with specific inhibitory NK receptors (Moretta, A., et al. (2002) *Nat. Immunol.* 3,6-8).

Figure 6:
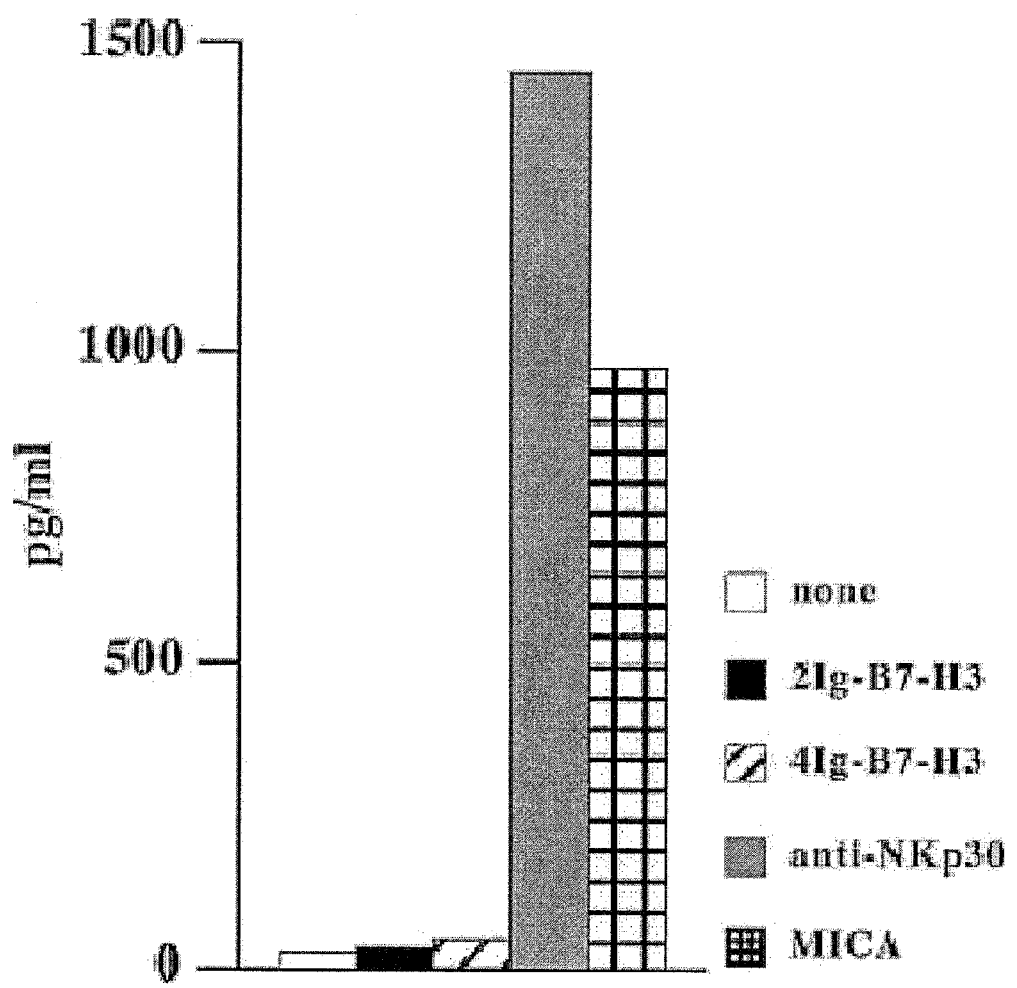
FIG. 6: B7-H3 soluble molecules do not induce IFN-gamma production by NK Cells. A representative polyclonal NK cell population from an healthy donor was stimulated or not with plate-bound soluble molecules (2Ig-B7-H3, 4Ig-B7-H3, MICA) or the anti-NKp30 mAb and IFN-gamma production was assessed by ELISA. Data are representative of 4 independent experiments.

Accordingly, mAb-mediated masking of HLA class I molecules had no enhancing effect on the NK-mediated lysis of neuroblastoma cells (FIG. 5, panel B). On the other hand, addition of 5B14 mAb resulted in a substantial enhancement of cytolysis (FIG. 5 panel B). These data clearly indicate that 4Ig-B7-H3 molecules are capable of downregulating NK cell-mediated cytotoxicity, thus protecting neuroblastoma from the NK-mediated attack. As a corollary, NK cells should necessarily express a 4Ig-B7-H3-specific receptor exerting inhibitory functions. This hypothesis is further substantiated by the fact that the engagement of this putative receptor by either 2Ig-B7-H3 or 4Ig-B7-H3 soluble molecules did not induce IFN-gamma production in polyclonal NK cells while the engagement of classical triggering NK receptors such as NKp30 or NKG2D (Andre, P. et al. (2004). *Eur J Immunol.* 34:961-971) resulted in abundant cytokine release (FIG. 6).

Thus, although an initial report suggested a costimulatory function of the putative B7-H3 receptor on T cells (Chapoval, A.-I., (2001), our present findings imply that in human NK cells it may exert inhibitory rather than activating function.

Discussion

We have identified 4Ig-B7-H3 (Sun, M., et al., (2002) *J. Immunol.* 168,6294-6297; Steinberger, P. (2004)) as a novel surface marker that is specific for neuroblastoma, at least in BM aspirates. We also show that this molecule, belonging to the B7 family, inhibits the NK-mediated lysis of neuroblastoma by interacting with a receptor expressed by NK cells. The present data may have a noticeable impact in improving the diagnosis of neuroblastoma and, possibly, in future attempts of new therapeutic approaches.

The novel 5B14 mAb, obtained by mice immunization with a neuroblastoma cell line, was found to react not only with all of the available neuroblastoma cell lines, but also with all tested freshly isolated neuroblastoma cells. 5B14 mAb allows detection, with high specificity, of tumor cells in BM aspirates from patients with methastatic, stage 4, neuroblastoma. Indeed, by double fluorescence and FACS analysis, 5B14 mAb selectively stained CD45-negative tumor cells, while anti-GD2 mAb, currently used for neuroblastoma cell identification, displayed some reactivity also with CD45+ normal hemopoietic cells. Moreover, purified CD45-negative neuroblastoma cells were homogeneously stained by 5B14 mAb. These data, together with the finding that 5B14, unlike anti-GD2 mAb (Ladish, S., et al. (1987) *Int. J. Cancer.* 39, 73-76; Valentino, L., et al., (1990) *Blood* 75,1564-1567), stained all the neuroblastoma cell lines analyzed, indicated that 5B14 mAb represents a novel valuable reagent to precisely identify neuroblastoma cells and to discriminate between tumor and normal cells.

As revealed by molecular analysis, 5B14-reactive molecules could be identified with 4Ig-B7-H3, a novel member of the B7 family that has been described very recently (Sun, M., et al., (2002) *J. Immunol.* 168,6294-6297; Steinberger, P. (2004). Importantly, the surface expression of 4Ig-B7-H3 protected tumor cells from NK-mediated killing. Thus, 4Ig-B7-H3 cell transfectants were more resistant to lysis than the corresponding untransfected target cells. In addition, 5B14 mAb-mediated masking of 4Ig-B7-H3 molecules, resulted in efficient killing of cell transfectants by NK cells. These data also suggest that NK cells express receptor(s) that, upon engagement with 4Ig-B7-H3 molecules on neuroblastoma cells, deliver inhibitory signals resulting in downregulation of NK cell cytotoxicity. This finding has been confirmed also in freshly isolated neuroblastoma cells since their lysis mediated by NK cells could be upregulated in the presence of 5B14 mAb. Thus, it is possible to speculate that the surface expression of 4Ig-B7-H3 may provide an additional mechanism allowing neuroblastoma cells to escape the control of immune response. Notably, most fresh neuroblastoma cells do not express surface HLA-class I molecules (this report), thus escaping detection by cytolytic T lymphocytes. However, upon losing HLA-class I, they become potentially susceptible to NK-mediated lysis (Garrido, F., et al. (1997) *Immunol. Today* 18,89-95). In this context, the expression of 4Ig-B7-H3, capable of inhibiting NK cell function, could represent a further mechanism of evasion by which neuroblastoma would also escape the NK-mediated control. Since 4Ig-B7-H3 is not restricted to neuroblastoma, but it is also expressed by other tumors including melanomas and carcinomas, it is conceivable that the 4Ig-B7-H3-mediated functional inhibition of NK cells may represent a more general mechanism of tumor escape from NK cells.

4Ig-B7-H3 is a novel member of the growing B7 family of cell surface ligands (Carreno, B.-M., & Collins, M. (2002) *Annu Rev Immunol.* 20,29-53; Chen, L. (2004) *Nat. Rev. Immunol.* 4: 336-347). These include B7-1 (CD80), B7-2 (CD86), B7-H2 (ICOS-L), B7-H1 (PD-L1), B7-DC (PD-L2), B7-H4 (B7S1, B7x) and BT3. They are specifically recognized by receptors displaying either activating (CD28, ICOS) or inhibitory function (CTLA-4, PD-1 and BTLA) (Carreno, B.-M., & Collins, M. (2002); Chen, L. (2004)) and are mainly expressed by T lymphocytes. Thus, the putative inhibitory receptor specific for 4Ig-B7-H3 would represent the first receptor for a B7 family member to be expressed by human NK cells. It is of note that an initial report suggested that the putative 2Ig-B7-H3-specific receptor exerted a co-stimulatory function during human T cell activation (Chapoval, A.-I., et al. (2001) *Nat Immunol.* 2,269-274). These data however, are not supported by our present results. Indeed, engagement of the putative receptor for 4Ig-B7-H3 expressed on human T cells did not result in co-stimulatory function, while the mouse 2Ig-B7-H3-specific putative receptor has been shown to function as a negative regulator for TH1 responses. Thus it seems conceivable that the 4Ig-B7-H3-specific receptor may exert an inhibitory rather than a stimulatory function in both T and NK cell-mediated responses. On the other hand, at the present it is not possible to rule out that similar to other members of this family (Suh, W.-K., et al. (2003) *Nat Immunol.* 4,899-906) two distinct receptors for B7-H3 may exist capable of transducing either positive or negative signals respectively.

It is of note that 4Ig-B7-H3 molecules are highly expressed by monocyte-derived immature or mature DC. A number of recent studies have highlighted the role of the cross-talk occurring between NK and DC in the early phases of innate immune responses as well as in shaping the subsequent T cell responses towards the TH1 phenotype (Moretta, A. (2002) *Nat Rev Immunol.* 2,957-965). Thus, one might speculate that NK-mediated recognition of 4Ig-B7-H3 molecules at the DC cell surface may play a regulatory role during NK/DC interactions. Our present data suggest that anti-4Ig-B7-H3 mAb may represent a most reliable diagnostic tool allowing specific detection of tumor cells in BM, a primary site of neuroblastoma tumor relapses. Moreover, they could offer a clue for future development of novel, NK-cell based (Ruggeri, L., Capanni, M., Urbani, E., Perruccio, K., Shlomchik, W.-D., Tosti, A., Posati, S., Rogaia, D., Frassoni, F., Aversa, F., Martelli, M.-F., & Velardi, A. (2002) *Science.* 295:2097-2100; Velardi, A., Ruggeri, L., Moretta, A., & Moretta, L. (2002) *Trends immunol.* 23:438-444), therapeutic approaches in neuroblastoma and, possibly, in other tumors expressing 4Ig-B7-H3 molecules.

All references, including publications, patent applications and patents, cited herein are hereby incorporated by reference to the same extent as if each reference were individually and specifically indicated to be incorporated by reference and were set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

REFERENCES

1. Brodeur, G.-M. Neuroblastoma. (2003) *Nat Rev Cancer.* 3,203-216.
2. Schwab, M., Westermann, F., Hero, B., & Berthold, F. (2003) *Lancet Oncol.* 4,472-480.
3. Schulz, G., Cheresh, D.-A., Varki, N.-M., Yu, A., Staffileno, L.-K., & Reisfeld R.-A. (1984) *Cancer Res.* 44,5914-5920.
4. Hakomori, S. (1984) *Annu. Rev. Immunol.* 2, 103-126
5. Ladish, S., Wu, Z.-L, Feig, S., Schwartz, E., Floutsis, G., Wiley, F., Lenarsky, C., & Seeger, R. (1987) *Int. J. Cancer.* 39, 73-76.
6. Valentino, L., Moss, T., Olson, E., Wang, H.-J., Elashoff, R., & Ladisch, S. (1990) *Blood* 75,1564-1567
7. Sivori, S., Parolini, S., Marcenaro, E., Castriconi, R., Pende, D., Millo, R., & Moretta, A. (2000) *J. Neuroimmunol.* 107:220-225.
8. Ruggeri, L., Capanni, M., Urbani, E., Perruccio, K., Shlomchik, W.-D., Tosti, A., Posati, S., Rogaia, D., Frassoni, F., Aversa, F., Martelli, M.-F., & Velardi, A. (2002) *Science.* 295:2097-2100.
9. Velardi, A., Ruggeri, L., Moretta, A., & Moretta, L. (2002) *Trends Immunol.* 23:438-444.
10. Sun, M., Richards, S., Prasad, D.-V., Mai, X.-M., Rudensky, A, & Dong, C. (2002) *J. Immunol.* 168,6294-6297
11. Steinberger, P., Majidic, O., Derdak, S.-V., Pfistershammer, K., Kirchberger, S., Klauser, C., Zlabinger, G., Pickl, W.-F., Stockl, J. & Knapp, W. (2004) *J. Immunol.* 172, 2352-2359
12. Bottino, C., Castriconi, R., Pende, D., Rivera, P., Nanni, M., Carnemolla, B., Cantoni, C., Grassi, J., Marcenaro, S., Reymond, N., Vitale, M., Moretta, L., Lopez, M., & Moretta, A. (2003) *J Exp Med.* 198,557-567.
13. Brodeur, G.-M., Pritchard, J., Berthold, F., Carlsen, N.-L., Castel, V., Castelberry, R.-P, De Bernardi, B., Evans, A.-E., Favrot, M., Hedborg, F., et al. (1993) *J Clin Oncol.* 11, 1466-1477.
14. Andre, P., Castriconi, R., Espeli, M., Anfossi. N., Juarez, T., Hue. S., Conway. H., Romagne, F., Dondero, A., Nanni, M., Caillat-Zucman, S., Raulet. D. H., Bottino, C., Vivier, E., Moretta, A. & Paul. P. (2004). *Eur J Immunol.* 34:961-971.
15. Falco, M., Marcenaro, E., Romeo, E., Bellora, F., Marras, D., Vely, F., Ferracci, G., Moretta, L., Moretta, A. & Bottino C. (2004). *Eur. J. Immunol.*
16. Chapoval, A.-I., Ni, J., Lau, J.-S., Wilcox, R.-A., Flies, D.-B., Liu, D., Dong, H., Sica, G L., Zhu, G., Tamada, K., & Chen, L. (2001) *Nat Immunol.* 2,269-274.

17. Komada, Y., Zhang, X.-L., Zhou, Y.-W., Inaba, H., Deguchi, T., Azuma, E., & Sakurai M. (1998) *Cancer.* 82,591-599.
18. Moretta, A., Bottino, C., Mingari, M.-C., Biassoni, R., & Moretta, L. (2002) *Nat Immunol.* 3,6-8.
19. Garrido, F., Ruiz-Cabello, F., Cabrera, T., Pérez-Villar, J.-J., Lòpez-Botet, M., Duggan-Keen, M., & Stern, P.-L. (1997) *Immunol. Today* 18,89-95
20. Carreno, B.-M., & Collins, M. (2002) *Annu Rev Immunol.* 20,29-53.
21. Chen, L. (2004). *Nat. Rev. Immunol.* 4: 336-347.
23. Suh, W.-K., Gajewska, B.-U., Okada, H., Gronski, M.-A., Bertram, E.-M., Dawicki, W., Duncan, G.-S., Bukczynski, J., Plyte, S., Elia, A., Wakeham, A., Itie, A., Chung, S., Da Costa, J., Arya, S., Horan, T., Campbell, P., Gaida, K., Ohashi, P.-S., Watts, T,-H., Yoshinaga, S.-K., Bray, M.-R., Jordana, M., & Mak, T.-W. (2003) *Nat Immunol.* 4,899-906.
24. Moretta, A. (2002) *Nat Rev Immunol.* 2,957-965.

We claim:

1. A method of producing an antibody suitable for use in the treatment of a tumor, said method comprising: i) providing one or a plurality of antibodies that specifically bind to a 4Ig-B7-H3 polypeptide; ii) testing the ability of each of the antibodies to block an interaction between a 4Ig-B7-H3 polypeptide and an NK cell; iii) selecting an antibody from the plurality that blocks said interaction; and iv) making the antibody suitable for human administration.

2. The method of claim 1, wherein the antibody is made suitable for human administration by humanizing or chimerizing it.

3. The method of claim 1, further comprising derivatizing the antibody into a cytotoxic antibody.

4. The method of claim 1, further comprising modifying the Fc region of the antibody to enhance the antibody's ADCC activity.

5. The method of claim 4, wherein said antibody is produced by: (a) use of an engineered host cell that is deficient in fucose metabolism such that it has a reduced ability to fucosylate proteins expressed therein; (b) culturing cells under conditions which prevent or reduce fusocylation; (c) post-translational removal of fucose; or (d) purification of the antibody so as to select for a product which is not substantially fucosylated.

6. The method of claim 1, wherein said antibody is capable of inducing the elimination of a cell to which it binds.

7. The method of claim 6, wherein said antibody has a human IgG1 or an IgG3 Fc portion.

8. The method of claim 6, wherein said antibody is linked to a cytotoxic moiety.

9. The method of claim 1, wherein said antibody has a IgG2 or an IgG4 Fc portion.

10. The method of claim 1, wherein the tumor is a neuroblastoma.

11. The method of claim 1, wherein the tumor is a melanoma.

12. The method of claim 1, wherein the tumor is a carcinoma.

13. The method of claim 4, wherein said antibody comprises one or more modifications in the Fc region at an amino acid position selected from the group consisting of 241, 243, 244, 245, 249, 256, 258, 260, 262, 264, 265, 296, 299, 301, 322, 329 and 331.

14. The method of claim 1, wherein the step of testing comprises assessing the capacity of said antibody to reconstitute lysis by 4Ig-B7-H3R-positive NK cells of 4Ig-B7-H3 positive target cells.

15. The method of claim 1, wherein the step of testing comprises assessing the ability of the antibody to inhibit the binding of 4Ig-B7-H3 molecules to 4Ig-B7-H3R expressed on NK cells.

* * * * *

UNITED STATES PATENT AND TRADEMARK OFFICE
CERTIFICATE OF CORRECTION

PATENT NO. : 8,465,931 B2
APPLICATION NO. : 12/775531
DATED : June 18, 2013
INVENTOR(S) : Alessandro Moretta et al.

It is certified that error appears in the above-identified patent and that said Letters Patent is hereby corrected as shown below:

In the Specifications

Column 1,
Line 63, "(K IRs)" should read --(KIRs)--.

Column 5,
Line 19, "Fe portion" should read --Fc portion--.
Line 46, "NK ell Activity" should read --NK cell Activity--.
Line 66, "4Ig-B7-113" should read --4Ig-B7-H3--.

Column 6,
Line 7, "4Ig-B7413" should read --4Ig-B7-H3--.
Line 14, "NK cell neutralizes" should read --NK cells, neutralizes--.

Column 8,
Line 65, "cells, In an other" should read --cells. In another--.

Column 9,
Line 15, "numuber of" should read --number of--.
Line 22, "be to use" should read --be possible to use--.

Column 10,
Line 52, "diagostic assay" should read --diagnostic assay--.

Column 12,
Line 57, "not antibody 5B 14" should read --not antibody 5B14--.

Column 13,
Line 12, "immunohistochernical" should read --immunohistochemical--.

Signed and Sealed this
Tenth Day of December, 2013

Margaret A. Focarino
*Commissioner for Patents of the United States Patent and Trademark Office*

Line 24, "recepton found" should read --receptor found--.
Line 64, "5B 14 mAb" should read --5B14 mAb--.

Column 14,
Line 25, "5B 14 mAb," should read --5B14 mAb,--.
Lines 60-61, "5B 14" should read --5B14--.

Column 15,
Line 26, "arc further" should read --are further--.

Column 19,
Line 6, "4Ig-B7-113 expressing" should read --4Ig-B7-H3 expressing--.
Line 32, "7-517 latter see," should read --7-517 (for the latter see,--.

Column 20,
Line 51, "arc then harvested" should read --are then harvested--.

Column 23,
Line 10, "antibodies 5B14)" should read --antibodies (e.g. 5B14)--.
Line 45, "5B 14." should read --5B14.--.

Column 25,
Line 9, "and anti-4Ig-B7-H3 antibodies" should read --and anti-4Ig-B7-H3R antibodies--.

Column 27,
Line 1, "4Ig-B74-H3 molecule." should read --4Ig-B7-H3 molecule.--.
Line 16, "(CD 16)" should read --(CD16)--.
Line 47, "4Ig-B74-H3 protein" should read --4Ig-B7-H3 protein--.

Column 28,
Line 9, "(CD1 6)" should read --(CD 16)--.

Column 29,
Line 62, "Immunl" should read --Immun.--.

Column 31,
Lines 40-41, "Protein. Conjugation" should read --Protein Conjugation--.
Line 56, "such as 1-131" should read --such as I-131--.

Column 33,
Line 50, "Fe-mediated" should read --Fc-mediated--.
Line 63, "Fe region" should read --Fc region--.

Column 34,
Line 12, "in its entirety'." should read --in its entirety.--.

Column 42,
Line 50, "3-[(3cholamidopropyl)dimethylamminiol" should read
--3-[(3cholamidopropyl)dimethylammoniol--.

Column 48,
Line 3, "Armu Rev" should read --Annu Rev--.

Column 54,
Line 37, "Herceptin®," should read --Herceptin®--.

Column 57,
Line 44, "This to cause" should read --This can cause--.

Column 61,
Lines 60-61, "Oncology/SocietèInternationale" should read
--Oncology/Societè Internationale--.

Column 62,
Line 14, "eases tested" should read --cases tested--.

Column 63,
Line 66, "with methastatic," should read --with metastatic,--.

Column 64,
Line 65, "2Ig-B7-H3-specific" should read --2Ig-B7-H3-specific--.

Column 65,
Line 27, "*Trends immunol.*" should read --*Trends Immunol.*--.

UNITED STATES PATENT AND TRADEMARK OFFICE
CERTIFICATE OF CORRECTION

PATENT NO. : 8,465,931 B2  
APPLICATION NO. : 12/775531  
DATED : June 18, 2013  
INVENTOR(S) : Alessandro Moretta et al.

Page 1 of 3

It is certified that error appears in the above-identified patent and that said Letters Patent is hereby corrected as shown below:

In the Specifications

Column 1,  
Line 63, "(K IRs)" should read --(KIRs)--.

Column 5,  
Line 19, "Fe portion" should read --Fc portion--.  
Line 46, "NK ell Activity" should read --NK cell Activity--.  
Line 66, "4Ig-B7-113" should read --4Ig-B7-H3--.

Column 6,  
Line 7, "4Ig-B7413" should read --4Ig-B7-H3--.  
Line 14, "NK cell neutralizes" should read --NK cells, neutralizes--.

Column 8,  
Line 65, "cells, In an other" should read --cells. In another--.

Column 9,  
Line 15, "numuber of" should read --number of--.  
Line 22, "be to use" should read --be possible to use--.

Column 10,  
Line 52, "diagostic assay" should read --diagnostic assay--.

Column 12,  
Line 57, "not antibody 5B 14" should read --not antibody 5B14--.

This certificate supersedes the Certificate of Correction issued December 10, 2013.

Signed and Sealed this  
Fifteenth Day of April, 2014

Michelle K. Lee  
*Deputy Director of the United States Patent and Trademark Office*

CERTIFICATE OF CORRECTION (continued)
U.S. Pat. No. 8,465,931 B2

Column 13,
Line 12, "immunohistochernical" should read --immunohistochemical--.
Line 24, "recepton found" should read --receptor found--.
Line 64, "5B 14 mAb" should read --5B14 mAb--.

Column 14,
Line 25, "5B 14 mAb," should read --5B14 mAb,--.
Lines 60-61, "5B 14" should read --5B14--.

Column 15,
Line 26, "arc further" should read --are further--.

Column 19,
Line 6, "4Ig-B7-113 expressing" should read --4Ig-B7-H3 expressing--.
Line 32, "7-517 latter see," should read --7-517 (for the latter see,--.

Column 20,
Line 51, "arc then harvested" should read --are then harvested--.

Column 23,
Line 10, "antibodies 5B14)" should read --antibodies (e.g. 5B14)--.
Line 45, "5B 14." should read --5B14.--.

Column 25,
Line 9, "and anti-4Ig-B7-H3 antibodies" should read --and anti-4Ig-B7-H3R antibodies--.

Column 27,
Line 1, "4Ig-B74-H3 molecule." should read --4Ig-B7-H3 molecule.--.
Line 16, "(CD 16)" should read --(CD 16)--.
Line 47, "4Ig-B74-H3 protein" should read --4Ig-B7-H3 protein--.

Column 28,
Line 9, "(CD1 6)" should read --(CD 16)--.

Column 29,
Line 62, "Immunl" should read --Immun.--.

Column 31,
Lines 40-41, "Protein. Conjugation" should read --Protein Conjugation--.
Line 56, "such as 1-131" should read --such as I-131--.

Column 33,
Line 50, "Fe-mediated" should read --Fc-mediated--.
Line 63, "Fe region" should read --Fc region--.

CERTIFICATE OF CORRECTION (continued)
U.S. Pat. No. 8,465,931 B2

Column 34,
Line 12, "in its entirety'." should read --in its entirety.--.

Column 42,
Line 50, "3-[(3cholamidopropyl)dimethylamminiol" should read
--3-[(3cholamidopropyl)dimethylammoniol--.

Column 48,
Line 3, "Armu Rev" should read --Annu Rev--.

Column 54,
Line 37, "Herceptin®," should read --Herceptin®--.

Column 57,
Line 44, "This to cause" should read --This can cause--.

Column 61,
Lines 60-61, "Oncology/SociétèInternationale" should read --Oncology/Sociétè Internationale--.

Column 62,
Line 14, "eases tested" should read --cases tested--.

Column 63,
Line 66, "with methastatic," should read --with metastatic,--.

Column 64,
Line 65, "21g-B7-H3-specific" should read --2Ig-B7-H3-specific--.

Column 65,
Line 27, "*Trends immunol.*" should read --*Trends Immunol.*--.

UNITED STATES PATENT AND TRADEMARK OFFICE
CERTIFICATE OF CORRECTION

PATENT NO. : 8,465,931 B2  
APPLICATION NO. : 12/775531  
DATED : June 18, 2013  
INVENTOR(S) : Alessandro Moretta et al.

Page 1 of 3

It is certified that error appears in the above-identified patent and that said Letters Patent is hereby corrected as shown below:

In the Specifications

Column 1,  
Line 63, "(K IRs)" should read --(KIRs)--.

Column 5,  
Line 19, "Fe portion" should read --Fc portion--.  
Line 46, "NK ell Activity" should read --NK cell Activity--.  
Line 66, "4Ig-B7-113" should read --4Ig-B7-H3--.

Column 6,  
Line 7, "4Ig-B7413" should read --4Ig-B7-H3--.  
Line 14, "NK cell neutralizes" should read --NK cells, neutralizes--.

Column 8,  
Line 65, "cells, In an other" should read --cells. In another--.

Column 9,  
Line 15, "numuber of" should read --number of--.  
Line 22, "be to use" should read --be possible to use--.

Column 10,  
Line 52, "diagostic assay" should read --diagnostic assay--.

Column 12,  
Line 57, "not antibody 5B 14" should read --not antibody 5B14--.

This certificate supersedes the Certificates of Correction issued December 10, 2013 and April 15, 2014.

Signed and Sealed this  
Twenty-second Day of July, 2014

Michelle K. Lee  
*Deputy Director of the United States Patent and Trademark Office*

Column 13,
Line 12, "immunohistochernical" should read --immunohistochemical--.
Line 24, "recepton found" should read --receptor found--.
Line 64, "5B 14 mAb" should read --5B14 mAb--.

Column 14,
Line 25, "5B 14 mAb," should read --5B14 mAb,--.
Lines 60-61, "5B 14" should read --5B14--.

Column 15,
Line 26, "arc further" should read --are further--.

Column 19,
Line 6, "4Ig-B7-113 expressing" should read --4Ig-B7-H3 expressing--.
Line 32, "7-517 latter see," should read --7-517 (for the latter see,--.

Column 20,
Line 51, "arc then harvested" should read --are then harvested--.

Column 23,
Line 10, "antibodies 5B14)" should read --antibodies (e.g. 5B14)--.
Line 45, "5B 14." should read --5B14.--.

Column 25,
Line 9, "and anti-4Ig-B7-H3 antibodies" should read --and anti-4Ig-B7-H3R antibodies--.

Column 27,
Line 1, "4Ig-B74-H3 molecule." should read --4Ig-B7-H3 molecule.--.
Line 16, "(CD 16)" should read --(CD16)--.
Line 47, "4Ig-B74-H3 protein" should read --4Ig-B7-H3 protein--.

Column 28,
Line 9, "(CD1 6)" should read --(CD16)--.

Column 29,
Line 62, "Immunl" should read --Immun.--.

Column 31,
Lines 40-41, "Protein. Conjugation" should read --Protein Conjugation--.
Line 56, "such as 1-131" should read --such as I-131--.

Column 33,
Line 50, "Fe-mediated" should read --Fc-mediated--.
Line 63, "Fe region" should read --Fc region--.

Column 34,
Line 12, "in its entirety'." should read --in its entirety.--.

Column 42,
Line 50, "3-[(3cholamidopropyl)dimethylamminiol" should read
--3-[(3cholamidopropyl)dimethylammoniol--.

Column 48,
Line 3, "Armu Rev" should read --Annu Rev--.

Column 54,
Line 37, "Herceptin®," should read --Herceptin®--.

Column 57,
Line 44, "This to cause" should read --This can cause--.

Column 61,
Lines 60-61, "Oncology/SociétèInternationale" should read --Oncology/Sociétè Internationale--.

Column 62,
Line 14, "eases tested" should read --cases tested--.

Column 63,
Line 66, "with methastatic," should read --with metastatic,--.

Column 64,
Line 65, "21g-B7-H3-specific" should read --2Ig-B7-H3-specific--.

Column 65,
Line 27, "*Trends immunol.*" should read --*Trends Immunol.*--.